(12) United States Patent
Bentley et al.

(10) Patent No.: US 9,349,049 B2
(45) Date of Patent: May 24, 2016

(54) MOTION CAPTURE AND ANALYSIS SYSTEM

(71) Applicant: BLAST MOTION INC., Burlingame, CA (US)

(72) Inventors: Michael Bentley, Encinitas, CA (US); Bhaskar Bose, Carlsbad, CA (US); Ryan Kaps, Mesa, AZ (US)

(73) Assignee: BLAST MOTION INC., Burlingame, CA (US)

( * ) Notice: Subject to any disclaimer, the term of this patent is extended or adjusted under 35 U.S.C. 154(b) by 0 days.

(21) Appl. No.: 14/605,940

(22) Filed: Jan. 26, 2015

(65) Prior Publication Data

US 2015/0269435 A1 Sep. 24, 2015

Related U.S. Application Data

(63) Continuation of application No. 13/219,525, filed on Aug. 26, 2011, now Pat. No. 8,941,723, which is a continuation-in-part of application No. 13/191,309, filed on Jul. 26, 2011, now Pat. No. 9,033,810, which (Continued)

(51) Int. Cl.
*G06K 9/00* (2006.01)
*G06T 7/20* (2006.01)
*H04N 7/18* (2006.01)

(52) U.S. Cl.
CPC ........ *G06K 9/00624* (2013.01); *G06K 9/00342* (2013.01); *G06T 7/20* (2013.01); *H04N 7/181* (2013.01)

(58) Field of Classification Search
CPC .................................................. G06K 9/00624
See application file for complete search history.

(56) References Cited

U.S. PATENT DOCUMENTS 1,712,537 A 5/1929 White
3,182,508 A 5/1965 Varju (Continued)

FOREIGN PATENT DOCUMENTS

EP 2025369 A2 2/2009
JP 2004207985 7/2004

(Continued)

OTHER PUBLICATIONS

Zepp Golfsense@Launch2011, https://www.youtube.com/watch?v=VnOcu8szjIk (video), Mar. 14, 2011.

(Continued)

*Primary Examiner* — Nhon Diep
*Assistant Examiner* — Berteau Joisil
(74) *Attorney, Agent, or Firm* — ARC IP Law, PC; Joseph J. Mayo

(57) ABSTRACT

Portable wireless mobile device motion capture and analysis system and method configured to display motion capture/analysis data on a mobile device. System obtains data from motion capture elements and analyzes the data. Enables unique displays associated with the user, such as 3D overlays onto images of the user to visually depict the captured motion data. Ratings associated with the captured motion can also be displayed. Predicted ball flight path data can be calculated and displayed. Data shown on a time line can also be displayed to show the relative peaks of velocity for various parts of the user's body. Based on the display of data, the user can determine the equipment that fits the best and immediately purchase the equipment, via the mobile device. Custom equipment may be ordered through an interface on the mobile device from a vendor that can assemble-to-order customer built equipment and ship the equipment.

26 Claims, 44 Drawing Sheets

Related U.S. Application Data is a continuation-in-part of application No. 13/048,850, filed on Mar. 15, 2011, now Pat. No. 8,465,376, which is a continuation-in-part of application No. 12/901,806, filed on Oct. 11, 2010, which is a continuation-in-part of application No. 12/868,882, filed on Aug. 26, 2010, now Pat. No. 8,994,826.

(56) References Cited

U.S. PATENT DOCUMENTS

| | | |
|---|---|---|
| 3,226,704 A | 12/1965 | Petrash |
| 3,270,564 A | 9/1966 | Evans |
| 3,788,647 A | 1/1974 | Evans |
| 3,792,863 A | 2/1974 | Evans |
| 3,806,131 A | 4/1974 | Evans |
| 3,945,646 A | 3/1976 | Hammond |
| 4,759,219 A | 7/1988 | Cobb et al. |
| 4,898,389 A | 2/1990 | Plutt |
| 4,902,014 A | 2/1990 | Bontomase et al. |
| 4,910,677 A | 3/1990 | Remedio et al. |
| 4,940,236 A | 7/1990 | Allen |
| 4,991,850 A | 2/1991 | Wilhlem |
| 5,056,783 A | 10/1991 | Matcovich et al. |
| 5,086,390 A | 2/1992 | Matthews |
| 5,111,410 A | 5/1992 | Nakayama et al. |
| 5,127,044 A | 6/1992 | Bonito et al. |
| 5,184,295 A | 2/1993 | Mann |
| 5,230,512 A | 7/1993 | Tattershall |
| 5,233,544 A | 8/1993 | Kobayashi |
| 5,249,967 A | 10/1993 | O'Leary et al. |
| 5,259,620 A | 11/1993 | Marocco |
| 5,283,733 A | 2/1994 | Colley |
| 5,298,904 A | 3/1994 | Olich |
| 5,332,225 A | 7/1994 | Ura |
| 5,333,061 A | 7/1994 | Nakashami et al. |
| 5,364,093 A | 11/1994 | Huston et al. |
| 5,372,365 A | 12/1994 | McTeigue et al. |
| 5,441,256 A | 8/1995 | Hackman |
| 5,441,269 A | 8/1995 | Henwood |
| 5,486,001 A | 1/1996 | Baker |
| 5,524,081 A | 6/1996 | Paul |
| 5,542,676 A | 8/1996 | Howe et al. |
| 5,592,401 A | 1/1997 | Kramer |
| 5,610,590 A | 3/1997 | Johnson et al. |
| 5,638,300 A | 6/1997 | Johnson |
| 5,665,006 A | 9/1997 | Pellegrini |
| 5,688,183 A | 11/1997 | Sabatino et al. |
| 5,694,340 A | 12/1997 | Kim |
| 5,772,522 A | 6/1998 | Nesbit |
| 5,779,555 A | 7/1998 | Nomura et al. |
| 5,792,001 A | 8/1998 | Henwood |
| 5,819,206 A | 10/1998 | Horton |
| 5,826,578 A | 10/1998 | Curchod |
| 5,868,578 A | 2/1999 | Baum |
| 5,904,484 A | 5/1999 | Burns |
| 5,941,779 A | 8/1999 | Zeiner-Gundersen |
| 5,973,596 A | 10/1999 | French et al. |
| 5,998,968 A | 12/1999 | Pittman et al. |
| 6,012,995 A | 1/2000 | Martin |
| 6,030,109 A | 2/2000 | Lobsenz |
| 6,044,704 A | 4/2000 | Sacher |
| 6,073,086 A | 6/2000 | Marinelli |
| 6,224,493 B1 | 5/2001 | Lee et al. |
| 6,248,021 B1 | 6/2001 | Ognjanovic |
| 6,266,623 B1 | 7/2001 | Vock et al. |
| 6,293,802 B1 | 9/2001 | Ahlgren |
| 6,366,205 B1 | 4/2002 | Sutphen |
| 6,441,745 B1 | 8/2002 | Gates |
| 6,456,938 B1 | 9/2002 | Barnard |
| 6,537,076 B2 | 3/2003 | McNitt |
| 6,537,536 B1 | 3/2003 | Kronberg et al. |
| 6,540,620 B1 | 4/2003 | Consiglio |
| 6,567,536 B2 | 5/2003 | McNitt |
| 6,582,328 B2 | 6/2003 | Kuta et al. |
| 6,611,141 B1 | 8/2003 | Schulz et al. |
| 6,697,820 B1 | 2/2004 | Tarlie |
| 6,705,942 B1 | 3/2004 | Crook et al. |
| 6,746,336 B1 | 6/2004 | Brant et al. |
| 6,757,572 B1 | 6/2004 | Forest |
| 6,774,932 B1 | 8/2004 | Ewing et al. |
| 6,802,772 B1 | 10/2004 | Kunzle et al. |
| 6,868,338 B1 | 3/2005 | Elliott |
| 6,900,759 B1 | 5/2005 | Katayama |
| 6,908,404 B1 | 6/2005 | Gard |
| 6,923,729 B2 | 8/2005 | McGinty et al. |
| 7,004,848 B2 | 2/2006 | Konow |
| 7,021,140 B2 | 4/2006 | Perkins |
| 7,034,694 B2 | 4/2006 | Yamaguchi et al. |
| 7,037,198 B2 | 5/2006 | Hameen-Antilla |
| 7,092,846 B2 | 8/2006 | Vock et al. |
| 7,118,498 B2 | 10/2006 | Meadows et al. |
| 7,121,962 B2 | 10/2006 | Reeves |
| 7,143,639 B2 | 12/2006 | Gobush |
| 7,160,200 B2 | 1/2007 | Grober |
| 7,175,177 B2 | 2/2007 | Meifu et al. |
| 7,205,894 B1 | 4/2007 | Savage |
| 7,212,943 B2 | 5/2007 | Aoshima et al. |
| 7,219,033 B2 | 5/2007 | Kolen |
| 7,234,351 B2 | 6/2007 | Perkins |
| 7,264,554 B2 | 9/2007 | Bentley |
| 7,283,647 B2 | 10/2007 | Mcnitt |
| 7,421,369 B2 | 9/2008 | Clarkson |
| 7,433,805 B2 | 10/2008 | Vock et al. |
| 7,457,439 B1 | 11/2008 | Madsen |
| 7,457,724 B2 | 11/2008 | Vock et al. |
| 7,492,367 B2 | 2/2009 | Mahajan et al. |
| 7,494,236 B2 | 2/2009 | Lim |
| 7,499,828 B2 | 3/2009 | Barton |
| 7,561,989 B2 | 7/2009 | Banks |
| 7,623,987 B2 | 11/2009 | Vock et al. |
| 7,627,451 B2 | 12/2009 | Vock et al. |
| 7,689,378 B2 | 3/2010 | Kolen |
| 7,713,148 B2 | 5/2010 | Sweeney |
| 7,736,242 B2 | 6/2010 | Stites et al. |
| 7,771,263 B2 | 8/2010 | Telford |
| 7,780,450 B2 | 8/2010 | Tarry |
| 7,800,480 B1 | 9/2010 | Joseph et al. |
| 7,813,887 B2 | 10/2010 | Vock et al. |
| 7,831,212 B1 | 11/2010 | Balardeta et al. |
| 7,871,333 B1 | 1/2011 | Davenport |
| 7,966,154 B2 | 6/2011 | Vock et al. |
| 7,983,876 B2 | 7/2011 | Vock et al. |
| 8,036,826 B2 | 10/2011 | MacIntosh et al. |
| 8,117,888 B2 | 2/2012 | Chan et al. |
| 8,172,722 B2 | 5/2012 | Molyneux et al. |
| 8,231,506 B2 | 7/2012 | Molyneux et al. |
| 8,249,831 B2 | 8/2012 | Vock et al. |
| 8,257,191 B2 | 9/2012 | Stites et al. |
| 8,282,487 B2 | 10/2012 | Wilson et al. |
| 8,314,840 B1 | 11/2012 | Funk et al. |
| 8,352,211 B2 | 1/2013 | Vock et al. |
| 8,400,548 B2 | 3/2013 | Bilbrey et al. |
| 8,425,292 B2 | 4/2013 | Lui et al. |
| 8,527,228 B2 | 9/2013 | Panagas |
| 8,565,483 B2 | 10/2013 | Nakaoka |
| 8,725,452 B2 | 5/2014 | Han |
| 8,764,576 B2 | 7/2014 | Takasugi |
| 8,781,610 B2 | 7/2014 | Han |
| 8,876,621 B2 | 11/2014 | Shibuya |
| 8,888,603 B2 | 11/2014 | Sato et al. |
| 8,929,709 B2 | 1/2015 | Lokshin |
| 8,944,932 B2 | 2/2015 | Sato et al. |
| 8,956,238 B2 | 2/2015 | Boyd et al. |
| 8,989,441 B2 | 3/2015 | Han et al. |
| 9,060,682 B2 | 6/2015 | Lokshin |
| 9,146,134 B2 | 9/2015 | Lokshin et al. |
| 2001/0029207 A1 | 10/2001 | Cameron et al. |
| 2001/0035880 A1 | 11/2001 | Musatov et al. |
| 2001/0045904 A1 | 11/2001 | Silzer, Jr. |
| 2001/0049636 A1 | 12/2001 | Hudda et al. |
| 2002/0004723 A1 | 1/2002 | Meifu et al. |
| 2002/0019677 A1 | 2/2002 | Lee |
| 2002/0049507 A1 | 4/2002 | Hameen-Anttila |
| 2002/0052750 A1 | 5/2002 | Hirooka |

(56) References Cited

U.S. PATENT DOCUMENTS

| | | |
|---|---|---|
| 2002/0064764 A1 | 5/2002 | Fishman |
| 2002/0072815 A1 | 6/2002 | McDonough et al. |
| 2002/0077189 A1 | 6/2002 | Tuer et al. |
| 2002/0082775 A1 | 6/2002 | Meadows et al. |
| 2002/0126157 A1 | 9/2002 | Farago et al. |
| 2002/0151994 A1 | 10/2002 | Sisco |
| 2002/0173364 A1 | 11/2002 | Boscha |
| 2002/0177490 A1 | 11/2002 | Yong et al. |
| 2002/0188359 A1 | 12/2002 | Morse |
| 2003/0008722 A1 | 1/2003 | Konow |
| 2003/0073518 A1 | 4/2003 | Marty et al. |
| 2003/0074659 A1 | 4/2003 | Louzoun et al. |
| 2003/0109322 A1 | 6/2003 | Funk et al. |
| 2003/0191547 A1 | 10/2003 | Morse |
| 2003/0208830 A1 | 11/2003 | Marmaropoulos et al. |
| 2004/0028258 A1 | 2/2004 | Naimark et al. |
| 2004/0033843 A1 | 2/2004 | Miller et al. |
| 2004/0044493 A1 | 3/2004 | Coulthard |
| 2004/0147329 A1 | 7/2004 | Meadows et al. |
| 2004/0227676 A1 | 11/2004 | Kim et al. |
| 2004/0248676 A1 | 12/2004 | Taylor |
| 2005/0021292 A1 | 1/2005 | Vock et al. |
| 2005/0032582 A1 | 2/2005 | Mahajan et al. |
| 2005/0054457 A1 | 3/2005 | Eyestone et al. |
| 2005/0156068 A1 | 7/2005 | Ivans |
| 2005/0203430 A1 | 9/2005 | Williams et al. |
| 2005/0213076 A1 | 9/2005 | Saegusa |
| 2005/0215340 A1 | 9/2005 | Stites et al. |
| 2005/0227775 A1 | 10/2005 | Cassady et al. |
| 2005/0261073 A1 | 11/2005 | Farrington, Jr. et al. |
| 2005/0268704 A1 | 12/2005 | Bissonnette et al. |
| 2005/0272516 A1 | 12/2005 | Gobush |
| 2005/0282650 A1 | 12/2005 | Miettinen et al. |
| 2005/0288119 A1* | 12/2005 | Wang .................... A63B 69/36 473/223 |
| 2006/0020177 A1 | 1/2006 | Seo et al. |
| 2006/0025229 A1 | 2/2006 | Mahajan et al. |
| 2006/0038657 A1 | 2/2006 | Denison et al. |
| 2006/0063600 A1 | 3/2006 | Grober |
| 2006/0068928 A1 | 3/2006 | Nagy |
| 2006/0084516 A1 | 4/2006 | Eyestone et al. |
| 2006/0109116 A1 | 5/2006 | Keays |
| 2006/0122002 A1 | 6/2006 | Konow |
| 2006/0166738 A1 | 7/2006 | Eyestone et al. |
| 2006/0189389 A1* | 8/2006 | Hunter .................... G07F 17/32 463/42 |
| 2006/0199659 A1 | 9/2006 | Caldwell |
| 2006/0250745 A1 | 11/2006 | Butler et al. |
| 2006/0270450 A1 | 11/2006 | Garratt et al. |
| 2006/0276256 A1 | 12/2006 | Storek |
| 2006/0284979 A1 | 12/2006 | Clarkson |
| 2007/0052807 A1 | 3/2007 | Zhou et al. |
| 2007/0062284 A1 | 3/2007 | Machida |
| 2007/0081695 A1 | 4/2007 | Foxlin et al. |
| 2007/0087866 A1 | 4/2007 | Meadows et al. |
| 2007/0099715 A1 | 5/2007 | Jones et al. |
| 2007/0111811 A1 | 5/2007 | Grober |
| 2007/0129178 A1 | 6/2007 | Reeves |
| 2007/0135225 A1* | 6/2007 | Nieminen .......... A63B 24/0006 473/212 |
| 2007/0135237 A1 | 6/2007 | Reeves |
| 2007/0219744 A1 | 9/2007 | Kolen |
| 2007/0265105 A1 | 11/2007 | Barton |
| 2007/0270214 A1* | 11/2007 | Bentley ................ A61B 5/1122 463/30 |
| 2007/0298896 A1 | 12/2007 | Nusbaum |
| 2008/0085778 A1 | 4/2008 | Dugan |
| 2008/0108456 A1 | 5/2008 | Bonito |
| 2008/0164999 A1 | 7/2008 | Otto |
| 2008/0190202 A1 | 8/2008 | Kulach et al. |
| 2008/0234935 A1 | 9/2008 | Wolf et al. |
| 2008/0280642 A1 | 11/2008 | Coxhill et al. |
| 2008/0285805 A1 | 11/2008 | Luinge et al. |
| 2009/0017944 A1 | 1/2009 | Savarese et al. |
| 2009/0029754 A1 | 1/2009 | Slocum et al. |
| 2009/0033741 A1 | 2/2009 | Oh et al. |
| 2009/0036237 A1 | 2/2009 | Nipper et al. |
| 2009/0048044 A1 | 2/2009 | Oleson et al. |
| 2009/0088276 A1 | 4/2009 | Solheim et al. |
| 2009/0111602 A1 | 4/2009 | Savarese et al. |
| 2009/0131190 A1 | 5/2009 | Kimber |
| 2009/0137333 A1 | 5/2009 | Lin et al. |
| 2009/0174676 A1 | 7/2009 | Westerman |
| 2009/0177097 A1 | 7/2009 | Ma et al. |
| 2009/0209343 A1 | 8/2009 | Foxlin |
| 2009/0209358 A1 | 8/2009 | Niegowski |
| 2009/0213134 A1 | 8/2009 | Stephanick et al. |
| 2009/0222163 A1 | 9/2009 | Plante |
| 2009/0233735 A1 | 9/2009 | Savarese et al. |
| 2009/0254971 A1 | 10/2009 | Herz |
| 2009/0299232 A1 | 12/2009 | Lanfermann et al. |
| 2010/0049468 A1 | 2/2010 | Papadourakis |
| 2010/0062869 A1 | 3/2010 | Chung et al. |
| 2010/0063778 A1 | 3/2010 | Schrock et al. |
| 2010/0063779 A1 | 3/2010 | Schrock et al. |
| 2010/0091112 A1 | 4/2010 | Veeser et al. |
| 2010/0093458 A1 | 4/2010 | Davenport et al. |
| 2010/0099509 A1 | 4/2010 | Ahem et al. |
| 2010/0103269 A1 | 4/2010 | Wilson et al. |
| 2010/0113174 A1 | 5/2010 | Ahern |
| 2010/0121228 A1 | 5/2010 | Stirling et al. |
| 2010/0130298 A1 | 5/2010 | Dugan et al. |
| 2010/0144414 A1 | 6/2010 | Edis et al. |
| 2010/0144456 A1 | 6/2010 | Ahern |
| 2010/0216564 A1 | 8/2010 | Stites et al. |
| 2010/0222152 A1 | 9/2010 | Jaekel et al. |
| 2010/0308105 A1 | 12/2010 | Savarese et al. |
| 2010/0323794 A1 | 12/2010 | Su |
| 2011/0037778 A1 | 2/2011 | Deng et al. |
| 2011/0050864 A1 | 3/2011 | Bond |
| 2011/0052005 A1 | 3/2011 | Selner |
| 2011/0053688 A1 | 3/2011 | Crawford |
| 2011/0075341 A1 | 3/2011 | Lau et al. |
| 2011/0081981 A1 | 4/2011 | Okamoto |
| 2011/0165998 A1 | 7/2011 | Lau et al. |
| 2011/0230273 A1 | 9/2011 | Niegowski et al. |
| 2011/0230274 A1 | 9/2011 | Lafortune et al. |
| 2011/0230985 A1 | 9/2011 | Niegowski et al. |
| 2011/0230986 A1 | 9/2011 | Lafortune |
| 2011/0238308 A1 | 9/2011 | Miller et al. |
| 2011/0305369 A1 | 12/2011 | Bentley |
| 2012/0023354 A1 | 1/2012 | Chino |
| 2012/0115682 A1 | 5/2012 | Homsi |
| 2012/0116548 A1 | 5/2012 | Goree et al. |
| 2012/0157241 A1 | 6/2012 | Nomura et al. |
| 2012/0179418 A1 | 7/2012 | Takasugi et al. |
| 2012/0191405 A1 | 7/2012 | Molyneux et al. |
| 2012/0316004 A1 | 12/2012 | Shibuya |
| 2013/0110415 A1 | 5/2013 | Davis et al. |
| 2013/0173212 A1 | 7/2013 | Saiki et al. |
| 2013/0191063 A1 | 7/2013 | Nomura |
| 2013/0271602 A1 | 10/2013 | Bentley et al. |
| 2013/0298668 A1 | 11/2013 | Sato |
| 2013/0319113 A1 | 12/2013 | Mizuta |
| 2013/0330054 A1 | 12/2013 | Lokshin |
| 2013/0332004 A1 | 12/2013 | Gompert et al. |
| 2013/0346013 A1 | 12/2013 | Lokshin |
| 2014/0019083 A1 | 1/2014 | Nakaoka |
| 2014/0100048 A1 | 4/2014 | Ota et al. |
| 2014/0100049 A1 | 4/2014 | Ota et al. |
| 2014/0100050 A1 | 4/2014 | Ota et al. |
| 2014/0135139 A1 | 5/2014 | Shibuya et al. |
| 2014/0156214 A1 | 6/2014 | Nomura |
| 2014/0172873 A1 | 6/2014 | Varoglu et al. |
| 2014/0229135 A1 | 8/2014 | Nomura |
| 2014/0257743 A1 | 9/2014 | Lokshin et al. |
| 2014/0257744 A1 | 9/2014 | Lokshin et al. |
| 2014/0295982 A1 | 10/2014 | Shibuya |
| 2014/0378239 A1 | 12/2014 | Sato et al. |
| 2014/0379293 A1 | 12/2014 | Sato |
| 2014/0379294 A1 | 12/2014 | Shibuya et al. |
| 2014/0379295 A1 | 12/2014 | Sato et al. |
| 2015/0007658 A1 | 1/2015 | Ishikawa et al. |
| 2015/0012240 A1 | 1/2015 | Sato |

(56) References Cited

U.S. PATENT DOCUMENTS

| | | |
|---|---|---|
| 2015/0042481 A1 | 2/2015 | Nomura |
| 2015/0098688 A1 | 4/2015 | Lokshin |
| 2015/0256689 A1 | 9/2015 | Erkkila et al. |

FOREIGN PATENT DOCUMENTS

| | | |
|---|---|---|
| JP | 2011-000367 | 6/2011 |
| JP | 2012196241 | 10/2012 |
| KR | 10-2003-0085275 | 5/2003 |
| KR | 10-2006-0041060 | 5/2006 |
| KR | 10-2007-0119018 | 12/2007 |
| KR | 10-2010-0074068 | 1/2010 |
| KR | 10-1079319 | 4/2011 |
| KR | 10-2010-0020131 | 9/2011 |
| WO | 94/27683 | 8/1994 |
| WO | 2011057194 | 5/2011 |

OTHER PUBLICATIONS

Epson US Newsroom, "Epson America Enters Sports Wearables Market with Introduction of M-Tracer MT500GII Golf Swing Analyzer", www.news.epson.com, Jan. 5, 2015, 4 pages.
International Search Report for PCT Application No. PCT/US2015/26896, dated Jul. 28, 2015, 15 pages.
International Search Report for PCT Application No. PCTUS2015/26917, dated Jul. 30, 2015, 16 pages.
International Search Report received for PCT Application No. PCT/US2012/065716, dated Jan. 3, 2013, 10 pages.
myCaddie, 2009, retrieved on Sep. 26, 2012 from http://www.iMakePars.com, 4 pages.
Swing it See it Fix it, Improve Gold Swing, SwingSmart Golf Analyzer, retrieved on Sep. 26, 2012 from http://www.SwingSmart.com, 2 pages.
Learn how Swingbyte can improve your game, retrieved on Sep. 26, 2012 from http://www.swingbyte.com, 2 pages.
International Search Report received for PCT Application No. PCT/US2011/055173, Mar. 6, 2012, 8 pages.
International Search Report received for PCT Application No. PCT/US2011/049461, Feb. 23, 2012, 14 pages.
PCT Search Report, PCT/US2012/029310, dated Sep. 28, 2012, 3 pages.
IPER, PCT/US2011/049461, dated Mar. 7, 2013, 6 pages.
IPER, PCT/US2011/049461, dated May 10, 2013, 5 pages.
IPER, PCT/US2011/055173, dated Apr. 25, 2013, 5 pages.
IPRP, PCT/US2012/065716, dated May 30, 2014, 6 pages.
International Search Report for PCT Application No. PCT/US2013/021999, dated Apr. 30, 2013, 8 pages.
International Search Report for PCT Application No. PCT/US2012/066915, dated Mar. 29, 2013, 10 pages.
The Nike+FuelBand User's Guide, rev 14, 26 pages.
UP by Jawbone Extended User Guide, 10 pages.
Armour39, Under Armour Guarantee, Getting Started, retrieved from the Internet on Jul. 12, 2013, 7 pages.
Armour39 Module & Chest Strap, retrieved from the Internet on Jul. 12, 2013, 6 pages.
miCoach Pacer User Manual, 31 pages.
Foreman et al. "A Comparative Analysis for the Measurement of Head Accelerations in Ice Hockey Helmets using Non-Accelerometer Based Systems," Nov. 19, 2012, 13 pages.
Reebok-CCM and MC10 to Launch Revolutionary Sports Impact Indicator, MC10 News (http://www.mc10inc.com/news/), Oct. 24, 2012, 3 pages.
CheckLight MC10 Overview, Reebok International Limited, Nov. 20, 2012, 7 pages.
Reebok and MC10 Team Up to Build CheckLight, a Head Impact Indicator (Hands-on), MC10 News (http://www.mc10inc.com/news/), Jan. 11, 2013, 1 pg.
Trace—The Most Advanced Activity Monitor for Action Sports, webpage, retrieved on Aug. 6, 2013, 22 pages.
CheckLight, Sports/Activity Impact Indicator, User Manual, 13 pages, 2013, Reebok International Limited.
King, The Design and Application of Wireless Mems Inertial Measurement Units for the Measurement and Analysis of Golf Swings, 2008.
Grober, An Accelerometer Based Instrumentation of the Golf Club: Comparative Analysis of Golf Swings, 2009.
Gehrig et al, Visual Golf Club Tracking for Enhanced Swing Analysis, Computer Vision Lab, Lausanne, Switzerland, undated.
PocketPro Golf Designs, PocketPro Full Swing Analysis in Your Pocket, www.PocketPro.org.
Clemson University, Golf Shot Tutorial, http://www.webnucleo.org/home/online_tools/newton/0.4/html/about_this_tool/tutorials/golf_1.shp.cgi, retrieved on Aug. 11, 2013.
miCoach SPEED_CELL TM, User Manual, 23 pages.
Nike+iPod, User Guide, 32 pages.
SureShotGPS SS9000X, Intelligent Touch, Instruction Manual, 25 pages.
ActiveReply, "TRACE—The Most Advanced Activity Monitor for Action Sports", http://www.kickstarter.com/projects/activereplay/trace-the-most-advanced-activity-monitor-for-actio, 13 pages, Jul. 31, 2013.
*Zepp Labs, Inc.* v. *Blast Motion, Inc.* Petition for Inter Partes Review of U.S. Pat. No. 8,903,521, filed on Feb. 24, 2016, as IPR2016-00672, and accompanying Declaration of Dr. Steven M. Nesbit.
*Zepp Labs, Inc.* v. *Blast Motion, Inc.* Petition for Inter Partes Review of U.S. Pat. No. 9,039,527, filed on Feb. 24, 2016, as IPR2016-00674, and accompanying Declaration of Dr. Steven M. Nesbit.
*Zepp Labs, Inc.* v. *Blast Motion, Inc.* Petition for Inter Partes Review of U.S. Pat. No. 8,941,723, filed on Feb. 24, 2016, as IPR2016-00675, and accompanying Declaration of Dr. Steven M. Nesbit.
*Zepp Labs, Inc.* v. *Blast Motion, Inc.* Petition for Inter Partes Review of U.S. Pat. No. 8,905,855, filed on Feb. 24, 2016, as IPR2016-00676, and accompanying Declaration of Dr. Steven M. Nesbit.
*Zepp Labs, Inc.* v. *Blast Motion, Inc.* Petition for Inter Partes Review of U.S. Pat. No. 8,944,928, filed on Feb. 24, 2016, as IPR2016-00677, and accompanying Declaration of Dr. Steven M. Nesbit.
Chris Otto, et al, "System Architecture of a Wireless Body Area Sensor Network for Ubiquitous Health Monitoring", *Journal of Mobile Multimedia*, vol. 1, No. 4, Jan. 10, 2006, University of Alabama in Huntsville, 20 Pages.
Linx Technologies "High Performance RF Module: Hp3 Series Transmitter Module Data Guide Description", Jul. 27, 2011, 13 pages.
Roger Allan, "Wireless Sensor Architectures Uses Bluetooth Standard", www.electronicdesign.com/communications/wireless-sensor-architecture-uses-bluetooth-standard, Aug. 7, 2000, 5 pages.
Don Tuite, "Motion-Sensing MEMS Gyros And Accelerometers are Everywhere", www.electronicdesign.com/print/analog/motion-sensing-mems-gyros-and-accelerometers-are-everywhere, Jul. 9, 2009, 6 pages.
InvenSense News Release, "InvenSense Unveils World's 1$^{st}$IMU Solution for Consumer Applications", ir.invensense.com, 2016, 2 Pages.
Dean Takahashi, "Facebook, Twitter, Last.fm coming to Xbox Live this Fall", Jun. 1, 2009, Webpage printout, 5 pages.
The iClub System, Products pages, www.iclub.net, 2001-2005, 5 pages.
Websters New College Dictionary, Definition of "Virtual Reality", Third Edition, 2005, 3 Pages.
SmartSwing, "SmartSwing Introduces Affordable Intelligent Golf Club", www.smartswinggolf.com, Jan. 2006, 2 pages.
Henrick Arfwedson, et al., "Ericsson's Bluetooth modules", Ericsson Review No. 4, 1999, 8 pages.
ZigBees, "Zigbee information", www.zigbees.com, 2015, 4 pages.
SolidState Technology, "MEMS enable smart golf clubs", www.electroiq.com, 2005, 3 pages.
IGN, "Japanese WII Price Release Date Revealed", www.ign.com, 2006, 1 page.

(56) References Cited

OTHER PUBLICATIONS

First Annual Better Golf Through Technology Conference 2006 webpage, www.bettergolfthroughtechnology.com, Massachusetts Institute of Technology, Cambridge Massachusetts, Feb. 2006, 1 page.

Concept2Rowing, "Training" web content, www.concept2.com, 2009, 1 page.

Expresso, Products pages, www.expresso.com/products, 2009, 2 pages.

Manish Kalia, et al., "Efficient Policies for Increasing Capacity in Bluetooth: An Indoor Pico-Cellular Wireless System", IBM India Research Laboratory, Indian Institute of Technology, 2000, 5 pages.

R. Rao, et al., "Demand-Based Bluetooth Scheduling", Pennsylvania State University, 2001, 13 pages.

International Search Report received in PCTUS15/61695, dated Dec. 22, 2015, 7 pages.

European Search Report received in 13738469.9 dated Jan. 21, 2016, 12 pages.

* cited by examiner

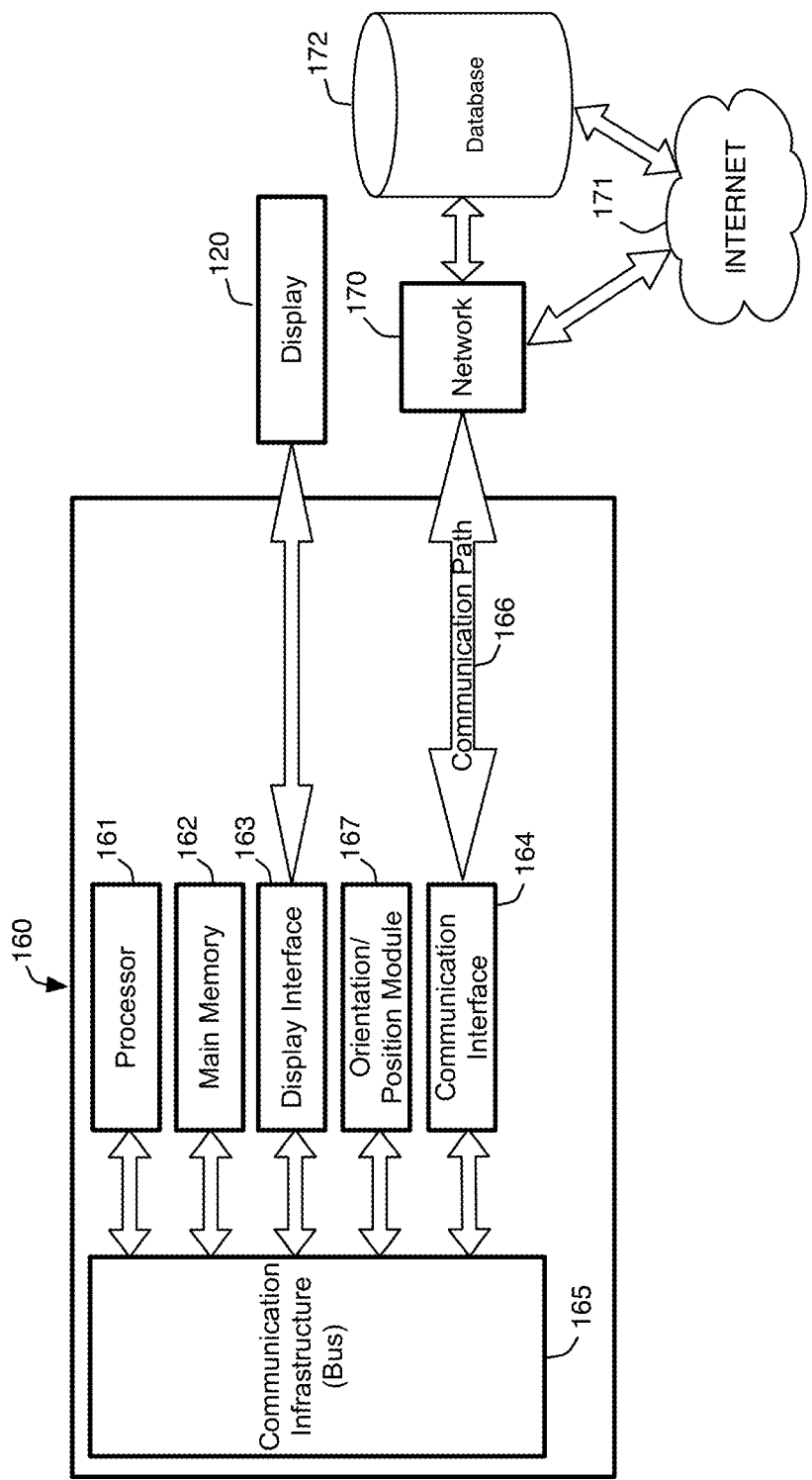

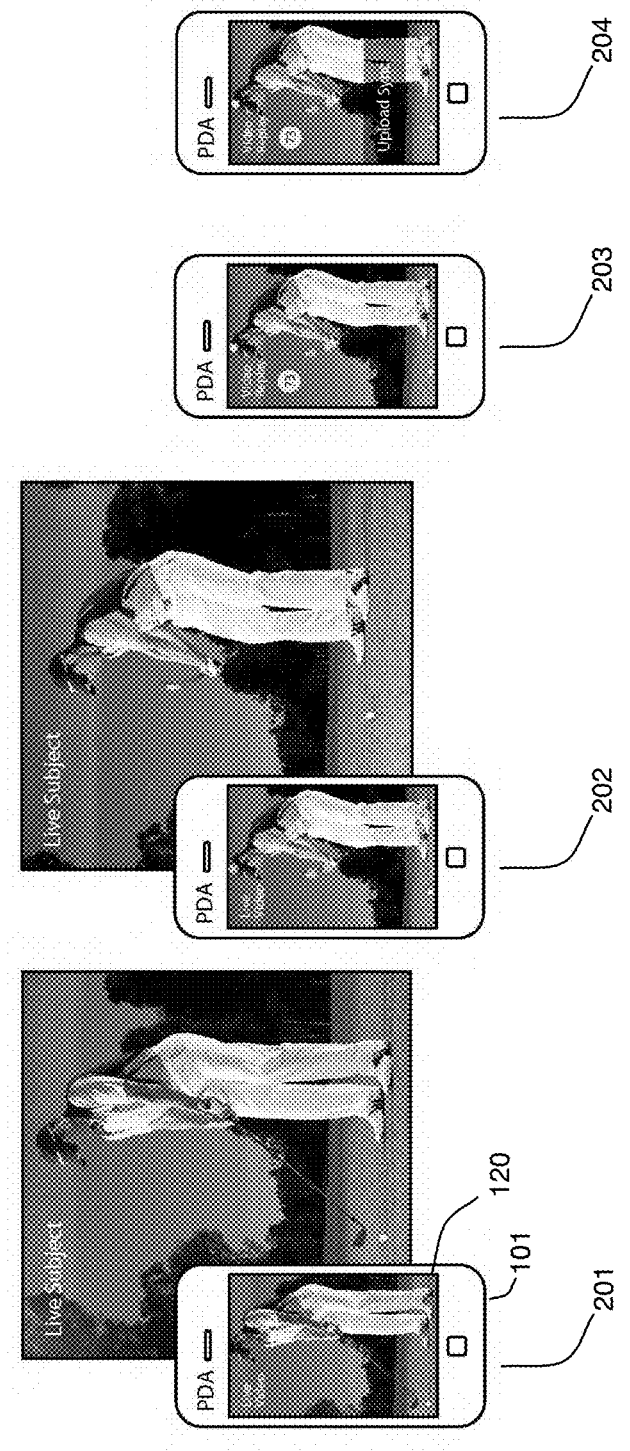

FIGURE 37

$$\ddot{x} = -Bu(C_D u_x + C_L u_y \sin(\alpha))$$

$$\ddot{y} = -Bu[C_D u_y - C_L(u_x \sin(\alpha) - u_z \cos(\alpha))]$$

$$\ddot{z} = -g - Bu(C_D u_z - C_L u_y \cos(\alpha))$$

$$C_D = \frac{46.0 ft/s}{v}$$

$$C_L = \frac{33.4 ft/s}{v}$$

3701

MOTION CAPTURE AND ANALYSIS SYSTEM

This application is a continuation of U.S. Utility patent application Ser. No. 13/219,525 filed 26 Aug. 2011, which is a continuation-in-part of U.S. Utility patent application Ser. No. 13/191,309 filed 26 Jul. 2011, which is a continuation-in-part of U.S. Utility patent application Ser. No. 13/048,850 filed 15 Mar. 2011, which is a continuation-in-part of U.S. Utility patent application Ser. No. 12/901,806 filed 11 Oct. 2010, which is a continuation-in-part of U.S. Utility patent application Ser. No. 12/868,882 filed 26 Aug. 2010, the specifications of which are hereby incorporated herein by reference.

BACKGROUND OF THE INVENTION

1. Field of the Invention

One or more embodiments setting forth the ideas described throughout this disclosure pertain to the field of portable wireless mobile device computer systems, radio frequency identification and optionally motion capture elements such as visual markers and sensors utilized in the capture of motion data. More particularly, but not by way of limitation, one or more aspects of the disclosure enable a portable wireless mobile device motion capture and analysis system and method.

2. Description of the Related Art

One known technique to teach effective body mechanics utilizes video recording of an athlete and analysis of the recorded video of an athlete. This technique has various limitations including inaccurate and inconsistent subjective analysis based on video for example. Another technique includes motion analysis, for example using at least two cameras to capture three-dimensional points of movement associated with an athlete. Known implementations utilize a stationary multi-camera system that is not portable and thus cannot be utilized outside of the environment where the system is installed, for example during an athletic event such as a golf tournament. These fixed installations are extremely expensive as well. Such prior techniques are summarized in U.S. Pat. No. 7,264,554, filed 26 Jan. 2006, which claims the benefit of U.S. Provisional Patent Application Ser. No. 60/647,751 filed 26 Jan. 2005, the specifications of which are both hereby incorporated herein by reference. Both disclosures are to the same inventor of the subject matter of the instant application.

Known systems generally utilize several passive or active markers or several sensors. There are no known systems that utilize as little as one visual marker or sensor and a mobile device to analyze and display motion capture data associated with a user and/or piece of equipment.

There are no known systems that allow for a group of mobile devices to share data to form three-dimensional motion capture data by triangulation of visual markers. There are no known systems that allow for a mobile device without a camera to obtain images from cameras or other mobile devices with cameras to display motion capture data.

There are no known mobile motion captures systems that allow for a user to align a camera correctly along the horizontal before capture of motion data having horizontally aligned images.

There are no known systems that allow for motion capture elements such as wireless sensors to seamlessly integrate or otherwise couple with a golf club, for example in the weight port of a golf club or at the end shaft near the handle so as to provide a wireless golf club, configured to capture motion data. In addition, there are no known systems that allow for motion capture elements such as wireless sensors to seamlessly integrate or couple with shoes, gloves, shirts, pants, belts, or other equipment, or a user, in such a small format that the user is not aware that the sensors are located in these items.

In addition, for sports that utilize a piece of equipment and a ball, there are no known portable wireless mobile device motion capture and analysis systems that allow the user to obtain immediate visual feedback regarding ball flight distance, swing speed, swing efficiency of the piece of equipment or how centered an impact of the ball is, i.e., where on piece of equipment the collision of the ball has taken place.

In addition, there are no known systems that provide portable wireless mobile device motion capture and analysis for equipment fitting and subsequent point-of-sale decision making for instantaneous purchasing of equipment that fits an athlete. Furthermore, no known systems allow for custom order fulfillment such as assemble-to-order (ATO) for custom order fulfillment of sporting equipment, for example equipment that is built to customer specifications based on portable wireless mobile device motion capture and analysis, and shipped to the customer to complete the point of sales process.

In addition, known systems for counting golf shots are cumbersome and require electronics on each golf club and/or switches that a user is required to operate. In addition, known devices also require active electronics, and therefore batteries in each golf club to operate. There are no known systems that allow a golfer to easily record a shot and location of a shot automatically and/or prompt a user to remember to record each shot for a particular club without a battery and active electronics on the club, for example that is not a practice shot.

For at least the limitations described above there is a need for a portable wireless mobile device motion capture and analysis system and method.

BRIEF SUMMARY OF THE INVENTION

Embodiments of the invention enable a portable wireless mobile device motion capture and analysis system and method. Utilizing this system enables a user to perform motion capture and/or display with an application for example that executes on mobile device having a visual display and an optional camera and capable of obtaining data from at least one motion capture element such as a visual marker and/or a wireless sensor. The system can also integrate with standalone cameras, or cameras on multiple mobile devices. The system also enables the user to analyze and display the motion capture data in a variety of ways that provide immediate easy to understand graphical information associated with the motion capture data. Motion capture elements utilized in the system intelligently store data for example related to events associated with striking a ball and eliminate false events. In addition, the data may be stored for example for more than one event associated with the sporting equipment, for example multiple bat swings or for an entire round of golf or more if necessary at least until the data is downloaded to a mobile device or to the Internet. Data compression of captured data may also be utilized to store more motion capture data in a given amount of memory. Motion capture elements utilized in the system may also be configured to intelligently power down portions of their circuitry to save power, for example power down transceivers until motion is detected of a certain type.

Embodiments of the invention directed at golf also enable golf shots for each club associated with a golfer to be counted through use of an identifier such as RFID tags on each club (or optionally via an identifier associated with motion capture electronics on a golf club or obtained remotely over the radio) and a mobile computer, for example an IPHONE® equipped with an RFID reader that concentrates the processing for golf shot counting on the mobile computer instead of on each golf club. Embodiments of the invention may also allow for the measurement of orientation (North/South, and/or two horizontal axes and the vertical axis) and acceleration using an inertial measurement unit, or accelerometers and/or magnetometers, and/or gyroscopes. This is not required for golf shot counting, although one or more embodiments may determine when the golf club has struck a golf ball through vibration analysis for example and then query a golfer whether to count a shot or not. This functionality may be combined with speed or acceleration threshold or range detection for example to determine whether the golf club was travelling within an acceptable speed or range, or acceleration or range for the "hit" to count. Wavelets may also be utilized to compare valid swing signatures to eliminate count shots or eliminate false strikes for example. This range may vary between different clubs, for example a driver speed range may be "greater than 30 mph" while a putter speed range may be "less than 20 mph", any range may be utilized with any club as desired, or the speed range may be ignored for example. Alternatively or in combination, the mobile computer may only query the golfer to count a shot if the golfer is not moving laterally, i.e., in a golf cart or walking, and/or wherein the golfer may have rotated or taken a shot as determined by a orientation or gyroscope sensor coupled with the mobile computer. The position of the stroke may be shown on a map on the mobile computer for example. In addition, GPS receivers with wireless radios may be placed within the tee markers and in the cups to give daily updates of distances and helps with reading putts and greens for example. The golfer may also wear virtual glasses that allow the golfer to see the golf course map, current location, distance to the hole, number of shots on the current hole, total number of shots and any other desired metric. If the user moves a certain distance, as determined by GPS for example, from the shot without counting the shot, the system may prompt the user on whether to count the shot or not. The system does not require a user to initiate a switch on a club to count a shot and does not require LED's or active or battery powered electronics on each club to count shots. The mobile computer may also accept gestures from the user to count a shot or not count a shot so that the golfer does not have to remove any gloves to operate the mobile computer. For embodiments that utilize position/orientation sensors, the system may only count shots when a club is oriented vertically for example when an impact is detected. The apparatus may also include identifiers that enable a specific apparatus to be identified. The identifiers may be a serial number for example. The identifier for example may originate from an RFID tag on each golf club, or optionally may include a serial number or other identifier associated with motion capture elements associated with a golf club. Utilizing this apparatus enables the identification of a specific golfer, specific club and also enables motion capture and/or display with a system that includes a television and/or mobile device having a visual display and an optional camera and capable of obtaining data from at least one motion capture element such as a visual marker and/or a wireless sensor. The system can also integrate with standalone cameras, or cameras on multiple mobile devices. The system also enables the user to analyze and display the motion capture data in a variety of ways that provide immediate and easy to understand graphical information associated with the motion capture data. The apparatus enables the system to also determine how "centered" an impact is with respect to a ball and a piece of equipment, such as a golf club for example. The system also allows for fitting of equipment including shoes, clubs, etc., and immediate purchasing of the equipment even if the equipment requires a custom assemble-to-order request from a vendor.

For example, embodiments that utilize motion capture elements allow for analyzing the data obtained from the apparatus and enable the presentation of unique displays associated with the user, such as 3D overlays onto images of the body of the user to visually depict the captured motion data. In addition, these embodiments may also utilize active wireless technology such as BLUETOOTH® Low Energy for a range of up to 50 meters to communicate with a golfer's mobile computer. Embodiments of the invention also allow for display of queries for counting a stroke for example as a result of receiving a golf club ID, for example via an RFID reader or alternatively via wireless communication using BLUETOOTH® or IEEE 802.11 for example. Use of BLUETOOTH® Low Energy chips allows for a club to be in sleep mode for up to 3 years with a standard coin cell battery, thus reducing required maintenance. One or more embodiments of the invention may utilize more than one radio, of more than one technology for example. This allows for a level of redundancy that increases robustness of the system. For example, if one radio no longer functions, e.g., the BLUETOOTH® radio for example, then the IEEE 802.11 radio may be utilized to transfer data and warn the golfer that one of the radios is not functioning, while still allowing the golfer to record motion data and count shots associated with the particular club. For embodiments of the invention that utilize a mobile device (or more than one mobile device) without camera(s), sensor data may be utilized to generate displays of the captured motion data, while the mobile device may optionally obtain images from other cameras or other mobile devices with cameras. For example, display types that may or may not utilize images of the user may include ratings, calculated data and time line data. Ratings associated with the captured motion can also be displayed to the user in the form of numerical or graphical data with or without a user image, for example an "efficiency" rating. Calculated data, such as a predicted ball flight path data can be calculated and displayed on the mobile device with or without utilizing images of the user's body. Data depicted on a time line can also be displayed with or without images of the user to show the relative peaks of velocity for various parts of the equipment or user's body for example. Images from multiple cameras including multiple mobile devices, for example from a crowd of golf fans, may be combined into a BULLET TIME® visual effect characterized by slow motion of the golf swing shown from around the golfer at various angles at normal speed.

Motion capture data can be tweeted to a social network during or after play. For example, if a new power factor maximum has been obtained, the system can automatically tweet the new information to a social network site so that anyone connected to the Internet may be notified. The data uploaded to the Internet, i.e., a remote database or remote server or memory remote to the system may be viewed, analyzed or data mined by any computer that may obtain access to the data. This allows for original equipment manufacturers to determine for a given user what sporting equipment is working best and/or what equipment to suggest. Data mining also enables the planning of golf courses based on the metadata associated with users, such as age, or any other demographics that may be entered into the system. Remote storage of data also enables medical applications such as morphological analysis, range of motion over time, and diabetes prevention and exercise monitoring and compliance applications.

Other applications also allow for games that use real motion capture data from other users, or historical players whether alive or dead after analyzing videos of the historical players for example. Virtual reality and augmented virtual reality applications may also utilize the motion capture data or historical motion data.

In one or more embodiments of the invention, fixed cameras such as at a golf tournament or other sporting event can be utilized with a wireless interface located near the player/equipment having motion capture elements so as to obtain, analyze and display motion capture data. In this embodiment, real-time or near real-time motion data can be displayed on the video for augmented video replays. An increase in the entertainment level is thus created by visually displaying how fast equipment is moving during a shot, for example with rings drawn around a players hips and shoulders. Embodiments of the invention also allow images or videos from other players having mobile devices to be utilized on a mobile device related to another user so that users don't have to switch mobile phones for example. In one embodiment, a video obtained by a first user for a piece of sporting equipment in motion that is not associated with the second user having the video camera equipped mobile phone may automatically transfer the video to the first user for display with motion capture data associated with the first user.

Based on the display of data, the user can determine the equipment that fits the best and immediately purchase the equipment, via the mobile device. For example, when deciding between two golf clubs, a user can take swings with different clubs and based on the analysis of the captured motion data and quantitatively determine which club performs better. Custom equipment may be ordered through an interface on the mobile device from a vendor that can assemble-to-order customer built equipment and ship the equipment to the user for example. Shaft lengths for putters for example that are a standard length can be custom made for a particular user based on captured motion data as a user putts with an adjustable length shaft for example.

Embodiments of the system may utilize a variety of sensor types. In one or more embodiments of the invention, active sensors may integrate with a system that permits passive or active visual markers to be utilized to capture motion of particular points on a user's body or equipment. This may be performed in a simply two-dimensional manner or in a three-dimensional manner if the mobile device is configured with two or more cameras, or if multiple cameras or mobile devices are utilized to capture images such as video and share the images in order to create triangulated three-dimensional motion data from a set of two-dimensional images obtained from each camera. Another embodiment of the invention may utilize inertial measurement units (IMU) or any other sensors that can produce any combination of orientation, position, velocity and/or acceleration information to the mobile device. The sensors may thus obtain data that may include any combination of one or more values associated with orientation (vertical or North/South or both), position (either via through Global Positioning System, i.e., "GPS" or through triangulation), velocity (in all three axes), acceleration (in all three axes).

In one or more embodiments of the invention, a sensor may be utilized that includes a passive marker or active marker on an outside surface of the sensor, so that the sensor may also be utilized for visual tracking (either two-dimensional or three-dimensional) and for orientation, position, velocity, acceleration or any other physical quantity produced by the sensor. Visual marker embodiments of the motion capture element(s) may be passive or active, meaning that they may either have a visual portion that is visually trackable or may include a light emitting element such as a light emitting diode (LED) that allows for image tracking in low light conditions. This for example may be implemented with a graphical symbol or colored marker at the end of the shaft near the handle or at the opposing end of the golf club at the head of the club.

The sensors utilized with embodiments of the apparatus may be generally mounted on or near one or more end or opposing ends of a golf club and may integrate with other sensors coupled to equipment, such as shoes, pants, shirts, gloves, clubs, bats, racquets, balls, etc., and/or may be attached to a user in any possible manner. For example, one or more embodiments of the sensor can fit into a weight port of a golf club, and/or in the handle end of the golf club. Other embodiments may fit into the handle of, or end of, a tennis racquet or baseball bat for example. One or more embodiments of the invention may also operate with balls that have integrated sensors as well. Alternatively, the system may calculate the virtual flight path of a ball that has come in contact with equipment moved by a player. For example with a golf club having a sensor integrated into a weight port of other portion of the end of the club striking the golf ball and having a second sensor located in the tip of the handle of the golf club, or in one or more gloves worn by the player, an angle of impact can be calculated for the club. By knowing the loft of the face of the club, an angle of flight may be calculated for the golf ball. In addition, by sampling the sensor at the end of the club at a high enough speed to determine oscillations indicative of where on the face of the club the golf ball was struck, a quality of impact may be determined. These types of measurements and the analysis thereof help an athlete improve, and for fitting purposes, allow an athlete to immediately purchase equipment that fits correctly.

One or more embodiments of the sensor may contain charging features such as mechanical eccentric weight, as utilized in some watches known as "automatic" or "self-winding" watches, optionally including a small generator, or inductive charging coils for indirect electromechanical charging of the sensor power supply. Other embodiments may utilize plugs for direct charging of the sensor power supply or electromechanical or microelectromechanical (MEMS) based charging elements. Any other type of power micro-harvesting technologies may be utilized in one or more embodiments of the invention. One or more embodiments of the sensor may utilize power saving features including gestures that power the sensor on or off. Such gestures may include motion, physical switches, contact with the sensor, wireless commands to the sensor, for example from a mobile device that is associated with the particular sensors. Other elements that may couple with the sensor includes a battery, low power microcontroller, antenna and radio, heat sync, recharger and overcharge sensor for example. In addition, embodiments of the invention allow for power down of some or all of the components of the system until an electronic signal from accelerometers or a mechanical switch determines that the club has moved for example.

A user may also view the captured motion data in a graphical form on the display of the mobile device or for example on a set of glasses that contains a video display. The captured motion data obtained from embodiments of the motion capture element may also be utilized to augment a virtual reality display of user in a virtual environment.

BRIEF DESCRIPTION OF THE DRAWINGS

The above and other aspects, features and advantages of the ideas conveyed through this disclosure will be more apparent from the following more particular description thereof, presented in conjunction with the following drawings wherein:

FIG. 1A shows a hardware block diagram of an embodiment of the computer.

FIG. 2 illustrates an embodiment of the overall modes of the software programmed to execute on the computer of the mobile device, wherein the computer is configured to recognize the motion capture elements, obtain data, analyze the data and display motion analysis data.

FIG. 37 illustrates one embodiment of the equations used for predicting a golf ball flight path as used to produce displays as shown in FIGS. 27 and 28.

DETAILED DESCRIPTION OF THE INVENTION

A portable wireless mobile device motion capture and analysis system and method will now be described. In the following exemplary description numerous specific details are set forth in order to provide a more thorough understanding of the ideas described throughout this specification. It will be apparent, however, to an artisan of ordinary skill that embodiments of ideas described herein may be practiced without incorporating all aspects of the specific details described herein. In other instances, specific aspects well known to those of ordinary skill in the art have not been described in detail so as not to obscure the disclosure. Readers should note that although examples of the innovative concepts are set forth throughout this disclosure, the claims, and the full scope of any equivalents, are what define the invention.

Figure 1:
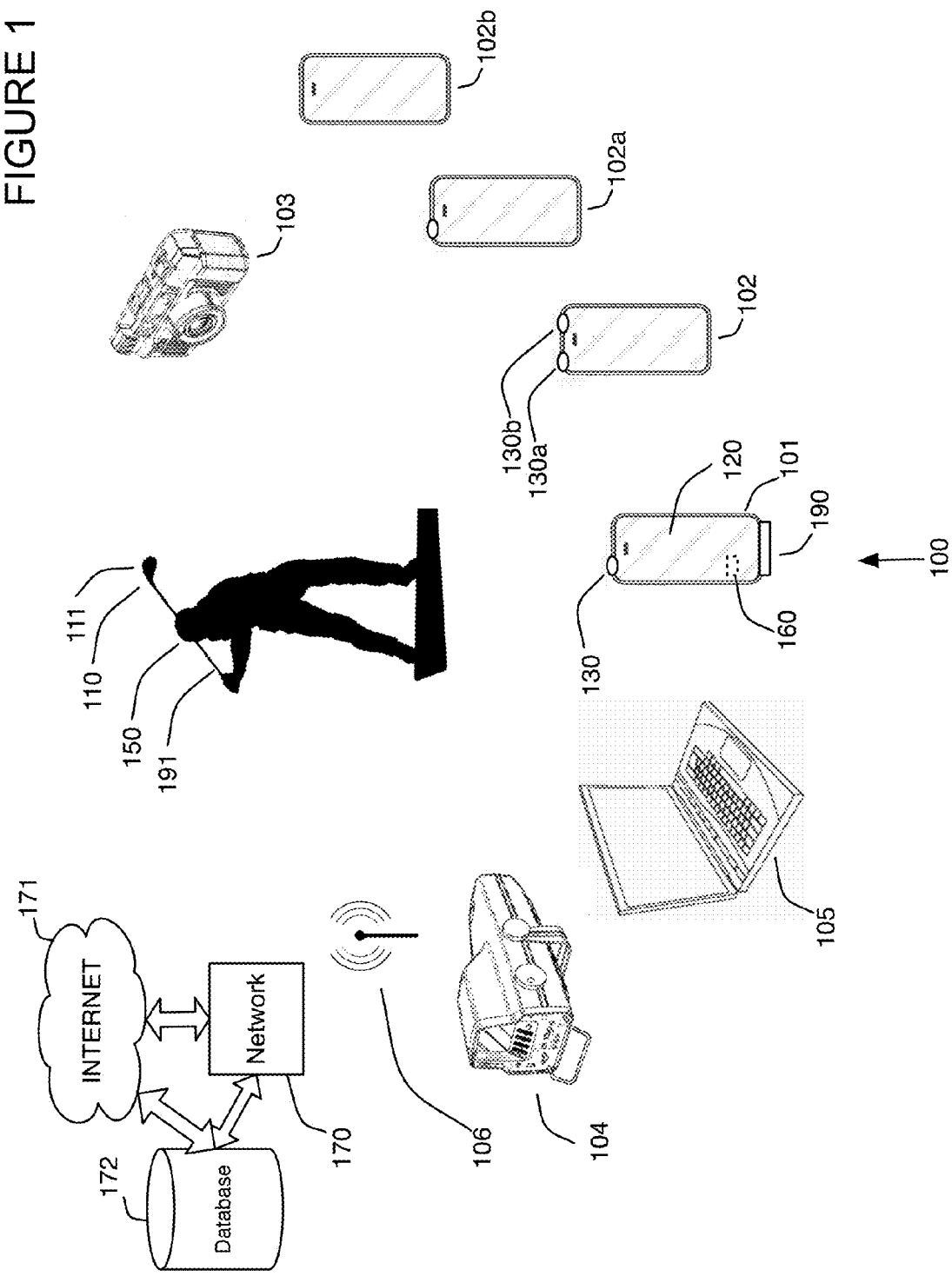
FIG. 1 illustrates an embodiment of the system that enables a portable wireless mobile device motion capture and analysis system.

FIG. 1 illustrates an embodiment of the system that enables a portable wireless mobile device motion capture and analysis system 100. As shown, embodiments of the system generally include a mobile device 101 and applications that execute thereon, that includes computer 160, shown as located internally in mobile device 101 as a dotted outline, (i.e., also see functional view of computer 160 in FIG. 1A), display 120 coupled to computer 160 and a wireless communications interface (generally internal to the mobile device, see element 164 in FIG. 1A) coupled with the computer. Each mobile device 101, 102, 102a, 102b may have an internal identifier reader 190, for example an RFID reader, or may couple with an identifier reader or RFID reader (see mobile device 102). Alternatively, embodiments of the invention may utilize any wireless technology in any of the devices to communicate an identifier that identifies the club to the system. The system generally includes at least one motion capture element 111 that couples with user 150 or with piece of equipment 110, for example a golf club, or baseball bat, tennis racquet, hockey stick, weapon, stick, sword, or any other piece of equipment for any sport, or other sporting equipment such as a shoe, belt, gloves, glasses, hat, etc. The motion capture element may optionally include a visual marker, either passive or active, and/or may include a wireless sensor, for example any sensor capable of providing any combination of one or more values associated with an orientation (North/South and/or up/down), position, velocity and/or acceleration of the motion capture element. The computer may be configured to obtain data associated with an identifier unique to each club 110, for example from an RFID coupled with club 110, i.e., identifier 191, and optionally associated with the at least one motion capture element, either visually or wirelessly, analyze the data to form motion analysis data and display the motion analysis data on display 120 of mobile device 101.

One or more embodiments of the system may utilize a mobile device that includes at least one camera 130, for example coupled to the computer within the mobile device. This allows for the computer within mobile device 101 to command the camera 130 to obtain an image or images, for example of the user during an athletic movement. The image(s) of the user may be overlaid with displays and ratings to make the motion analysis data more understandable to a human for example. Alternatively, detailed data displays without images of the user may also be displayed on display 120 or for example on the display of computer 105. In this manner two-dimensional images and subsequent display thereof is enabled. If mobile device 101 contains two cameras, as shown in mobile device 102, i.e., cameras 130a and 130b, then the cameras may be utilized to create a three-dimensional data set through image analysis of the visual markers for example. This allows for distances and positions of visual markers to be ascertained and analyzed.

Alternatively, for embodiments of mobile devices that have only one camera, multiple mobile devices may be utilized to obtain two-dimensional data in the form of images that is triangulated to determine the positions of visual markers. In one or more embodiments of the system, mobile device 101 and mobile device 102a share image data of user 150 to create three-dimensional motion analysis data. By determining the positions of mobile devices 101 and 102 (via position determination elements such as GPS chips in the devices as is common, or via cell tower triangulation and which are not shown for brevity but are generally located internally in mobile devices just as computer 160 is), and by obtaining data from motion capture element 111 for example locations of pixels in the images where the visual markers are in each image, distances and hence speeds are readily obtained as one skilled in the art will recognize.

Camera 103 may also be utilized either for still images or as is now common, for video. In embodiments of the system that utilize external cameras, any method of obtaining data from the external camera is in keeping with the spirit of the system including wireless communication of the data, or via wired communication as when camera 103 is docked with computer 105 for example, which then may transfer the data to mobile device 101.

In one or more embodiments of the system, the mobile device on which the motion analysis data is displayed is not required to have a camera, i.e., mobile device 102b may display data even though it is not configured with a camera. As such, mobile device 102b may obtain images from any combination of cameras on mobile device 101, 102, 102a, camera 103 and/or television camera 104 so long as any external camera may communicate images to mobile device 102b.

For television broadcasts, motion capture element 111 wirelessly transmits data that is received by antenna 106. The wireless sensor data thus obtained from motion capture element 111 is combined with the images obtained from television camera 104 to produce displays with augmented motion analysis data that can be broadcast to televisions, computers such as computer 105, mobile devices 101, 102, 102a, 102b or any other device configured to display images. The motion analysis data can be positioned on display 120 for example by knowing the location of a camera (for example via GPS information), and by knowing the direction and/or orientation that the camera is pointing so long as the sensor data includes location data (for example GPS information). In other embodiments, visual markers or image processing may be utilized to lock the motion analysis data to the image, e.g., the golf club head can be tracked in the images and the corresponding high, middle and low position of the club can be utilized to determine the orientation of user 150 to camera 130 or 104 or 103 for example to correctly plot the augmented data onto the image of user 150. By time stamping images and time stamping motion capture data, for example after synchronizing the timer in the microcontroller with the timer on the mobile device and then scanning the images for visual markers or sporting equipment at various positions, simplified motion capture data may be overlaid onto the images. Any other method of combining images from a camera and motion capture data may be utilized in one or more embodiments of the invention. Any other algorithm for properly positioning the motion analysis data on display 120 with respect to a user (or any other display such as on computer 105) may be utilized in keeping with the spirit of the system.

One such display that may be generated and displayed on mobile device 101 include a BULLET TIME® view using two or more cameras selected from mobile devices 101, 102, 102a, camera 103, and/or television camera 104 or any other external camera. In this embodiment of the system, the computer is configured to obtain two or more images of user 150 and data associated with the at least one motion capture element (whether a visual marker or wireless sensor), wherein the two or more images are obtained from two or more cameras and wherein the computer is configured to generate a display that shows slow motion of user 150 shown from around the user at various angles at normal speed. Such an embodiment for example allows a group of fans to create their own BULLET TIME® shot of a golf pro at a tournament for example. The shots may be sent to computer 105 and any image processing required may be performed on computer 105 and broadcast to a television audience for example. In other embodiments of the system, the users of the various mobile devices share their own set of images, and or upload their shots to a website for later viewing for example. Embodiments of the invention also allow images or videos from other players having mobile devices to be utilized on a mobile device related to another user so that users don't have to switch mobile phones for example. In one embodiment, a video obtained by a first user for a piece of sporting equipment in motion that is not associated with the second user having the video camera mobile phone may automatically transfer the video to the first user for display with motion capture data associated with the first user.

FIG. 1A shows an embodiment of computer 160. In computer 160 includes processor 161 that executes software modules, commonly also known as applications, generally stored as computer program instructions within main memory 162. Display interface 163 drives display 120 of mobile device 101 as shown in FIG. 1. Optional orientation/position module 167 may include a North/South or up/down orientation chip or both. Communication interface 164 may include wireless or wired communications hardware protocol chips and/or an RFID reader or an RFID reader may couple to computer 160 externally or in any other manner for example. In one or more embodiments of the system communication interface may include telephonic and/or data communications hardware. In one or more embodiments communication interface 164 may include a Wi-Fi™ or other IEEE 802.11 device and/or BLUETOOTH® wireless communications interface or ZigBee® wireless device or any other wireless technology. BLUETOOTH® class 1 devices have a range of approximately 100 meters, class 2 devices have a range of approximately 10 meters. BLUETOOTH® Low Power devices have a range of approximately 50 meters. Any wireless network protocol or type may be utilized in embodiments of the system so long as mobile device 101 and motion capture element 111 can communicate with one another. Processor 161, main memory 162, display interface 163, communication interface 164 and orientation/position module 167 may communicate with one another over communication infrastructure 165, which is commonly known as a "bus". Communications path 166 may include wired or wireless medium that allows for communication with other wired or wireless devices over network 170. Network 170 may communicate with Internet 171 and/or database 172. Database 172 may be utilized to save or retrieve images or videos of users, or motion analysis data, or users displayed with motion analysis data in one form or another. The data uploaded to the Internet, i.e., a remote database or remote server or memory remote to the system may be viewed, analyzed or data mined by any computer that may obtain access to the data. This allows for original equipment manufacturers to determine for a given user what sporting equipment is working best and/or what equipment to suggest. Data mining also enables the planning of golf courses based on the metadata associated with users, such as age, or any other demographics that may be entered into the system. Remote storage of data also enables medical applications such as morphological analysis, range of motion over time, and diabetes prevention and exercise monitoring and compliance applications. Data mining based applications also allow for games that use real motion capture data from other users, or historical players whether alive or dead after analyzing videos of the historical players for example. Virtual reality and augmented virtual reality applications may also utilize the motion capture data or historical motion data. The system also enables uploading of performance related events and/or motion capture data to database 172, which for example may be implemented as a social networking site. This allows for the user to "tweet" high scores, or other metrics during or after play to notify everyone on the Internet of the new event.

To ensure that analysis of user 150 during a motion capture includes images that are relatively associated with the horizon, i.e., not tilted, the system may include an orientation module that executes on computer 160 within mobile device 101 for example. The computer is configured to prompt a user to align the camera along a horizontal plane based on orientation data obtained from orientation hardware within mobile device 101. Orientation hardware is common on mobile devices as one skilled in the art will appreciate. This allows the image so captured to remain relatively level with respect to the horizontal plane. The orientation module may also prompt the user to move the camera toward or away from the user, or zoom in or out to the user to place the user within a graphical "fit box", to somewhat normalize the size of the user to be captured.

Embodiments of the system are further configured to recognize the at least one motion capture element associated with user 150 or piece of equipment 110 and associate at least one motion capture element 111 with assigned locations on user 150 or piece of equipment 110. For example, the user can shake a particular motion capture element when prompted by the computer within mobile device 101 to acknowledge which motion capture element the computer is requesting an identity for.

One or more embodiments of the computer in mobile device 101 is configured to obtain at least one image of user 150 and display a three-dimensional overlay onto the at least one image of user 150 wherein the three-dimensional overlay is associated with the motion analysis data. Various displays may be displayed on display 120. The display of motion analysis data may include a rating associated with the motion analysis data, and/or a display of a calculated ball flight path associated with the motion analysis data and/or a display of a time line showing points in time along a time axis where peak values associated with the motion analysis data occur and/or a suggest training regimen to aid the user in improving mechanics of the user.

Embodiments of the system may also present an interface to enable user 150 to purchase piece of equipment 110 over the wireless interface of mobile device 101, for example via the Internet, or via computer 105 which may be implemented as a server of a vendor. In addition, for custom fitting equipment, such as putter shaft lengths, or any other custom sizing of any type of equipment, embodiments of the system may present an interface to enable user 150 to order a customer fitted piece of equipment over the wireless interface of mobile device 101.

Embodiments of the system are configured to analyze the data obtained from at least one motion capture element and determine how centered a collision between a ball and the piece of equipment is based on oscillations of the at least one motion capture element coupled with the piece of equipment and display an impact location based on the motion analysis data.

While FIG. 1A depicts a physical device, the scope of the systems and methods set forth herein may also encompass a virtual device, virtual machine or simulator embodied in one or more computer programs executing on a computer or computer system and acting or providing a computer system environment compatible with the methods and processes implementing the disclosed ideas. Where a virtual machine, process, device or otherwise performs substantially similarly to that of a physical computer system of the system, such a virtual platform will also fall within the scope of a system of the disclosure, notwithstanding the description herein of a physical system such as that in FIG. 1A.

Although system 100 is shown with an exemplary user 150 playing golf, one skilled in the art will appreciate that any user in moving in any way and/or playing any sport using any piece of equipment may utilize embodiments of the invention.

FIG. 2 illustrates an embodiment of the overall modes of the software programmed to execute on the computer of the mobile device, wherein the computer is configured to optionally recognize the motion capture elements, obtain data, analyze the data and display motion analysis data. Mode 201 shows mobile device 101 having display 120 that displays a user with highlighted points on the user and/or piece of equipment. In this mode, each sensor is identified and assigned one by one to a particular area of the user or piece of equipment so as to recognize which sensors correspond to which movements of the user and/or piece of equipment. Mode 202 is the mode where the computer in mobile device obtains data associated with at least one motion capture element as recognized in mode 201. Mode 203 is the mode where the data is analyzed to form motion analysis data and display the motion analysis data optionally in conjunction with at least one image of the user. Mode 204 is the mode where the motion analysis data and optional at least one image of the user is saved, or retrieved to display at a later time. The images may be automatically captured from a second user's mobile device and transferred to the user's mobile device who swung the golf club so that they user's don't have to switch phones while playing to obtain image data for themselves. One algorithm embodiment detects a motion capture element data for a club that is not associated with the user of the video camera based mobile phone and queries nearby mobile devices to determine if they will accept the video. The mobile device of the user who performed the swing may automatically transfer the video so that after the user has swung, the user can look at their own phone and see their image overlaid with motion capture data without having users switch phones to capture video for each other. The motion capture data may be automatically store in database 172 which for example may be in the form of a social network, in which case the transfer of data (for example a new maximum power score), may be automatically "tweeted" to Internet 171 and/or database 172 to notify everyone connect to the Internet of the new event.

Figure 3:
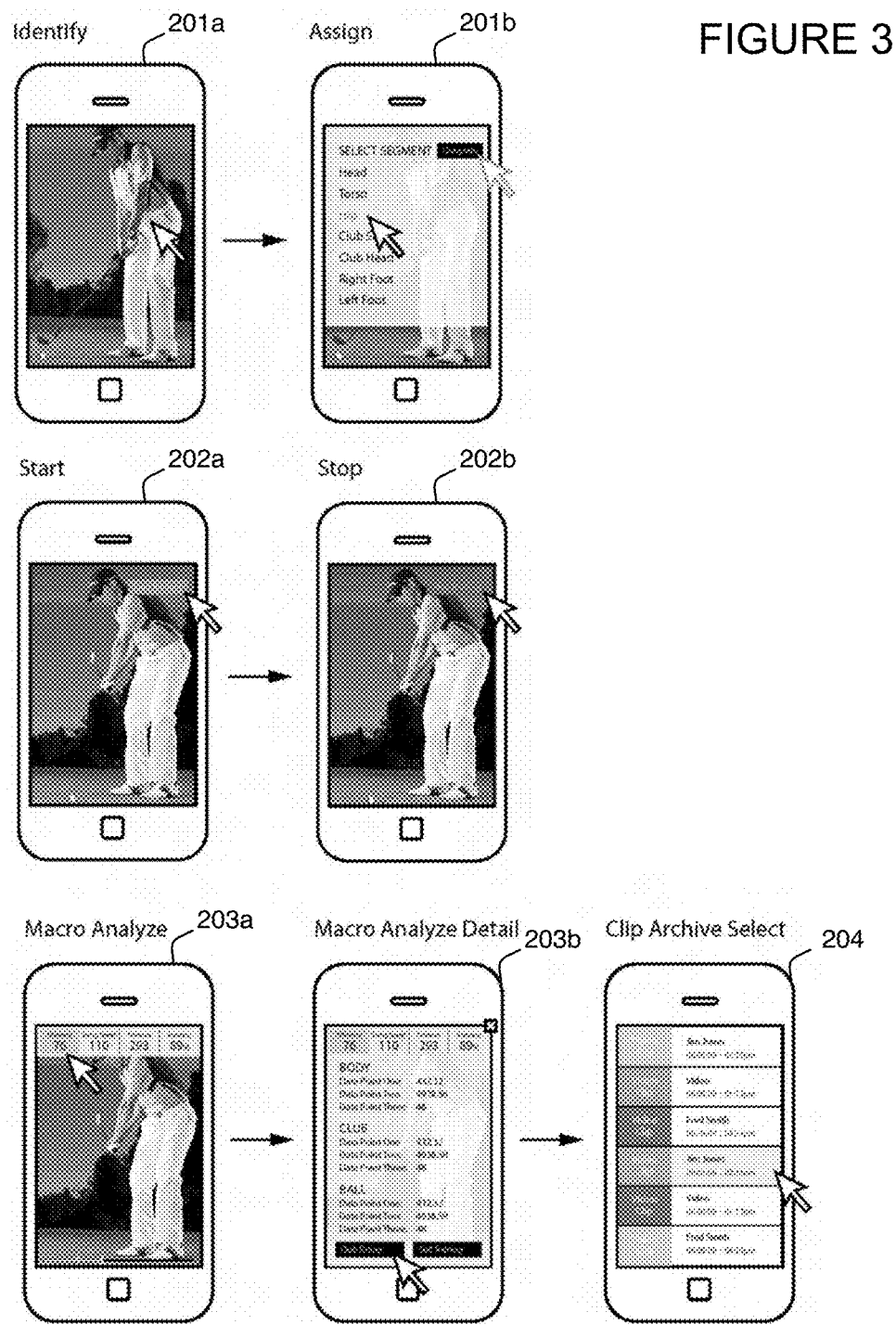
FIG. 3 illustrates displays associated with FIG. 2 in greater detail.

FIG. 3 illustrates displays associated with FIG. 2 in greater detail. Mode 201 includes sub-modes 201a where each motion capture element is asserted, moved, switched on or other wise identified. Metadata associated with the user such as age, height, weight, equipment manufacturer or model number and size may also be input in this screen. This allows for data mining the metadata and associated motion capture data later. Owners of database 172 may charge a fee for this service. Sub-mode 201b allows for assignment of the motion capture element so asserted to a particular body part of the user, or a location on the piece of equipment. Mode 202 includes sub-modes 202a where the computer obtains data associated with at least one motion capture element, either via image capture of one or more motion capture elements implemented as visual markers, or via wireless sensors, or both visual markers and wireless sensors. Mode 203 includes sub-mode 203a where main motion analysis data items may be displayed, and sub-mode 203b where detailed motion analysis data items may be displayed. Mode 204 shows selection of an archive name to store archive motion capture data, i.e., the motion analysis data and any images of the user. Mode 204 also allows for retrieval of an archived motion capture data by selected a list item on the display of the mobile device. In one or more embodiments, the motion capture archived data may be stored on the mobile device or remotely on computer 105, or in database 172 accessed via network 170 and/or via Internet 171.

Figure 4:
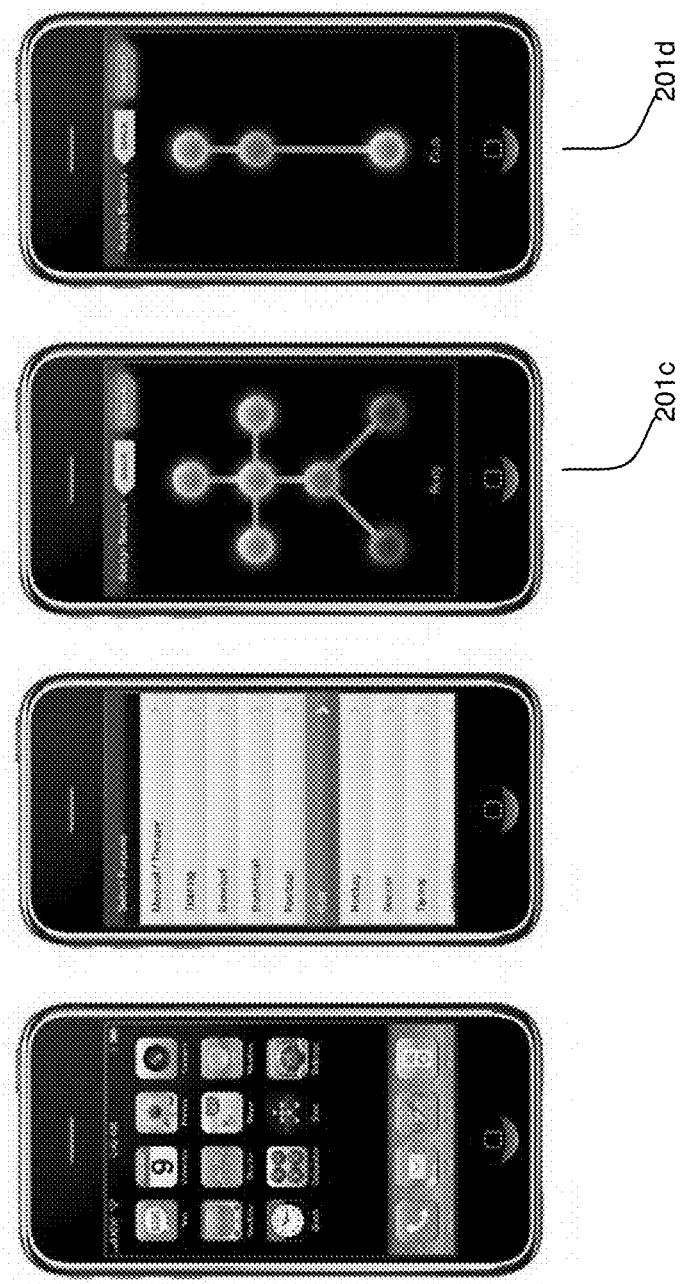
FIG. 4 illustrates and embodiment of the recognition module that is configured to assign particular sensors to particular locations on an athlete and/or on a piece of equipment.

FIG. 4 illustrates and embodiment of the recognition module that is configured to assign particular sensors to particular locations on an athlete and/or on a piece of equipment. In this simplified interface for mode 201, a mobile application is selected from the interface in the far left screen shot that then displays a number of activities or sports that can be motion captured by embodiments of the system. Selecting the desired sport via a finger gesture or any other manner in this display shows sub-mode screen 201c that allows for the assignment of sensors to areas of the user's body, and/or sub-mode screen 201d that allows for the assignment of sensors to areas on the equipment for the particular sport selected in the second screen from the left in the figure. Automatic determination of the assigned sensor locations is also possible based on analyzing the spatial data obtain from a golf swing. For example by determining the positions, or speed of the various sensors, an automatic assignment may be made, for example by taking the fastest moving component and assigning that to the golf club head, while taking the next fastest component and assigning that component to the hands, etc. Any other technique for automatically assigning sensors to locations of embodiments of the invention is in keeping with the spirit of the invention. In embodiments of the invention that utilize RFID or other identifier mechanism coupled with the golf club, such as a unique identifier per motion capture element for example, the user may enter a golf club number associated with a particular golf club so that the system knows which club is in proximity to the mobile computer or which golf club number for example has been moved through a golf swing.

Figure 5:
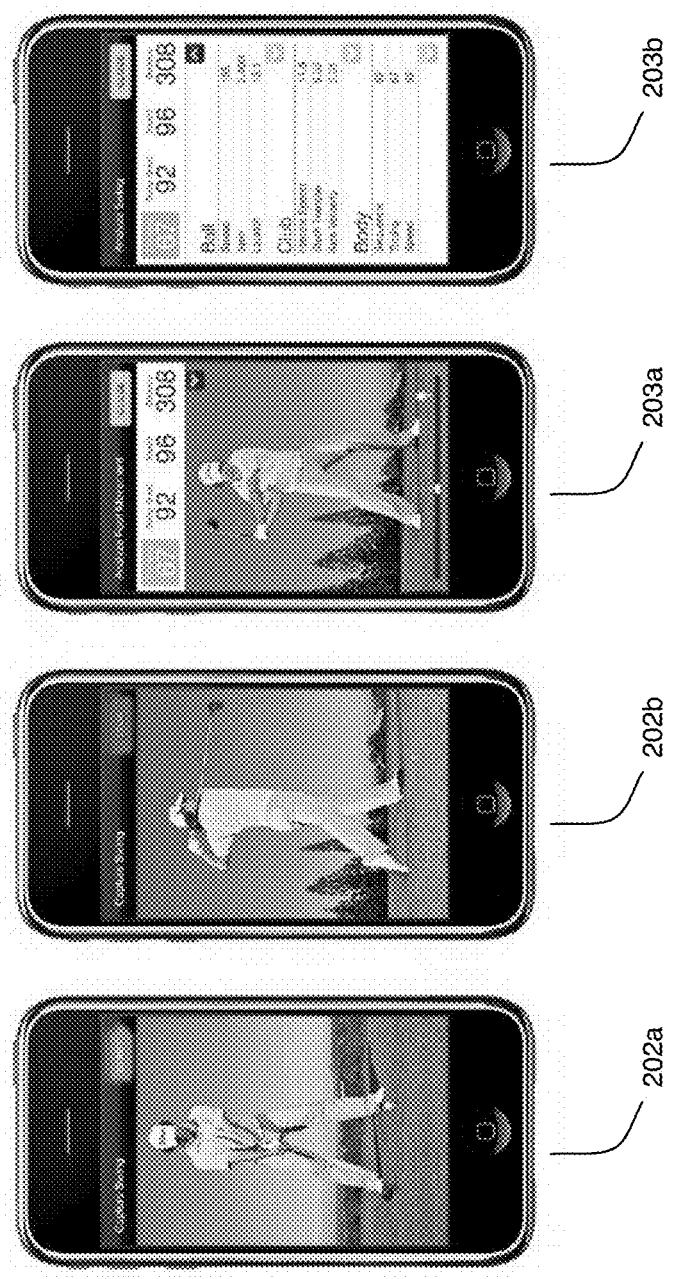
FIG. 5 illustrates an embodiment of the obtain data module that is configure to obtain data from a camera (optionally on the mobile device or obtain through another camera or camera on another mobile device), data from motion capture elements, i.e., any combination of visual markers or sensors as assigned to particular portions of the user's body or piece of equipment. In addition, the figure shows displays data analyzed by the analysis module and generated by the display module to show either the user along with motion analysis data, or with motion analysis data alone.

FIG. 5 illustrates an embodiment of the obtain data module that is configure to obtain data from a camera (optionally on the mobile device or obtain through another camera or camera on another mobile device) through asserting the "start" button on the display. Any other method of initiating the computer within the mobile device to obtain data is in keeping with the spirit of the system including user gestures such as moving the piece of equipment in a particular manner or in any other way. This is shown as sub-mode 202a. When motion data capture is to be terminated, any user gesture may be performed via the display of the mobile device, via the piece of equipment or via audio input to the mobile device for example. Any other method of informing the computer to no longer obtain data is in keeping with the spirit of the system. Sub-mode 203a where main motion analysis data items may be displayed, and sub-mode 203b where detailed motion analysis data items may be displayed are shown with "close" buttons, so that the data can be ignored for example. In addition, a slider in sub-mode 203a allows for precise control of the speed and/or location of the playback so that slow motion analysis may be utilized to better understand the analysis and display of motion analysis data. In addition, the figure shows displays data analyzed by the analysis module and generated by the display module to show either the user along with motion analysis data, or with motion analysis data alone. Double clicking or tapping on a detailed item may optionally display a list of exercises that a user may perform to increase the user's performance.

Figure 6:
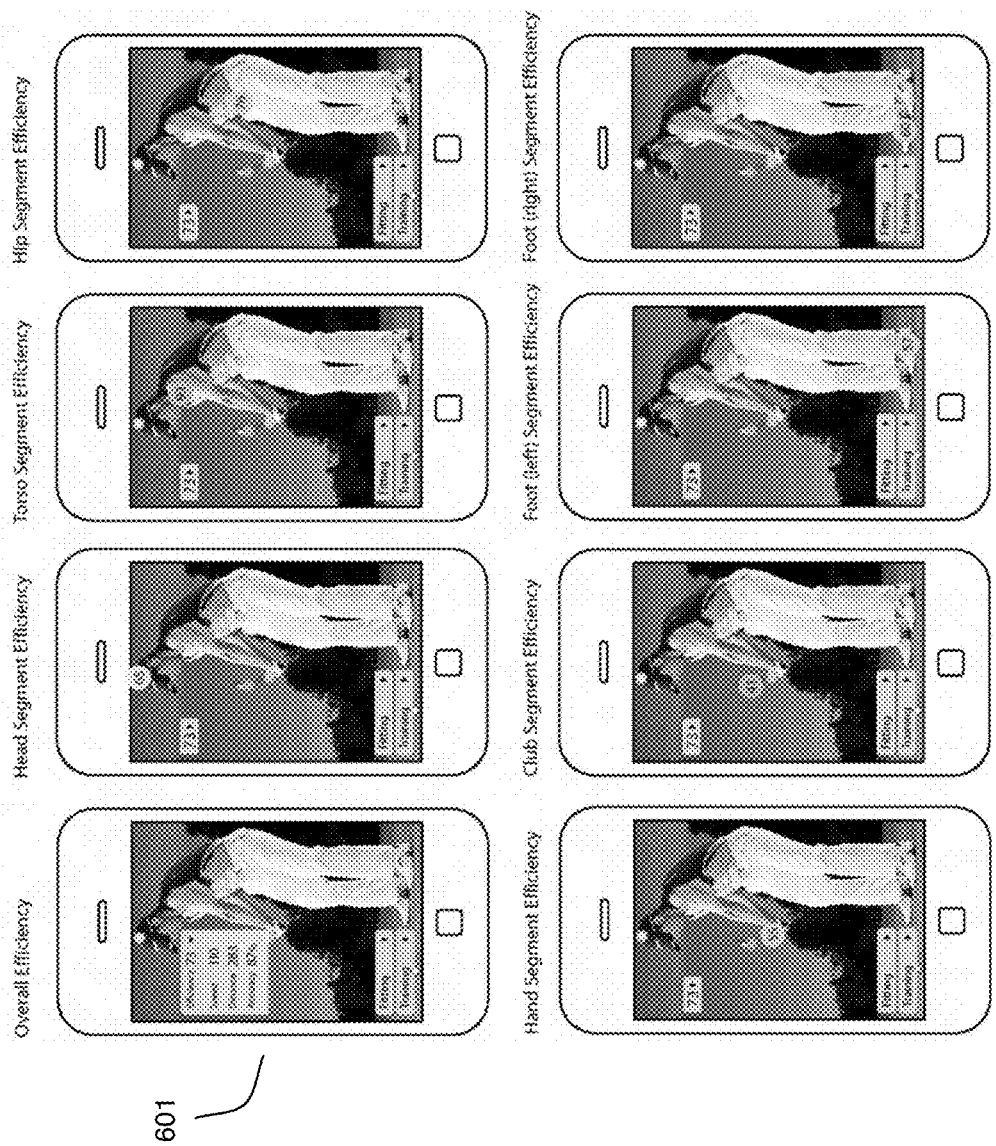
FIG. 6 illustrates a detailed drill down into the motion analysis data to display including overall efficiency, head, torso, hip, hand, club, left and right foot segment efficiencies. Embodiments of the invention thus enable physical training specific to the area that a user needs as determined by the analysis module.

FIG. 6 illustrates a detailed drill down into the motion analysis data to display including overall efficiency, head, torso, hip, hand, club, left and right foot segment efficiencies. Embodiments of the system thus enable physical training specific to the area that a user needs as determined by the analysis module. For example, asserting, double clicking or tapping, or clicking on the "training" button on the bottom of each efficiency screen as shown may display video, audio, or a list of exercises that a user may perform to increase the user's performance specific to that segment. In addition, by asserting the "fitting" button on each segment display, a detailed list of pieces of equipment that may perform better for the user based on the motion analysis data may be viewed. For example, if the user is swing too stiff of a golf club, then the golf club may be taking power out of the swing by slowing down before impacting a golf ball, while a more flexible shaft would speed up before impacting a golf ball. By asserting the "fitting" button, and based on the motion analysis data, for example club head speed or if multiple sensors are fitted on the shaft, then by the flexing of the shaft, then alternate golf clubs may be displayed to the user. The user may then press the purchase button, as will be detailed later, to purchase or custom order equipment that is better suited to the user.

Figure 7:
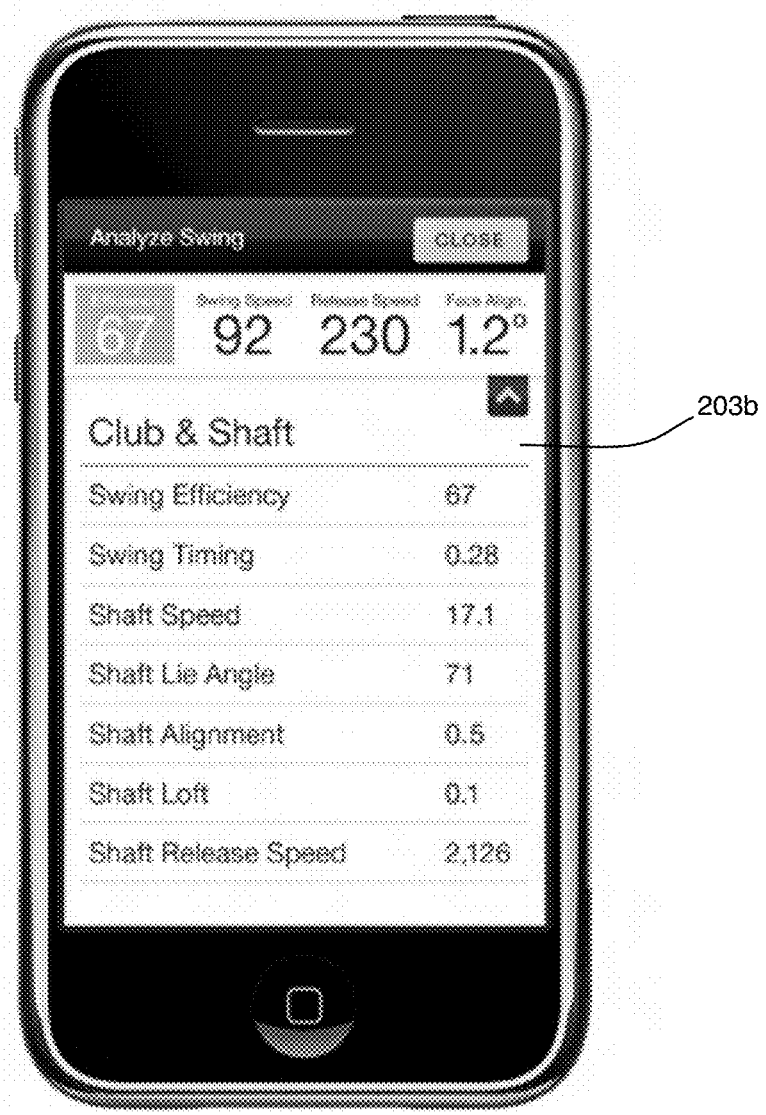
FIG. 7 illustrates a close up display of motion analysis data associated with a user, without use of an image associated with a user.

FIG. 7 illustrates a close up display of motion analysis data associated with a user, without use of an image associated with a user. In this close-up of sub-mode 203b, the efficiency, swing speed, release speed, face alignment angle and other quantities associated with the motion analysis data are displayed. Any data that is obtained or that can be analyzed and derived may be displayed.

Figure 8:
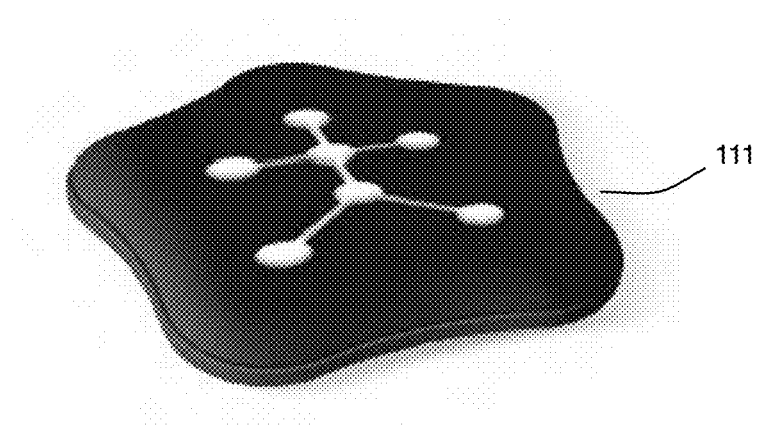
FIG. 8 illustrates an embodiment of the motion capture element that optionally includes a visual marker and/or sensor.

FIG. 8 illustrates an embodiment of the motion capture element that optionally includes a visual marker and/or sensor. One or more embodiments of the sensors are small, for example 12 mm or less in diameter and 4 mm or less thick in one embodiment. In addition, the sensors are inexpensive, lightweight, for example less than 5 grams in one or more embodiments. The sensors may utilize known wireless communications protocols such as BLUETOOTH™ with a range of approximately 10 meters for Bluetooth class 2, or 100 meters for Bluetooth class 1. Embodiments of the sensor may sample at 1200 times per second or higher or lower depending on the desired performance requirements. The sensors may be sealed for water resistance or proofing and while some embodiments may be opened, for example to replace a battery held inside the sensor housing. Any other sensor having dimensions or capabilities that allow for measurement of any combination of one or more of orientation, position, velocity and/or acceleration that may couple to a piece of equipment or user may be utilized in one or more embodiments as a motion capture element.

Figure 9:
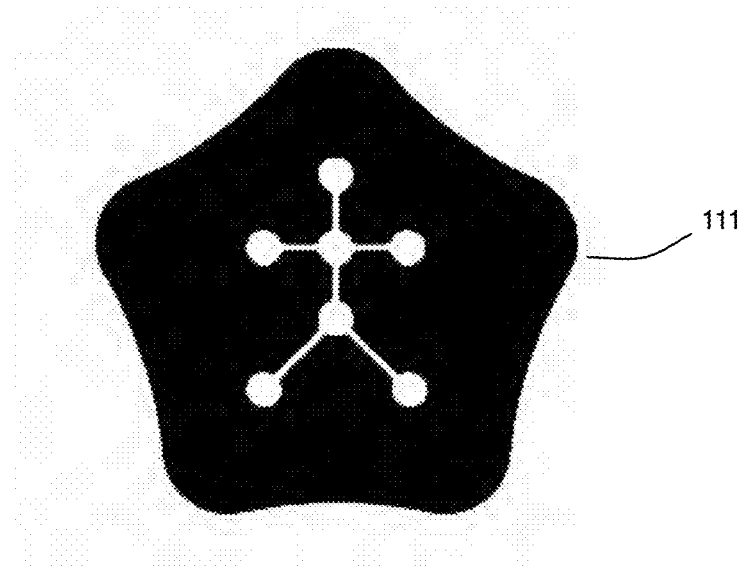
FIG. 9 illustrates a front view of FIG. 8.

FIG. 9 illustrates a front view of FIG. 8. In this figure, the visual marker is shown from above and signifies an instrumented user. The contrast between black and white allows for ease of capture.

Figure 10:
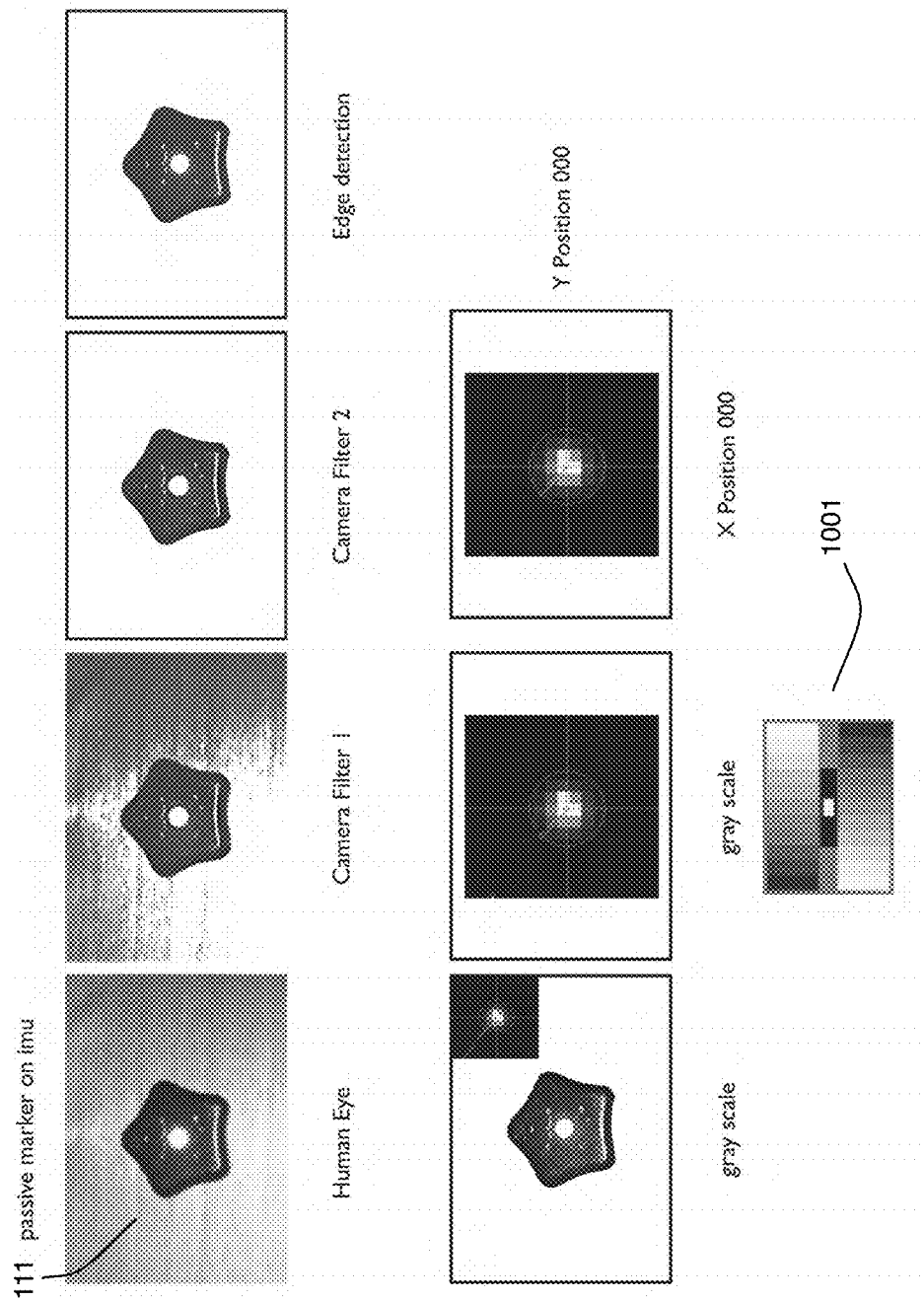
FIG. 10 illustrates an embodiment of the motion capture element implemented with a passive marker and gray scale images thereof to show how the marker can be tracked by obtaining an image and searching for a luminance change from black to white.

FIG. 10 illustrates an embodiment of motion capture element 111 implemented with a single white circle on a black passive marker and gray scale images thereof to show how the marker can be tracked by obtaining an image and searching for a luminance change from black to white as shown at point 1001. Any other image processing algorithm may be utilized to find an embodiment of the motion capture element within an image as one skilled in the art will recognize, for example based on a color difference or gradient detected in an image in the area of an embodiment of motion capture element 111.

Figure 11:
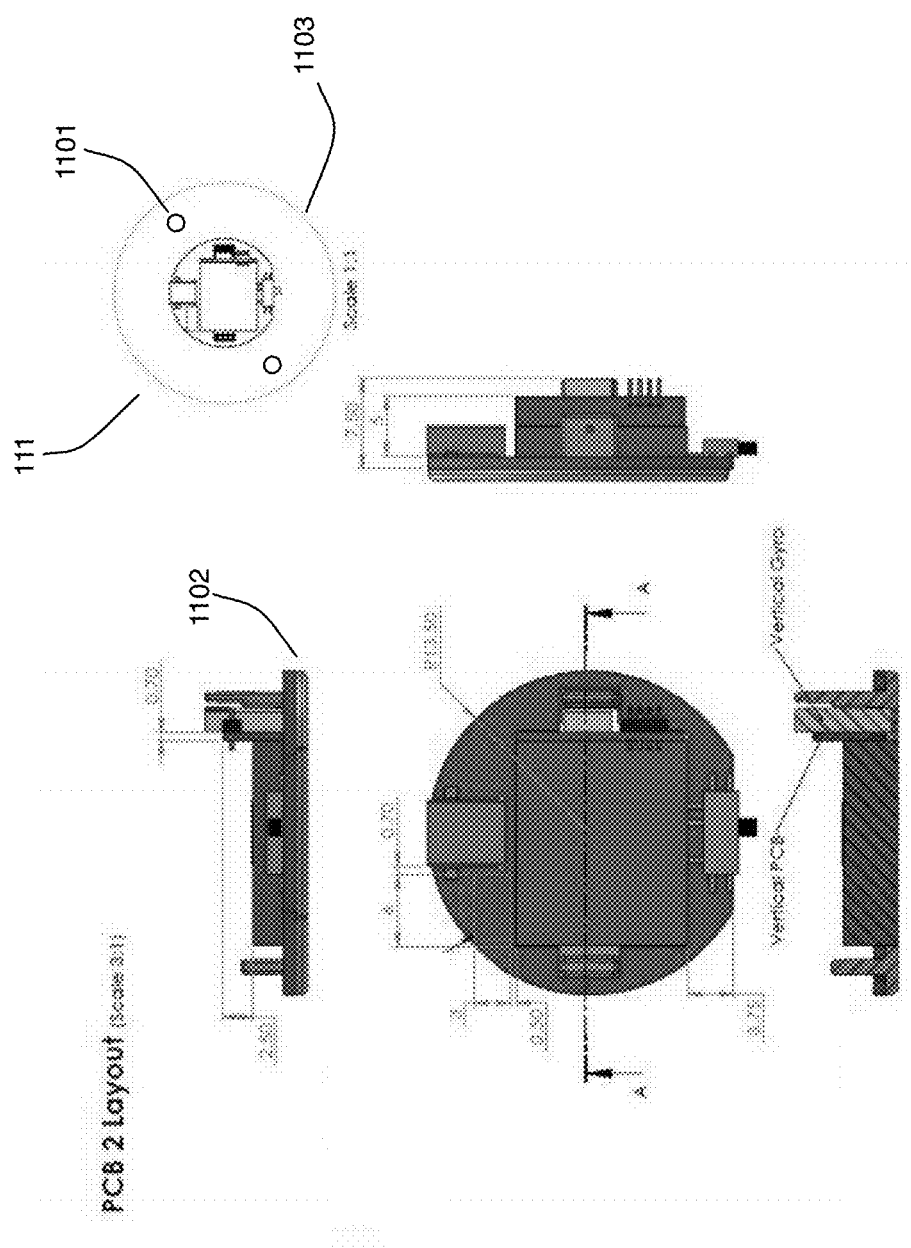
FIG. 11 illustrates a hardware implementation of the sensor portion of a motion capture element implemented as a wireless inertial measurement unit, and an embodiment as configured to couple with a weight port of a golf club for example.
Figure 38:
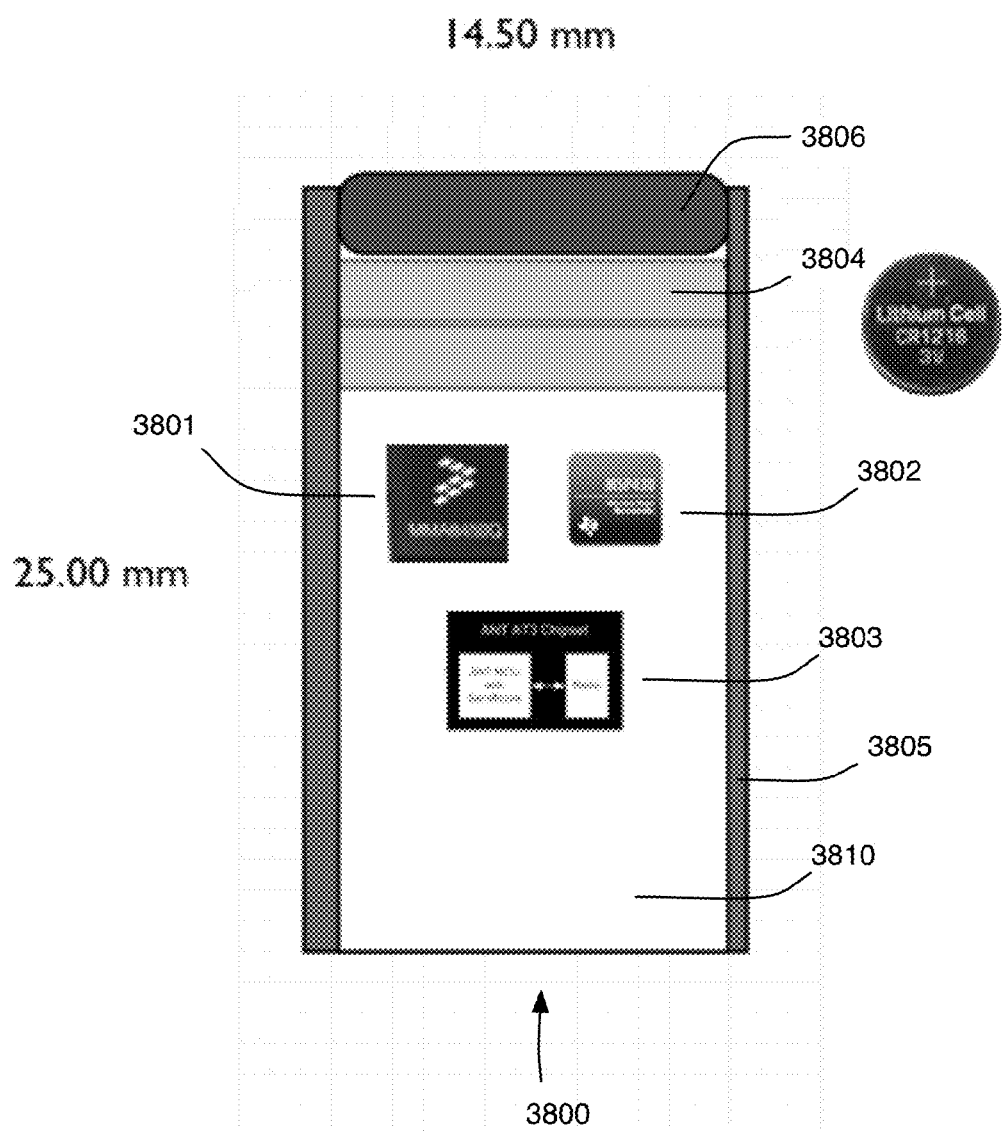
FIG. 38 shows elements of an embodiment of the motion capture element configured to fit into the end of a golf shaft.

FIG. 11 illustrates a hardware implementation of the sensor portion of a motion capture element implemented as a wireless inertial measurement unit, and an embodiment as configured to couple with a weight port of a golf club for example. Printed circuit board (PCB) may be utilized to hold the various components of the sensor including any orientation, position, velocity and/or accelerometers. Hole 1101 may be utilized as a screw hole or other coupling point for coupling motion capture element 111 to a piece of equipment, such as into a weight port of a golf club. Alternatively, threads at location 1102 or at location 1103 may be utilized to screw motion capture element 111 onto the piece of equipment. Any other method of coupling motion capture element to a piece of equipment or user is in keeping with the spirit of the invention. Embodiments of the invention may also be placed near the head of a golf club, in the handle of a golf club, or in any other piece of equipment. When placing an embodiment of the invention near the golf club head or handle, an adapter may be utilized so as to fit the apparatus to the specific make and/or model of the golf club. Each manufacturer has multiple types of weight port sizes, locations and shapes and any adapter that can for example screw into a weight port hole and also fit threads at location 1102 may be utilized as an adapter. For handles, any tube size for a given make or model of a club may be utilized as an adapter so long as it allows the components of embodiments of the invention to fit inside the golf club and withstand the forces involved with a golf club swing. See also FIGS. 38-42. In a wired embodiment of the golf club, apparatus 111 for example as mounted near a golf club head may electrically couple to another apparatus 3800 as shown in FIG. 38 so as to allow wired recharging of both apparatus in one golf club simultaneously.

Figure 12:
FIG. 12 illustrates an embodiment of the motion capture element as configured to couple with different golf club types and a shoe.

FIG. 12 illustrates an embodiment of the motion capture element as configured to couple with different golf club types and a shoe. As shown in the leftmost figure, motion capture element 111 can couple directly to a piece of equipment such as a golf club in the rear portion of the club head. As the second from left figure illustrates, motion capture element 111 may couple onto the bottom of a piece of equipment, such as a golf putter. In addition, as the third figure from the left illustrates, motion capture element 111 may couple into the weight port of a piece of equipment, such as a driver. Furthermore, motion capture element may couple with a piece of equipment that is worn by the user, effectively coupling with the user as shown in the rightmost figure.

Figure 13:
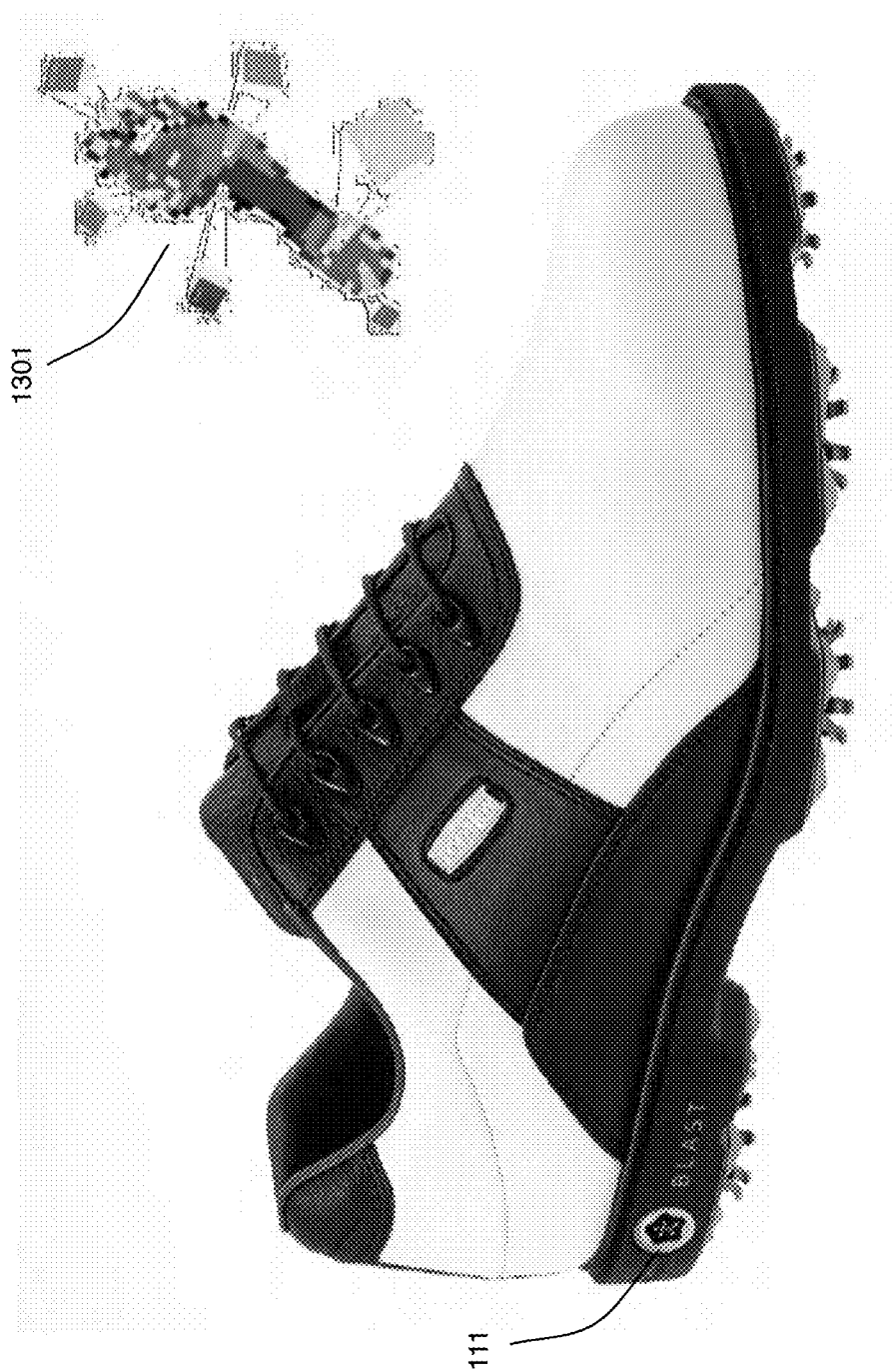
FIG. 13 illustrates a close-up of the shoe of FIG. 12 along with a pressure map of a shoe configured with a pressure matt inside the shoe configured to output pressure per particular areas of the shoe.

FIG. 13 illustrates a close-up of the shoe of FIG. 12 along with a pressure map of a shoe configured with a pressure matt inside the shoe configured to output pressure per particular areas of the shoe. In this embodiment, motion capture element may also interface to a pressure sensing mat capable of producing pressure map 1301 from inside of the shoe and relay the pressure information to the mobile device for analysis. Alternatively, pressure sensors may be placed through the shoe, for example in a grid, to provide weight bearing information to the mobile device, for example wirelessly via the motion capture element. Each pressure sensor may couple to a transceiver or contain its own transceiver, or couple via wires or wirelessly to the motion capture element in order to transmit pressure data, for example to display on display 120. By color coding the map and displaying the map on display 120, a color graphic rating is thus obtained, which may include numerical ratings of the pressure signature when compared to saved pressure maps which resulted in good swings for example.

Figure 14:
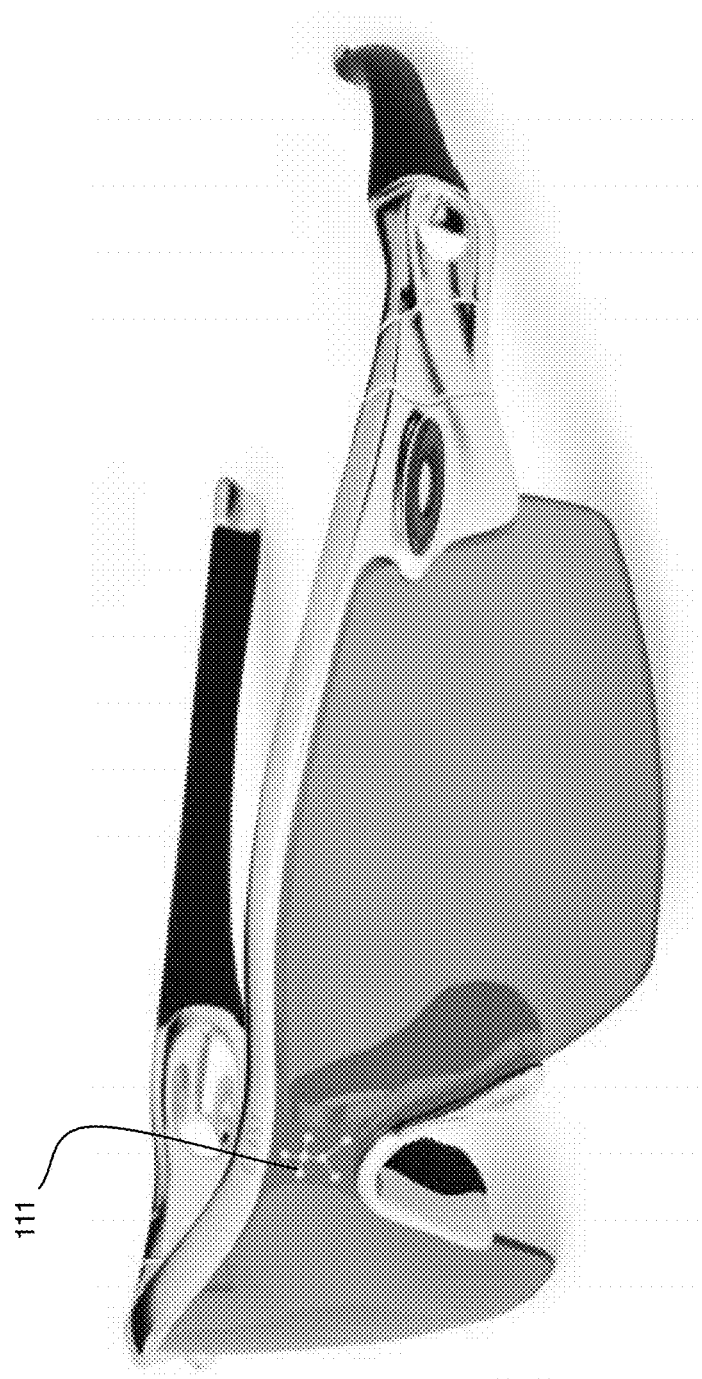
FIG. 14 illustrates an embodiment of sunglasses configured with an embodiment of the motion capture element.

FIG. 14 illustrates an embodiment of sunglasses configured with a motion capture element. In addition, the sunglasses may also include a video viewing device that may be utilized for display 120 so that the user may watch images of the user with motion analysis data via the sunglasses. In this manner, any computer 160, 105, or any other computer coupled to network 170 or Internet 171 may be utilized to obtain data and analyze data so that the resulting motion analysis data may be displayed on the sunglasses, for example for virtual reality and/or augmented virtual reality display.

Figure 15:
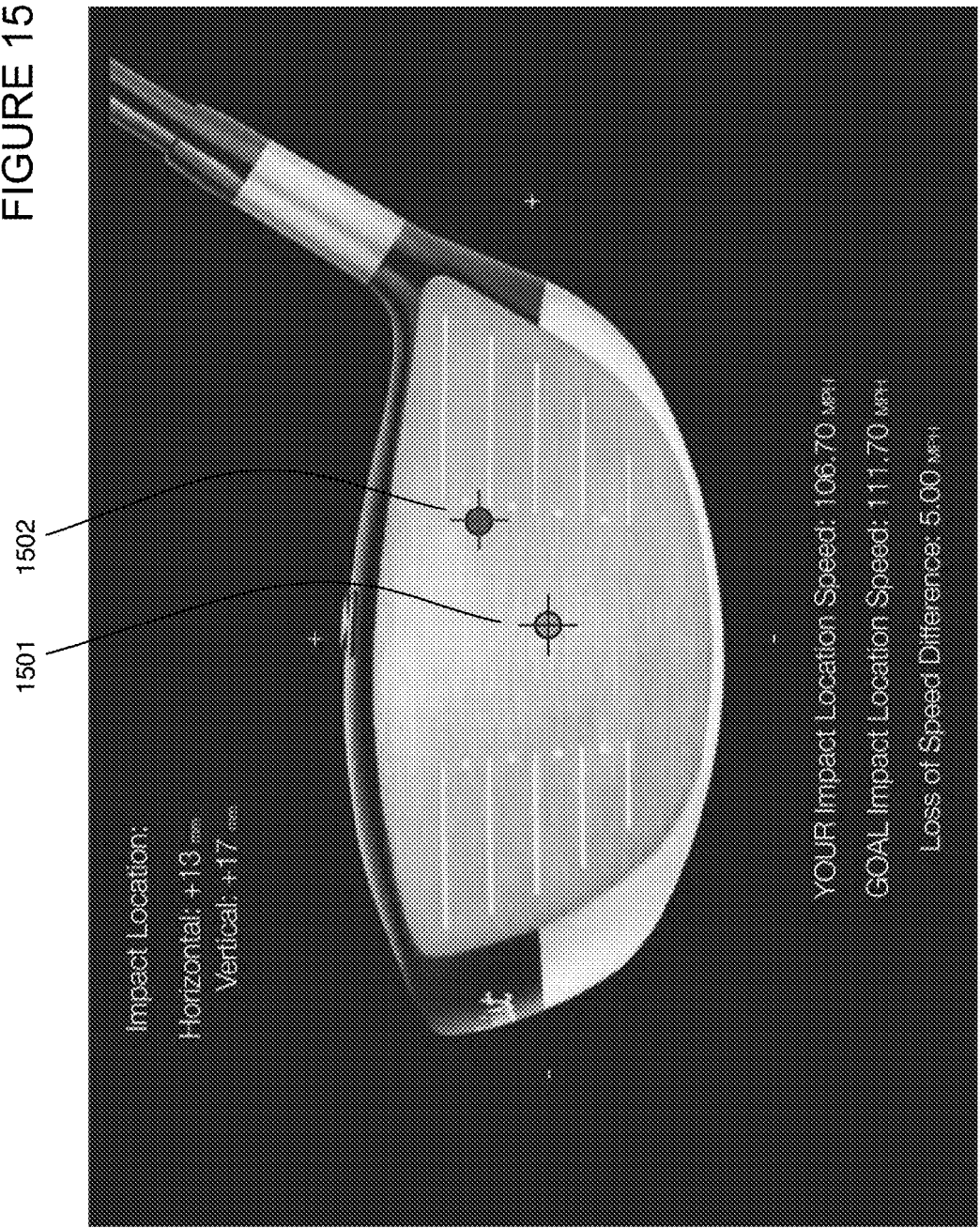
FIG. 15 illustrates an embodiment of a display that depicts the location of a golf ball strike as determined by the oscillations in the golf club face during and/or after the golf club impacts a golf ball.

FIG. 15 illustrates an embodiment of a display that depicts the location of a golf ball strike as determined by the oscillations in the golf club face during and/or after the golf club impacts a golf ball. In one or more embodiments of the invention, if the golf ball impacts the club at location 1501, then a particular frequency response is obtained via orientation or velocity sensors in motion capture element 111 that is coupled with the club shown. If the golf ball impacts the club at location 1502, then a distinct frequency response is obtained via the motion capture element 111 coupled to the club. One embodiment for determining where a ball impacts a club involves recording impacts from a variety of locations at a range of speeds and using the resulting frequency responses to determine which one is the closest to the impact detected. Impacts that occur high or low on the club face tend to produce a vertical axis oscillation of greater amplitude than impacts that occur at location 1501. Impacts that occur closer to the shaft tend to produce lower amplitude oscillations in the horizontal axis than impacts that occur further from the shaft. Hence, another method for determining impact is to form a ratio of the amplitude of horizontal to vertical axis frequency amplitude and then search for the closest match from a saved set of impact frequency responses and retrieve the x and y locations on the club face where the closest match has occurred. In another embodiment of the system, a series of impacts is recording at the center of the club and at 4 points away from the center along the positive x axis, (away from the shaft), positive z axis (above the center point of the face), negative x axis (near the shaft) and negative z axis (below the center point of the face) wherein the motion capture element transmits x, y and z velocities associated with the impact. The velocities are converted into the frequency domain and saved. Then, when determining an impact location for a test swing, an interpolation between the impact in question and the center point and 4 other points is performed to determine the location of the impact. Any other method of determining the impact location that does not require other sensors besides the motion capture element coupled to the club is in keeping with the spirit of the invention.

Figure 16:
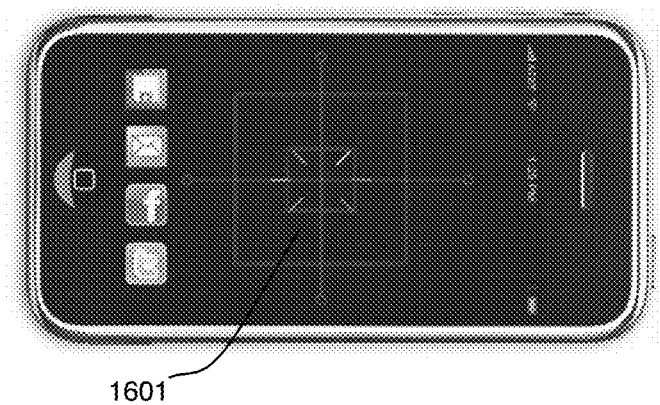
FIG. 16 illustrates a camera alignment tool as utilized with embodiments of the system to create normalized images for capture and analysis.
Figure 17:
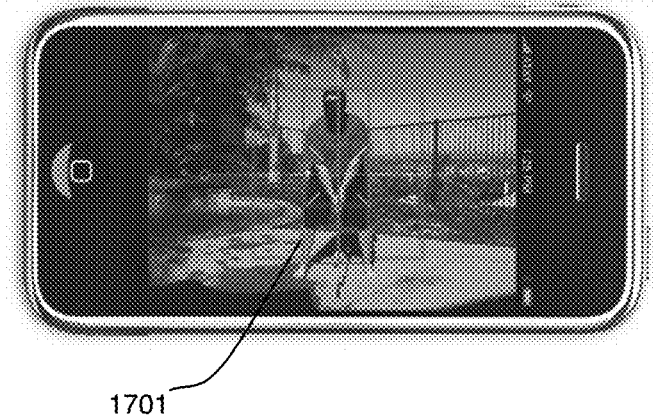
FIG. 17 illustrates a balance box and center alignment line to aid in centering a user to obtain image data.
Figure 18:
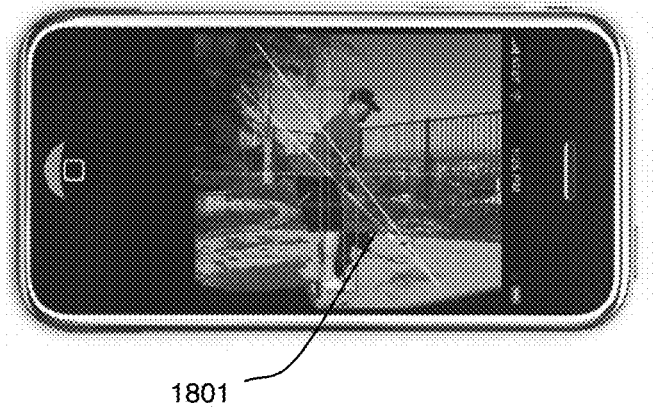
FIG. 18 illustrates a balance box and center alignment line, along with primary and secondary shaft lines to aid in centering and analyzing images of the user.

FIG. 16 illustrates a camera alignment tool as utilized with embodiments of the system to create normalized images for capture and analysis. In this figure, level lines 1601 are shown that for example become brighter when the mobile device is level. Any other manner of displaying that the mobile device is level may also be utilized. Icons on the left side of the screen show that the motion capture data and images may be saved, emailed, or sent to popular social networking sites such as FACEBOOK® and TWITTER®. FIG. 17 illustrates a balance box and center alignment line to aid in centering a user to obtain image data. FIG. 18 illustrates a balance box and center alignment line, along with primary and secondary shaft lines to aid in centering and analyzing images of the user for use in capturing data from the side of the user. Once the user is centered, the computer may obtain data and images that are normalized to the horizontal plane.

Figure 19:
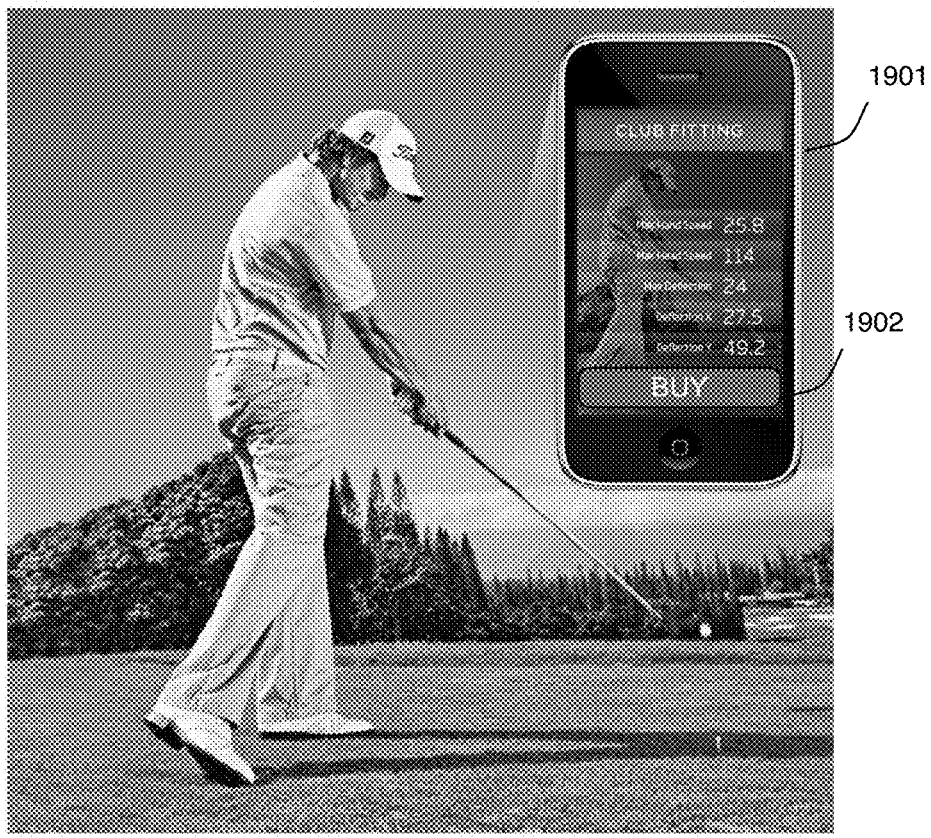
FIG. 19 illustrates an embodiment of the display configured to aid in club fitting for a user, wherein a user may test multiple clubs and wherein the display shows motion analysis data. For embodiments of the invention may be utilized to obtain sensor data that is utilized for purchase and order fulfillment options, buttons such as "purchase" and "customer order" may be utilized.

FIG. 19 illustrates an embodiment of the display configured to aid in club fitting for a user, wherein a user may test multiple clubs and wherein the display shows motion analysis data. For embodiments of the system that include purchase and order fulfillment options, buttons such as "purchase" and "customer order" may be utilized. Alternatively, a "buy" button 1902 may be shown in "club fitting" mode 1901 that enables a user to buy or custom order a custom club that the user is working with.

Figure 20:
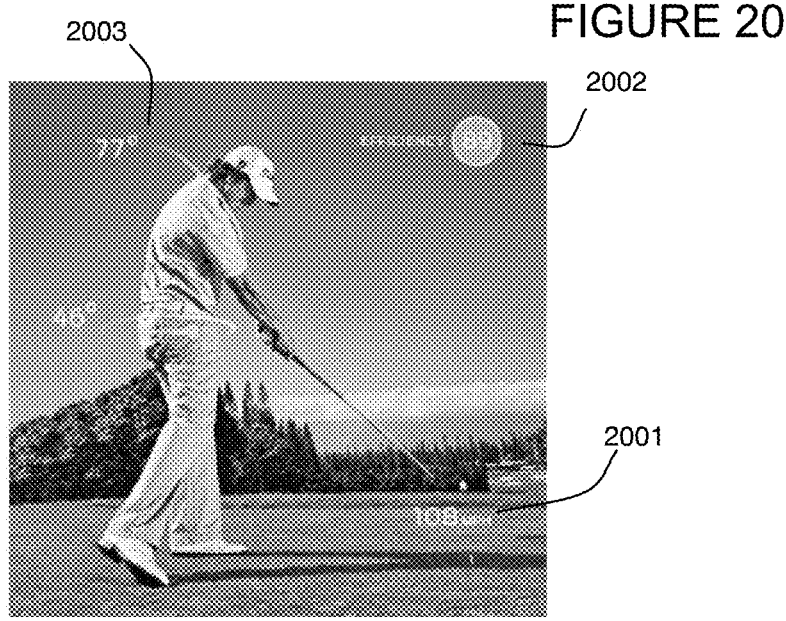
FIG. 20 illustrates an embodiment of the display configured to display motion analysis data along with the user, some of which is overlaid onto the user to aid in understanding the motion analysis data in a more human understandable format. In addition, motion analysis data associated with the user can be shown numerically as shown for example as "efficiency" of the swing, and the velocity of the swing.

FIG. 20 illustrates an embodiment of the display configured to display motion analysis data along with the user, some of which is overlaid onto the user to aid in understanding the motion analysis data in a more human understandable format. For example, rotation rings 2003 may be shown overlaid on one or more images of the user to shown the angle of the axis of rotation of portions of the user's body, such as shoulders and hips. In addition, motion analysis data associated with the user can be shown numerically as shown for example as "efficiency" of the swing 2002, and velocity of the swing 2001. The motion capture data and images may be saved to database 172 and later utilized to play a game against another player for example on a virtual reality golf course. The player may be a historical player whose performance data has been analyzed and stored in the database for later game playing for example.

Figure 21:
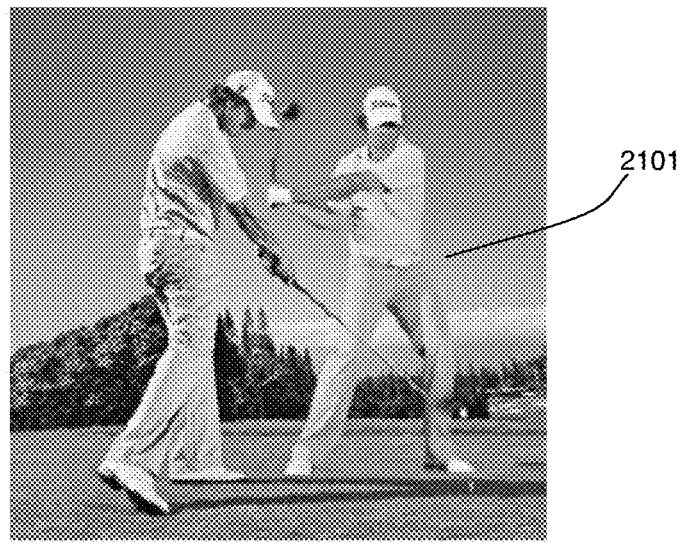
FIG. 21 illustrates an embodiment of the system configured to display a user from multiple angles when multiple cameras are available. One or more embodiments of the system may show one image of the user at a time in slow motion as the user moves, while changing the angle of the view of the user in normal time, which is known as BULLET TIME®.

FIG. 21 illustrates an embodiment of the system configured to display a user from multiple angles 2101 when multiple cameras are available. Any algorithm that may process images to eliminate backgrounds for example may be utilized to show multiple instances of the user on one background. Alternatively, one or more embodiments of the system may show one image of the user at a time in slow motion as the user moves, while changing the angle of the view of the user in normal time, which is known as BULLET TIME®.

Figure 22:
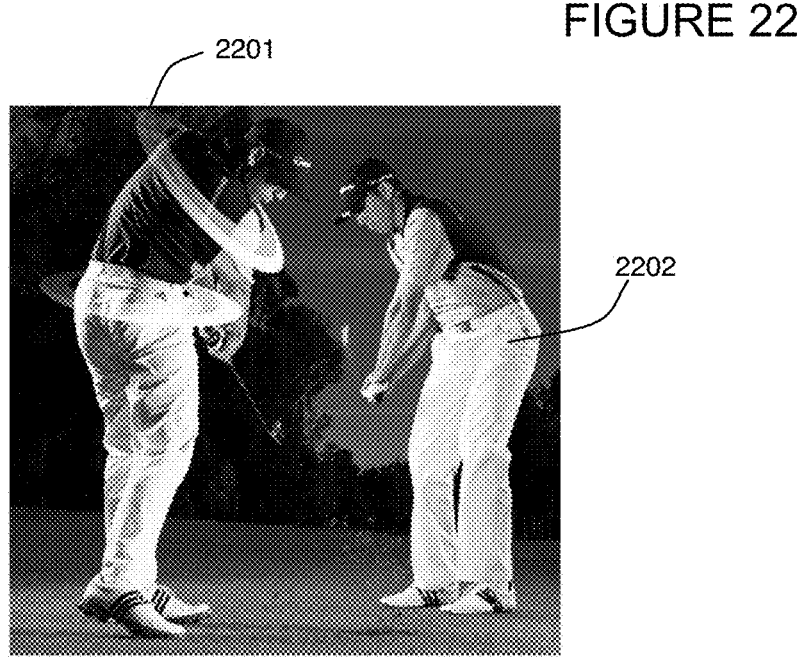
FIG. 22 illustrates another embodiment of the multi-angle display as is also shown in FIG. 21 wherein this figure also includes three-dimensional overlay graphics to aid in understanding the motion analysis data in a more human understandable manner.

FIG. 22 illustrates another embodiment of the multi-angle display as is also shown in FIG. 21. This figure also includes three-dimensional overlay graphics 2201 to aid in understanding the motion analysis data in a more human understandable manner. Second instance of the user 2202 may or may not be shown with the same overlay from a different angle.

Figure 23:
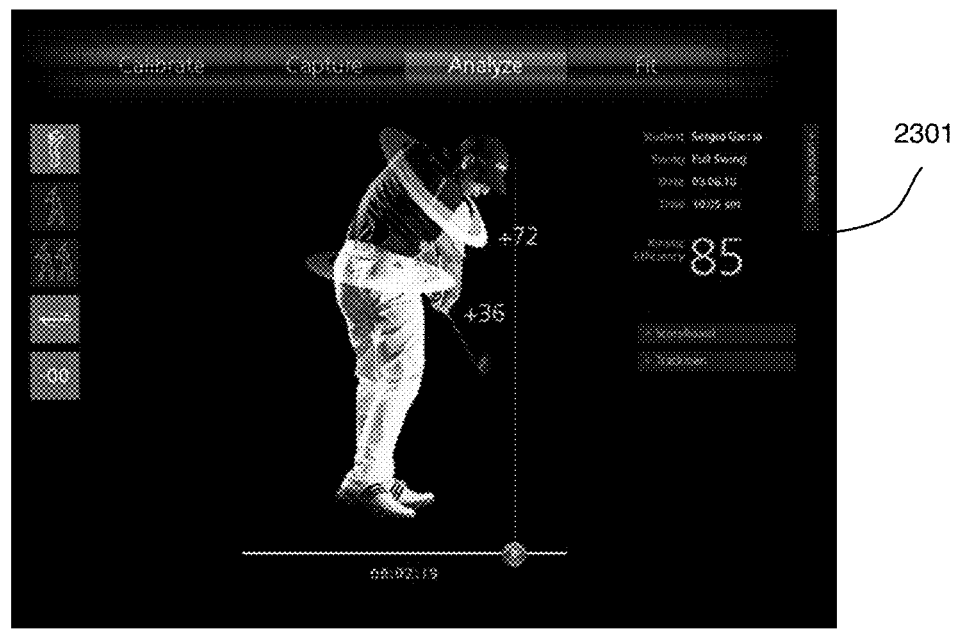
FIG. 23 shows an embodiment of the system configured to display motion analysis data on a mobile computer, personal computer, IPAD® or any other computer with a display device large enough to display the desired data.

FIG. 23 shows an embodiment of the system configured to display motion analysis data on a mobile computer, personal computer, IPAD® or any other computer with a display device large enough to display the desired data.

In any embodiments detailed herein, efficiency may be calculated in a variety of ways and displayed. For embodiments of the invention that utilize one motion capture element, then the motion capture element associated with the club head may be utilized to calculate the efficiency. In one or more embodiments of the invention, efficiency may be calculated as:

$$\text{Efficiency} = (90 - \text{angle of club face with respect to direction of travel}) * Vc/V\max$$

Figure 24:
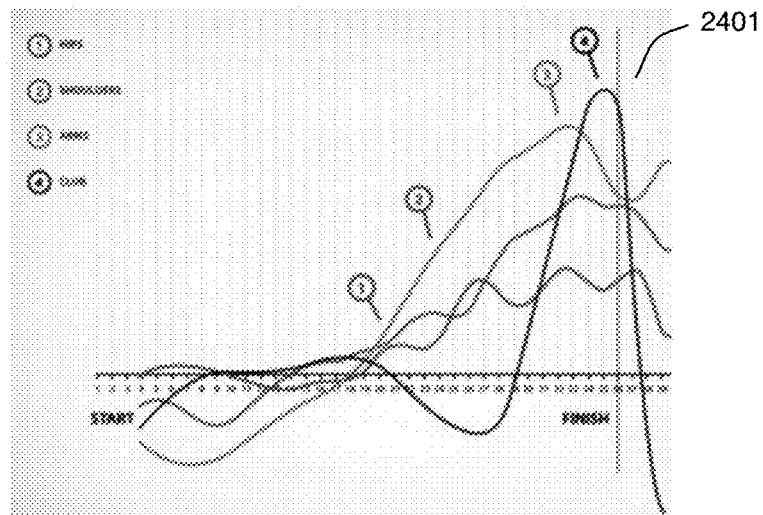
FIG. 24 illustrates a timeline display of motion analysis data that shows multiple sensor angular velocities in reference to the world or for example to a portion of the piece of equipment or object to hit or a virtual spine or a boney landmark, as obtained from sensors on a user and/or on a piece of equipment.
Figure 25:
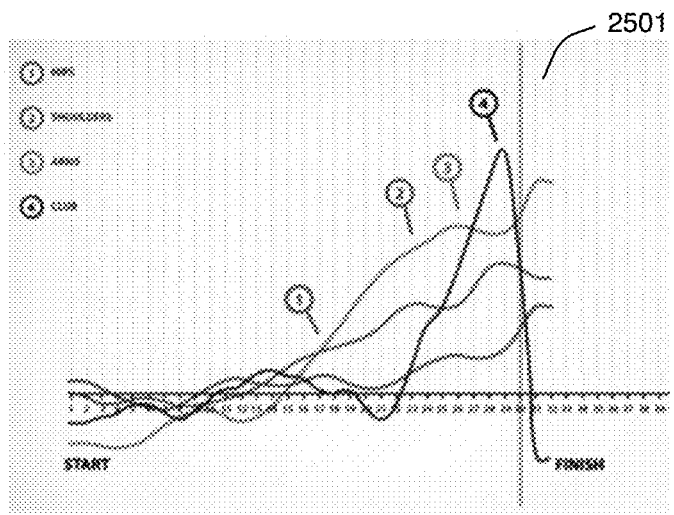
FIG. 25 illustrates a timeline display of motion analysis data that shows multiple sensor angular speeds obtained from multiple sensors on a second user and on a piece of equipment. Efficient movement pattern of body segments know as a kinetic chain and of kinematic segmental sequencing.

As more sensors are added further from the piece of equipment, such as in this case a club, the more refined the efficiency calculation may be. FIG. 24 illustrates a timeline display of motion analysis data that shows multiple sensor angular speeds obtained from multiple sensors on a user and on a piece of equipment. FIG. 25 illustrates a timeline display of angular speed of a second user. One or more embodiments of the system may calculate an efficiency based on relative times of the peaks of the hips, shoulders, arms and club for example. In one or more embodiments of the invention utilizing more than one motion capture element, for example on the handle and club head, the angular velocity Wa of the handle is divided by the angular velocity Wc of the club head to calculate efficiency with more information. By obtaining a large number of timelines from various professional athletes and determining average amplitudes of angular velocities of various body parts and/or timings, then more refined versions of the efficiency equation may be created and utilized.

$$\text{Efficiency} = (90 - \text{angle of club face with respect to direction of travel}) * Vc/V\max * Wa/Wc * 1.2$$

Figure 26:
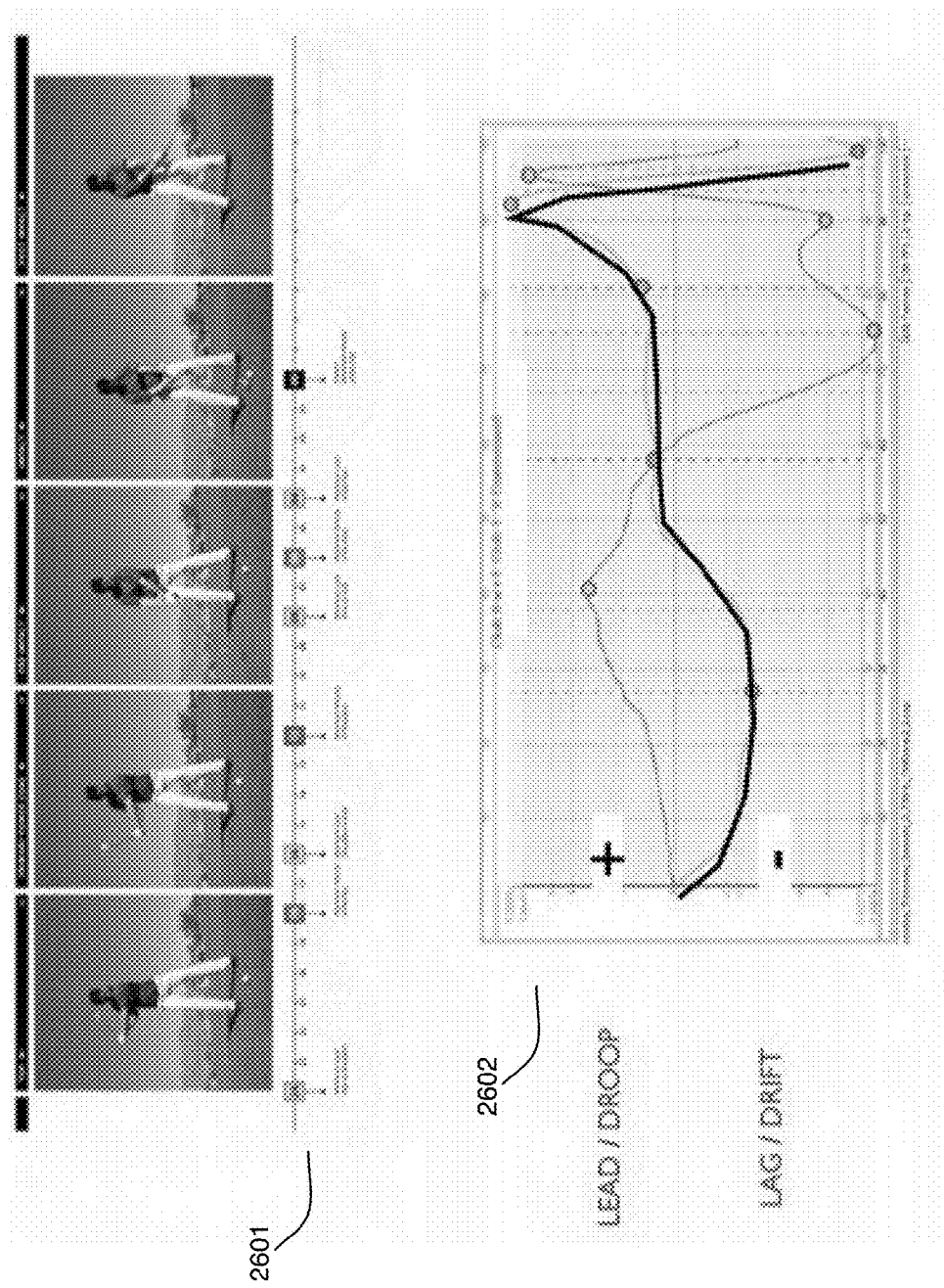
FIG. 26 illustrates a timeline display of a user along with peak and minimum angular speeds along the timeline shown as events along the time line instead of as Y-axis data as shown in FIGS. 24 and 25. In addition, a graph showing the lead and lag of the golf club along with the droop and drift of the golf club is shown in the bottom display wherein these values determine how much the golf club shaft is bending in two axes as plotted against time.

FIG. 26 illustrates a timeline display of a user along with peak and minimum angular speeds along the timeline shown as events along the time line instead of as Y-axis data as shown in FIGS. 24 and 25. In this unique view, the points in time where the peaks of the graphs of FIGS. 24 and 25 are shown as colored boxes that correspond to the colors of the graphs in FIGS. 24 and 25, yet in a more human understandable format that shows the relative timing of the peaks. In addition, at the bottom of FIG. 26 a graph showing the lead and lag of the golf club along with the droop and drift of the golf club is shown wherein these values determine how much the golf club shaft is bending in two axes as plotted against time.

One or more embodiments of the system may analyze the peaks and/or timing of the peaks in order to determine a list of exercises to provide to a user to improve the mechanics of the user. For example, if the arms are rotating too late or with not enough speed, a list can be provided to the user such as:

TABLE 1

| Arm Speed | Exercise |
| --- | --- |
| 1000-1500 degrees/sec | Impact Bag Drawbacks |
| 1501-1750 degrees/sec | Drawbacks |
| 1751-2000 degrees/sec | No drills |

The list of exercises may include any exercises for any body part and may displayed on display 120. For example, by asserting the "Training" button on the displays shown in FIG. 6, a corresponding body part list of exercises may be displayed on display 120.

Figure 27:
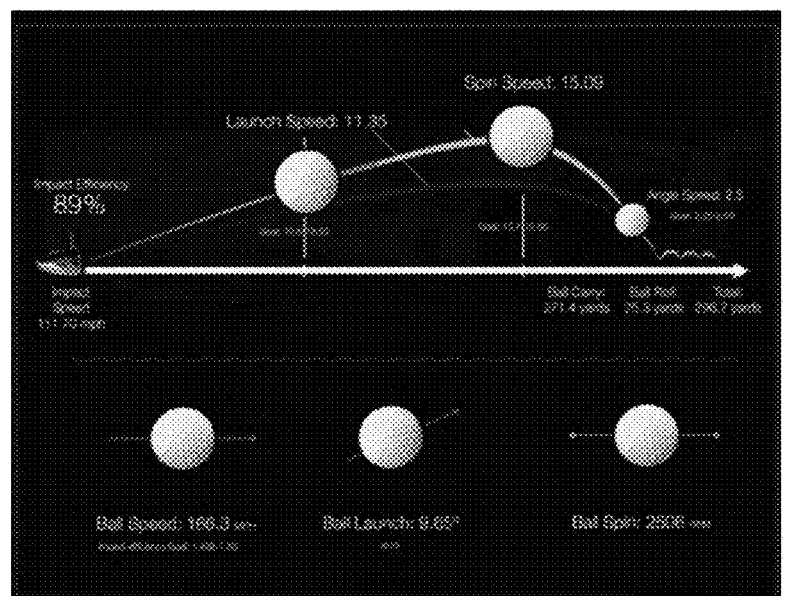
FIG. 27 illustrates a display of the calculated flight path of a ball based on the motion analysis data wherein the display is associated with any type of computer, personal computer, IPAD® or any other type of display capable of displaying images.
Figure 28:
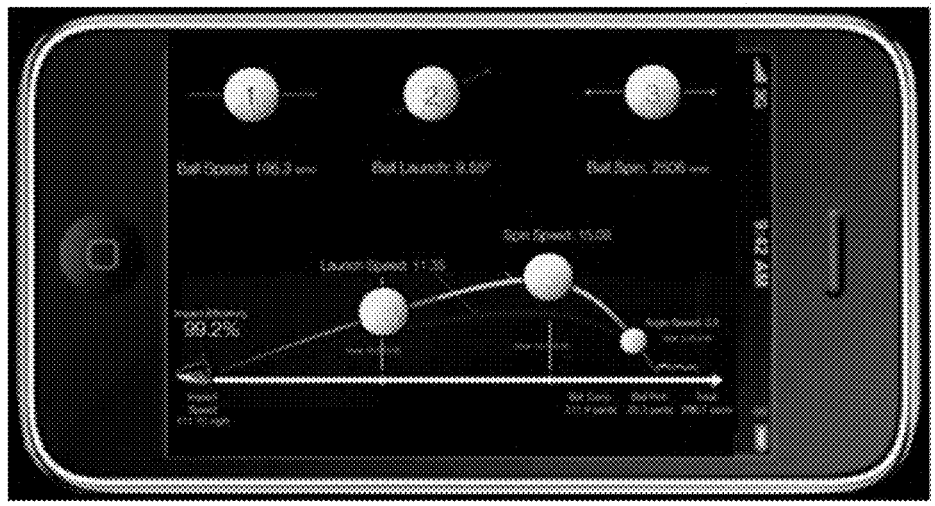
FIG. 28 illustrates a display of the calculated flight path of a ball based on motion analysis data wherein the display is coupled with a mobile device.

FIG. 27 illustrates a display of the calculated flight path 2701 of a ball based on the motion analysis data wherein the display is associated with any type of computer, personal computer, IPAD® or any other type of display capable of displaying images. FIG. 28 illustrates a display of the calculated flight path 2801 of a ball based on motion analysis data wherein the display is coupled with a mobile device. After a swing of a golf club, and based on the club head speed as determined by motion capture element 111, the loft of the club and the angle at which the club strikes the ball (meaning that there is another motion capture element in the handle or near the hands of the user), a flight path may be calculated and displayed. Any model may be utilized as is known in the art to calculate the trajectory based on the club velocity as measure via motion capture element 111, one such model is described in a paper by MacDonald and Hanzely, "The physics of the drive in golf", Am. J. Phys 59 (3) 213-218 (1991). See FIG. 37 for one embodiment of the equation used to calculate the accelerations in the x, y and z axes wherein:

x=laterally sideways (right is positive, left is negative)
y=down the fairway (always positive)
z=vertically upwards (up is positive, down is negative)
B=a constant dependent on the conditions of the air, an appropriate value=0.00512
u=vector of relative velocity between the ball and the air (i.e. wind), $u=v-v_w$
Cd=coefficient of drag which depends on the speed and spin of the ball
Cl=coefficient of drag which depends on the speed and spin of the ball
a=the angle between the vertical and the axis of rotation of the spinning ball
g=the acceleration due to gravity=32.16 ft/s2

A numerical form of the equations may be utilized to calculate the flight path for small increments of time assuming no wind and a spin axis of 0.1 radians or 5.72 degrees is as follows:

$$x \text{ acceleration} = -0.00512*(vx^2+vy^2+vz^2)^{(1/2)}* ((46.0/(vx^2+vy^2+vz^2)^{(1/2)})*(vx)+(33.4/(vx^2+vy^2+vz^2)^{(1/2)})*(vy)*\sin(0.1))$$

$$y \text{ acceleration} = -0.00512*(vx^2+vy^2+vz^2)^{(1/2)}* ((46.0/(vx^2+vy^2+vz^2)^{(1/2)})*(vy)-(33.4/(vx^2+vy^2+vz^2)^{(1/2)})*((vx)*\sin(0.1)-(vz)*\cos(0.1)))$$

$$z \text{ acceleration} = -32.16-0.00512*(vx^2+vy^2+vz^2)^{(1/2)}*((46.0/(vx^2+vy^2+vz^2)^{(1/2)})*(vz)-(33.4/(vx^2+vy^2+vz^2)^{(1/2)})*(vy)*\cos(0.1))$$

Figure 29:
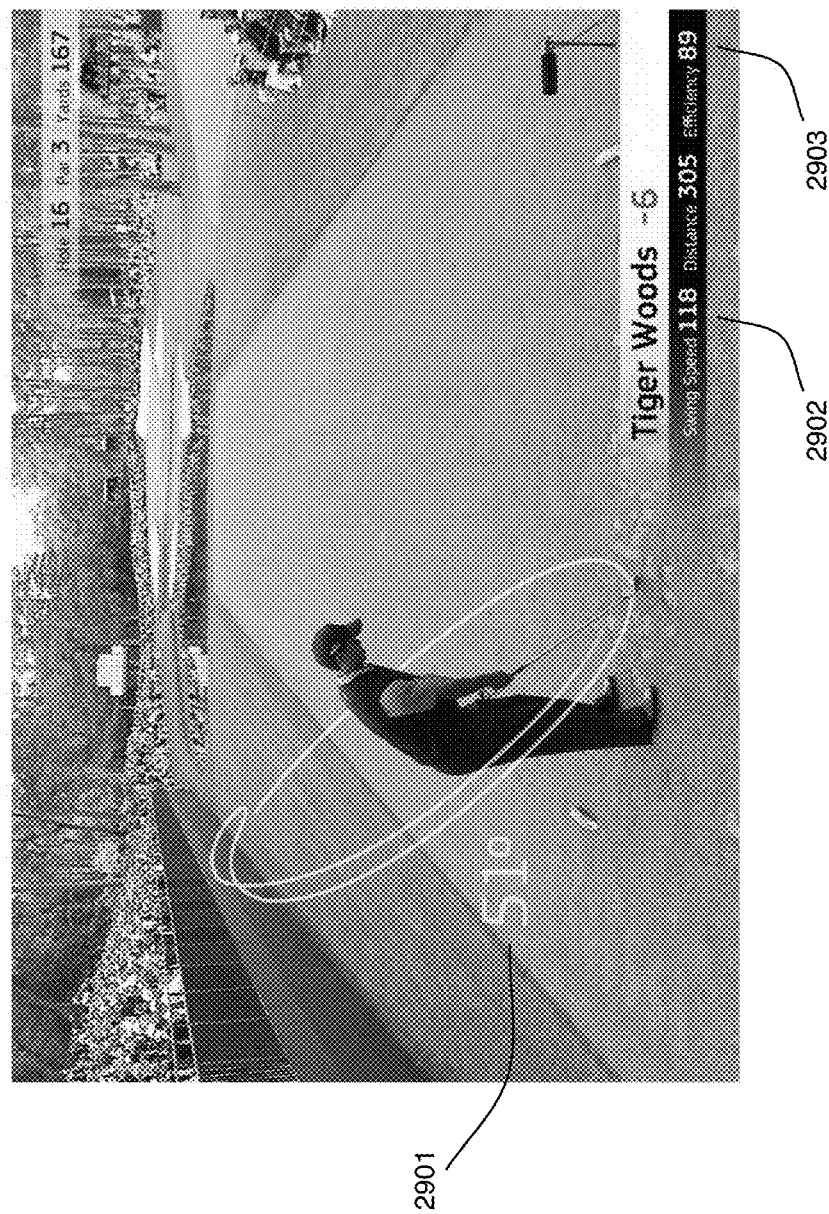
FIG. 29 illustrates a display of a broadcast television event wherein at least one motion capture element in the form of a motion sensor is coupled with the golf club and optionally the user. The display can be shown in normal time after the athlete strikes the ball, or in slow motion with motion analysis data including the three-dimensional overlay of the position of the sensor on the end of the club shown as a trace line and including the angle of the plane in which the swing takes place versus the horizontal plane. In addition, other motion analysis data may be shown such as the swing speed, distance (calculated or actual) and efficiency.

FIG. 29 illustrates a display of a broadcast television event wherein at least one motion capture element in the form of a motion sensor is coupled with the golf club and optionally the user. The display can be shown in normal time after the athlete strikes the ball, or in slow motion with motion analysis data including the three-dimensional overlay of the position of the sensor on the end of the club shown as a trace line and including the angle of the plane 2901 in which the swing takes place versus the horizontal plane. In addition, other motion analysis data may be shown such as the swing speed 2902, distance (calculated or actual) and efficiency 2903.

Figure 30:
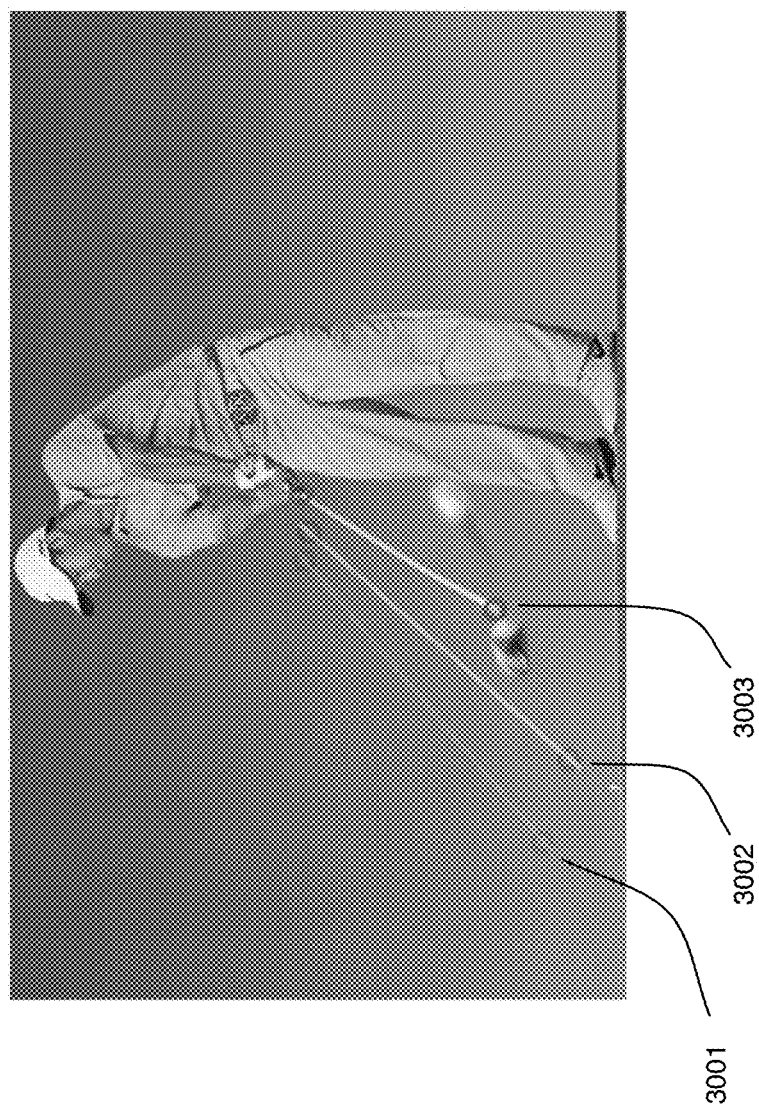
FIG. 30 illustrates a display of the swing path with a strobe effect wherein the golf club in this example includes sensors on the club head and hear the handle, or optionally near the hands or in the gloves of the user. Optionally, imaged based processing from a high speed camera may be utilized to produce the display. The swing path for good shots can be compared to swing paths for inaccurate shots to display the differences in a human understandable manner.

FIG. 30 illustrates a display of the swing path with a strobe effect wherein the golf club in this example includes sensors on the club head and near the handle, or optionally near the hands or in the gloves of the user. Optionally, imaged based processing from a high speed camera may be utilized to produce the display. A line or captured portion of the actual shaft from images may be displayed at angle 3001, 3002 and 3003 for example. The swing path for good shots can be compared to swing paths for inaccurate shots to display the differences in a human understandable manner.

Figure 31:
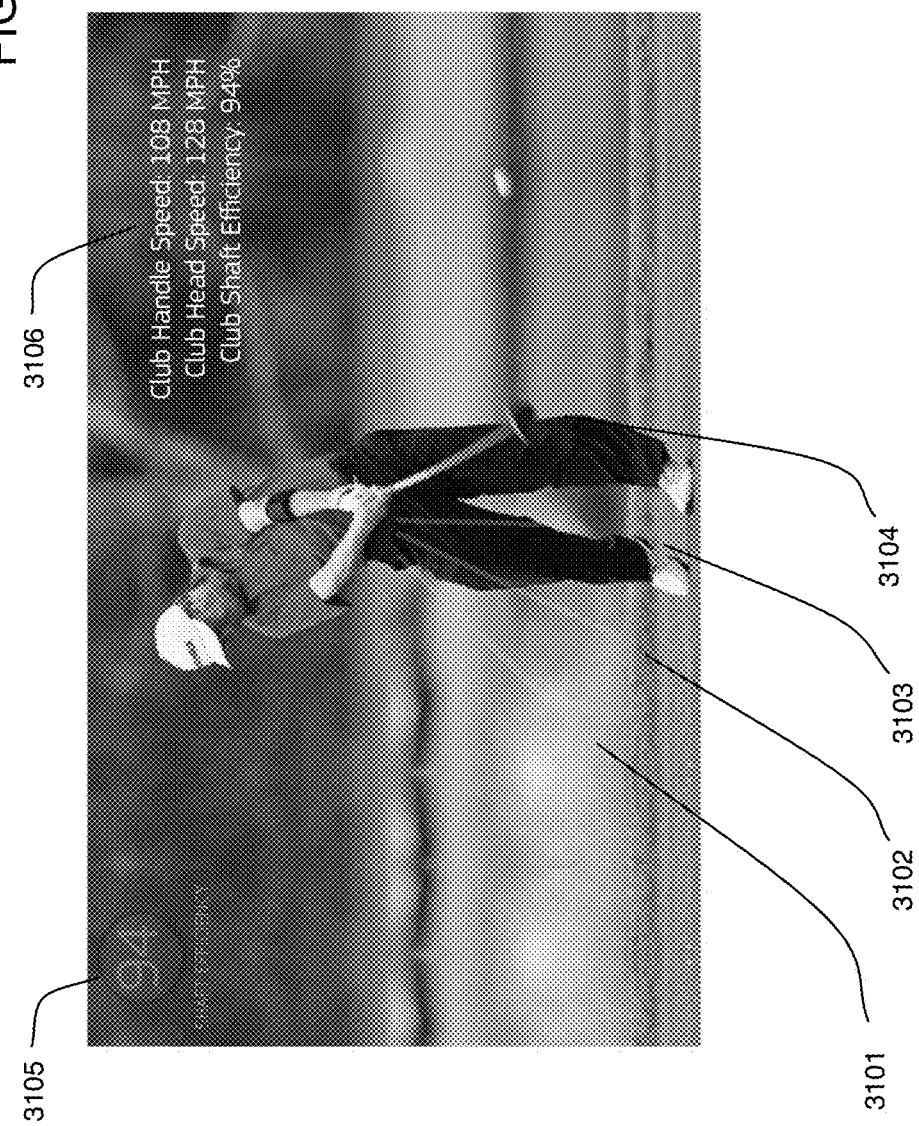
FIG. 31 illustrates a display of shaft efficiency as measured through the golf swing. For example, by obtaining motion capture data near the club head and club handle, graphical strobe effects and motion analysis data can show the club head speed, club handle speed and club shaft efficiency in normal time or slow motion.

FIG. 31 illustrates a display of shaft efficiency 3105 as measured through the golf swing. For example, by obtaining motion capture data near the club head and club handle, graphical strobe effects and motion analysis data can show the club head through time at 3101, 3102, 3103 and 3104 and also display speed, club handle speed and club shaft efficiency at 3106 in normal time or slow motion.

Figure 32:
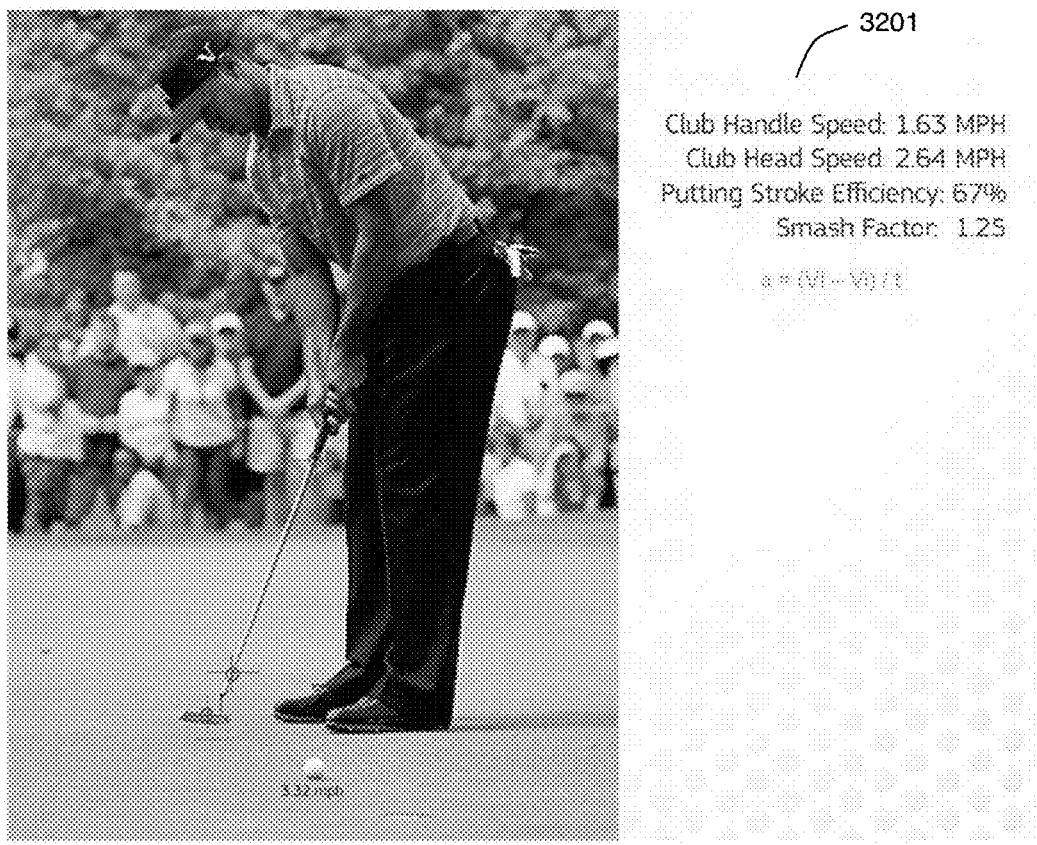
FIG. 32 illustrates a display of putter head acceleration based on at least one sensor near the putter head, for example as coupled into the weight port of a putter. The various quantities from the motion analysis data can be displayed to aid in understanding acceleration patterns for good putts and bad putts to help viewers understand acceleration in a more human understandable manner.

FIG. 32 illustrates a display of putter head speed and/or acceleration based on at least one sensor near the putter head, for example as coupled into the weight port of a putter. The various quantities from the motion analysis data can be displayed at 3201 to aid in understanding speed and/or acceleration patterns for good putts and bad putts to help viewers understand speed and/or acceleration in a more human understandable manner.

Figure 33:
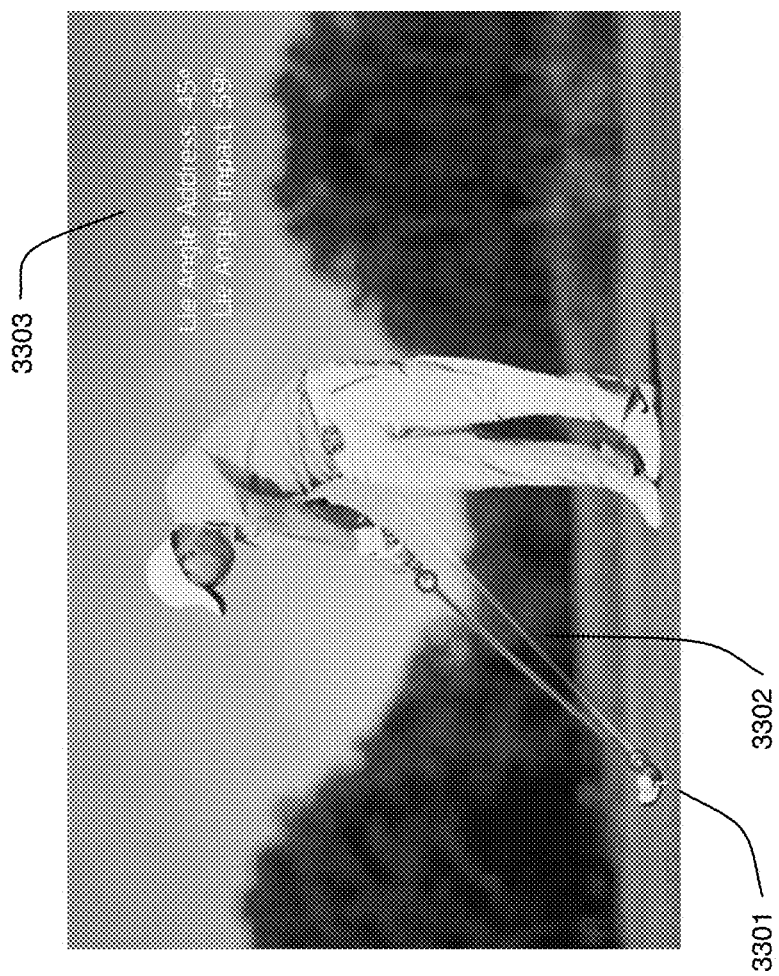
FIG. 33 illustrates a display of dynamic lie angle, wherein the lie angle of the player at address before swinging at the ball can be compared to the lie angle at impact to help the viewer understand how lie angle effects loft and ball flight.

FIG. 33 illustrates a display of dynamic lie angle, wherein the lie angle of the player at address 3302 before swinging at the ball can be compared to the lie angle at impact 3301 to help the viewer understand how lie angle effects loft and ball flight, while quantitatively showing the values at 3303.

Figure 34:
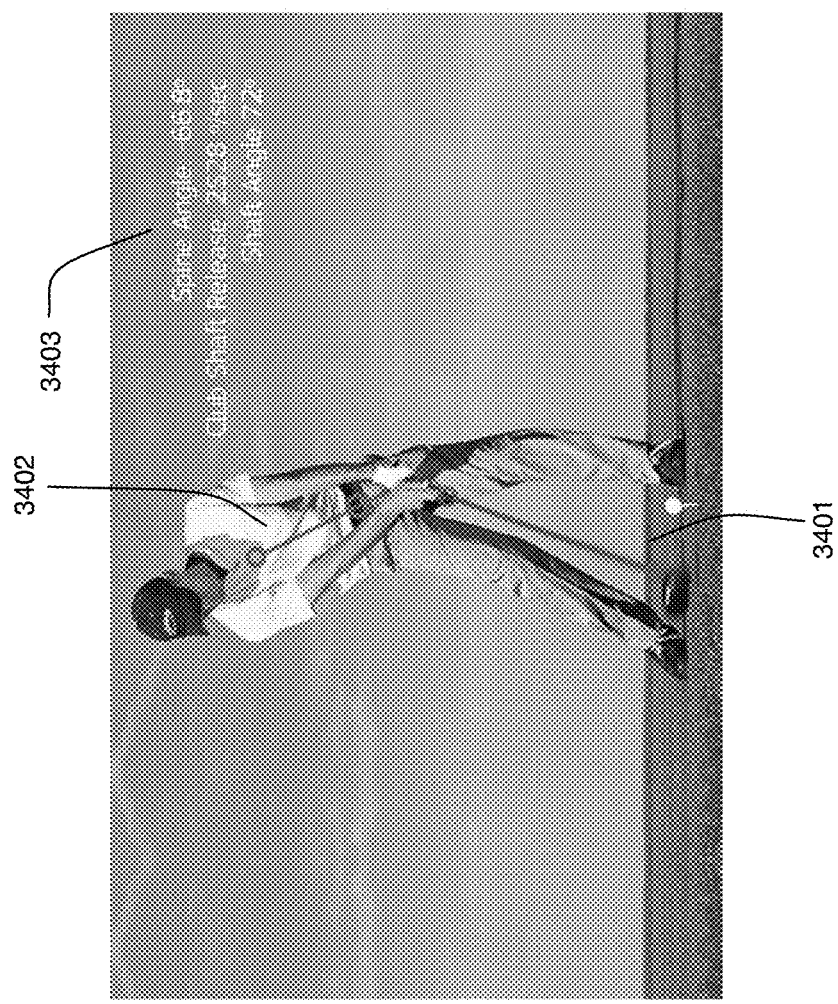
FIG. 34 illustrates a display of shaft release, wherein the angular release velocity of the golf shaft is a large component of the efficiency of a swing. As shown, a display of a golfer that has sensors near his waist and hips and sensors on the golf club head and handle, or as determined through image processing with or without visual markers, is shown with the motion analysis data.

FIG. 34 illustrates a display of shaft release, wherein the angular release velocity of the golf shaft is a large component of the efficiency of a swing. As shown, a display of a golfer that has sensors near his waist and hips (to produce spine angle 3402) and sensors on the golf club head and handle (to produce shaft angle 3401), or as determined through image processing with or without visual markers, is shown along with the motion analysis data including club shaft release in degrees per second at 3403.

Figure 35:
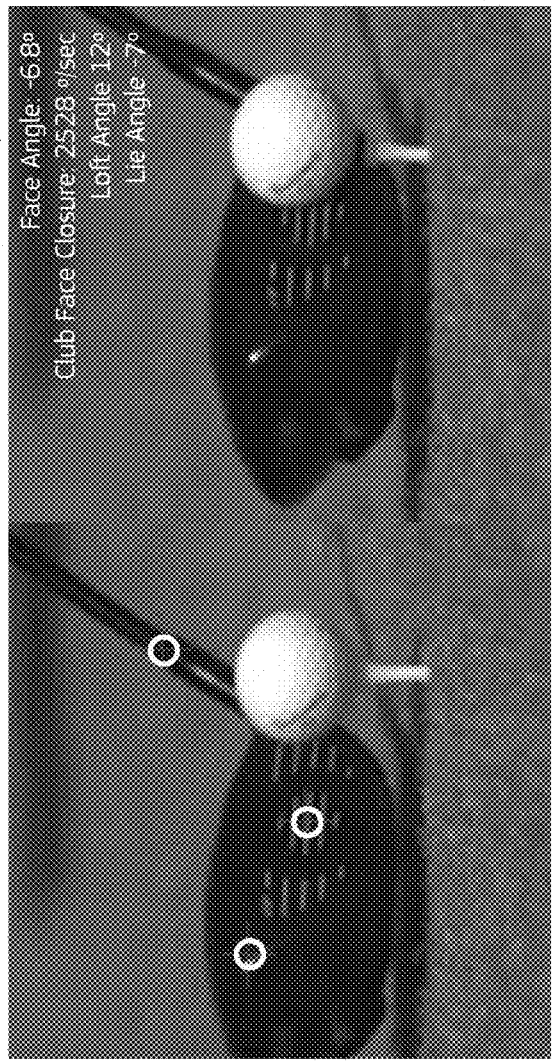
FIG. 35 illustrates a display of rotational velocity wherein the face angle, club face closure in degrees per second, the loft angle and lie angle are shown as obtained from a motion capture element on the club head for example.

FIG. 35 illustrates a display of rotational velocity wherein the face angle, club face closure in degrees per second, the loft angle and lie angle are determined from a motion capture sensor coupled with the club head for example and numerically shown at 3501.

Figure 36:
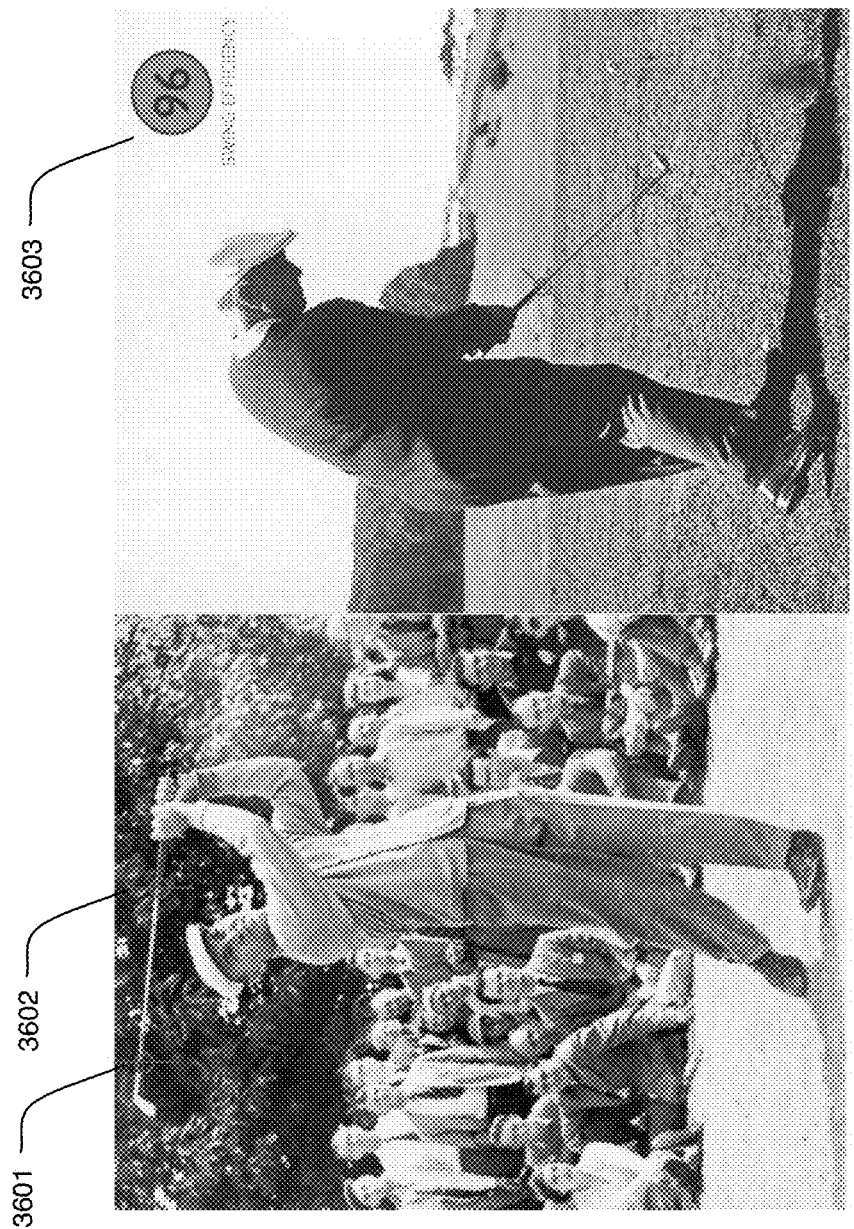
FIG. 36 illustrates a display of historical players with motion analysis data computed through image processing to show the performance of great players.

FIG. 36 illustrates a display of historical players with motion analysis data computed through image processing to show the performance of great players. By tracing and determining the locations of two points 3601 and 3602 on each player's golf club as shown and knowing the height of the players and/or lengths of their clubs and angle at which the images where taken, distances and thus velocities of the golf clubs may be determined to calculate numerical values as shown at 3603.

FIG. 37 illustrates one embodiment of the equations used for predicting a golf ball flight path as used to produce displays as shown in FIGS. 27 and 28.

FIG. 38 shows elements of an embodiment of the invention 3800 configured to fit into the end of a golf shaft. (See also FIG. 11 for another embodiment that may fit into a golf shaft or couple near the head of a golf club). Sensor 3801 may include spatial sensors that obtain data associated with orientation, position, velocity, acceleration (or any other derivative with respect to position and time). For example, accelerometer(s) may be utilized that obtain acceleration data in one or more axes. Alternatively, or in combination, the sensors may include gyroscope(s) that allow for orientation with respect to the horizon to be accurately determined. Alternatively, or in combination, the sensors may include magnetometers that allow for orientation with respect to North/South to be accurately determined. Any combination of these sensor types may be utilized to obtain spatial data that may be utilized by embodiments of the system described to analyze and display the spatial data in a user-friendly manner. Embodiments of the apparatus may include microcontroller 3802, i.e., a programmable computer element is small form factor, for example a low power microcontroller. One or more embodiments of the apparatus may include a unique identifier that identifies the particular instance of the apparatus. The identifier may be stored in the memory of microcontroller 3802 or in a separate chip (not shown for brevity and since microcontroller 3801 may include memory) or may be received by the microcontroller from an external system, i.e., programmed. In combination or alternatively, an identifier may be stored on identifier 191, for example implemented as an RFID tag that may be mounted on the end of the club or on the handle or under the handle of the club or in any other position on the club so long as the identifier may be read, for example by the computer on the mobile device. One or more embodiments of the invention may utilize passive RFID tags so that no battery is required to identify the specific club, or for example the club number of a particular club. Any other mechanism for obtaining a unique identifier that may be utilized with embodiments of the invention is in keeping with the spirit of the invention. The apparatus may also include radio and antenna 3803 (or separately as per FIG. 40 3803*a* and 4001) to enable wireless communication of the unique identifier and spatial data, for example via a communication mechanism that for example minimizes or eliminates communication interference so that multiple clubs from one or more players may be used in the same vicinity without communication interference. One or more embodiments of the radio may comprise BLUETOOTH®, adaptive frequency hopping spread spectrum, or code division multiple access (CDMA) or other wireless communications technologies having for example multiple channels of communication to allow for multiple radios to operate in a given location without interference. Power for the apparatus may derive from one or more batteries 3804. For example on or more CR1216 batteries may be utilized to double the amount of time that the club may be utilized. Embodiments of the apparatus may utilize mounting board 3810, for example a printed circuit board to mount the various components to. In addition, adapter 3805 may be utilized to house sensor 3801, microcontroller 3802, radio/antenna 3803, battery or batteries 3804 directly or via mounting board 3810 that may couple with these elements. Adapter 3805 may be unique to each golf club, manufacturer, model or any available standard, for example a handle standard size. In one or more embodiments adapter 3805 may comprise a 25 mm deep and 14.5 mm in diameter tube structure, for example made of epoxy or plastic or any other material strong enough to hold the various components in place and withstand the force involved with a golf swing. In addition, embodiments of the invention may also utilize cap 3806, for example a closure cap that is utilized to cover mounting board 3810 within the club handle (or club head). Closure cap 3806 may include a visual marker as is shown in FIGS. 9, 10 and 12 for example, for visual processing. In addition, cap 3806 may include a push switch to power the apparatus on and/or off. One or more embodiments of the invention power off automatically, or go into a hibernation mode after a particular amount of time the golf club has not moved over a certain speed for example. This may include mechanical and/or electronic indications that the club has moved and hence power should be restored. In addition, some or all of the components may be powered down and up periodically or until motion occurs or to check for a communications link for example. Any other power saving features may be implemented as desired to save more power based on the design requirements for a desired application as one skilled in the art will appreciate. In addition, by obtaining the spatial data from multiple apparatus coupled with a particular club for example enables the automatic determination of which apparatus is located in a handle and which apparatus is located at the golf club head based on the differences in speed during a swing for example. Any other method for automatically determining the assigned location of each apparatus on a given golf club is in keeping with the spirit of the invention. Example spatial sensor 3801 embodiments follow. One or more embodiments of the invention may utilize a MEMS digital output motion sensor LIS331HH ultra low-power high full-scale 3-axes "nano" accelerometer, or any other accelerometer for example. One or more embodiments of the invention may utilize a AK8975/AK8975C 3-axis electronic compass, or any other compass for example. One or more embodiments of the invention may utilize a L3GD20 MEMS motion sensor three-axis digital output gyroscope or any other gyroscope for example. One or more embodiment of microcontroller 3802 may be implemented with MICROCHIP® PIC24FJ256GA110 general purpose flash microcontroller or any other microcontroller. One or more embodiments of radio and antenna 3803 may be implemented with a BLUECORE®6-ROM single-chip BLUETOOTH® v2.1 EDR system, and/or a BLUECORE® CSR1000™ QFN BLUETOOTH® low energy single-mode chip, or any other communications chip. Any type of micropower harvesting technology may be utilized internally to charge a battery coupled to the microcontroller to minimize the changing or charging of batteries with an external charger.

In addition, embodiments of mount may utilize the mount specified in the parent application of which this application is a continuation in part and which has been incorporated by reference above in the priority claim.

Embodiments of the invention using a unique identifier may be utilized as a lost club alarm, so that if contact is lost with one of the clubs associated with a player, an alarm may be presented by one or more embodiments of the system. Embodiments of the system that include a three-axis accelerometer enable analysis and display of swing speed, tempo, handle versus head speed, swing efficiency, durability counter and shot by shot analysis. Embodiments of the invention that include a three axis gyroscope enable analysis and display of alignment, lie angle, loft angle, handle release and 3-D angular velocity. Embodiments of the invention that include a magnetometer enable analysis and display of swing tracer, swing path, impact location, ball flight, 3-D impact, shaft deflection, shaft efficiency and 3-D video overlay. Any other displays that make use of the different type of spatial sensors is in keeping with the spirit of the invention.

Figure 39:
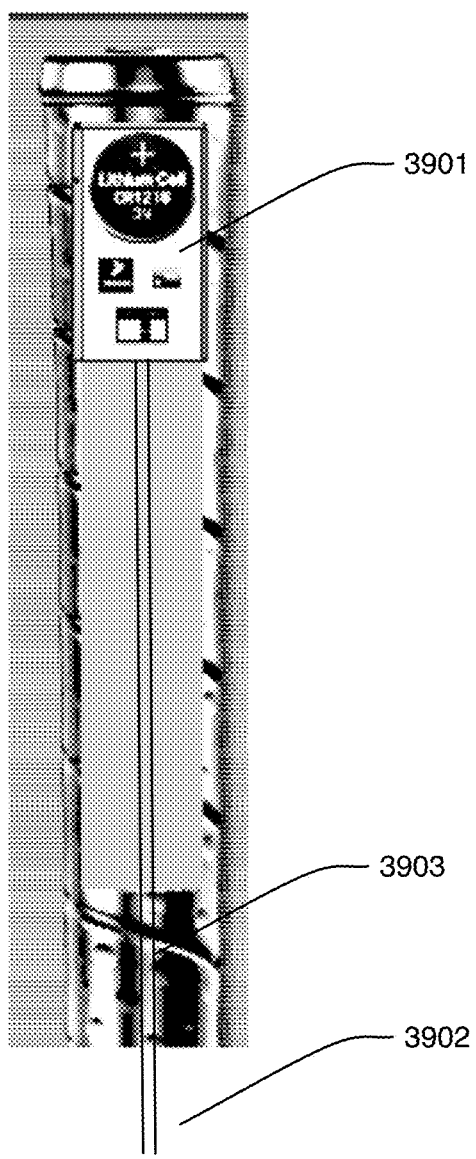
FIG. 39 shows an embodiment of the apparatus of FIG. 38 integrated into the handle of a golf club.

FIG. 39 shows an embodiment of the apparatus of FIG. 38, here designated 3901 as integrated into the handle of golf club 3902. Optional electrical connection 3903 enables the coupling of an embodiment of the invention situated in a handle of a golf club to an embodiment of the invention situated near the golf club head so as to allow for simultaneous recharging of both apparatus. Cap 3806 may include an inductive coil to allow for wireless charging (as is common in electric toothbrushes for example), or may include any type of power coupling interface or outlet, as one skilled in the art will appreciate. Any type of mechanical charging element, for example common in some watches, may also be coupled to the motion capture elements that do not require power. In addition, automatic power up and power down passive or active sensors or switches may be utilized to power microcontroller 3802 on or off.

Figure 40:
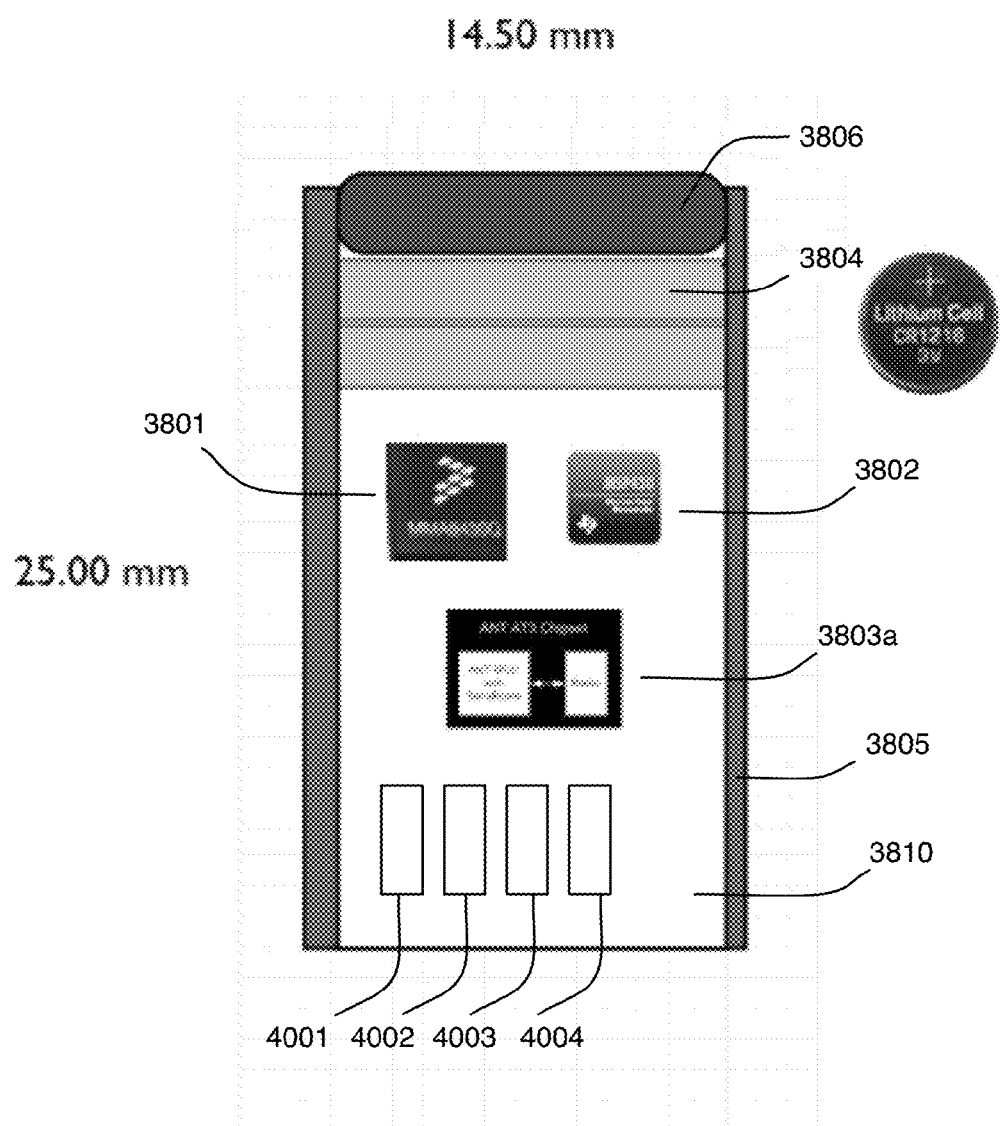
FIG. 40 shows elements of another embodiment of the invention configured to fit into the end of a golf shaft

FIG. 40 shows elements of another embodiment of the invention configured to fit into the end of a golf shaft. In this embodiment, mounting board 3810 also includes radio 3803*a*, along with antenna 4001 (as separate units compared with FIG. 38), optional heat sink 4002, recharger 4003 and overcharge detector 4004. Recharger 4003 may be implemented for example as an induction element that wirelessly enables recharging battery or batteries 3804. Overcharge detector 4004 may electrically connect with battery or batteries 3804 and recharger 4003 to determine when the batteries should no longer be charged, or when charging should resume. Alternatively, a wired connection may be utilized to charge battery or batteries 3804 as one skilled in the art will appreciate. In addition, since a wire may be run through the shaft of the golf club, the same charging port may be utilized to charge batteries in two or more apparatus, for example one located in a golf club handle and another one located near the golf club head. A wireless golf club is thus produced with a wired internal connection for ease of charging.

Figure 41:
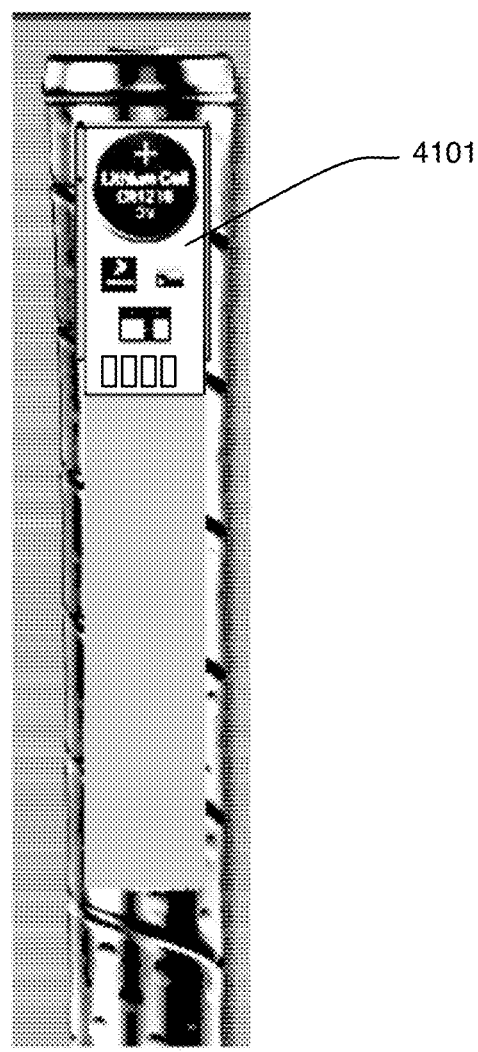
FIG. 41 shows another embodiment of the apparatus of FIG. 40 integrated into the handle of a golf club

FIG. 41 shows another embodiment of the apparatus of FIG. 40, here designated 4101 as integrated into the handle of golf club 3902.

Figure 42:
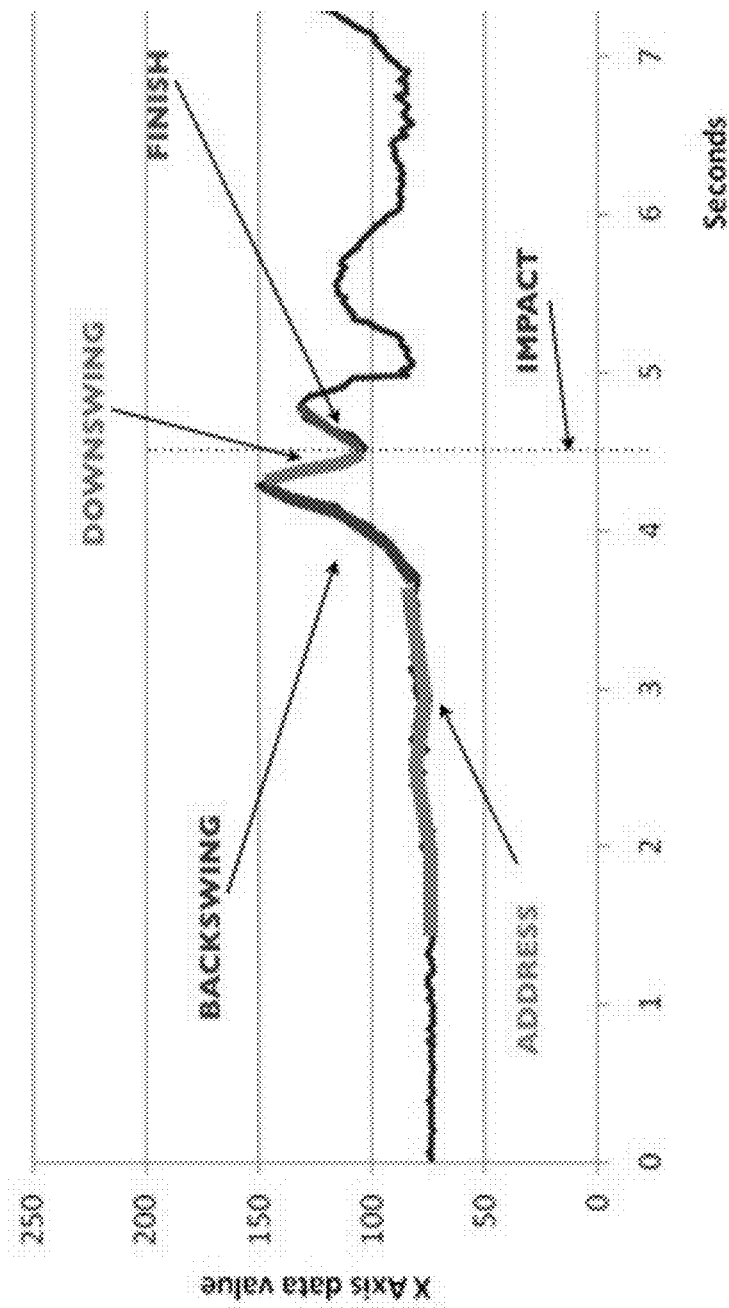
FIG. 42 shows a graph of swing data as obtained from one or more embodiments of the motion capture element.

FIG. 42 shows a graph of swing data as obtained from one or more embodiments of the invention. Any other user-friendly display may be utilized that includes spatial data obtained from one or more embodiments of the invention as one skilled in the art will recognize. In the figure as shown, the X-axis data may be utilized to show position versus time to graphically display information related to a golf swing. Any other display as previously described above may also be utilized to display spatial data associated with one or more embodiments of the invention.

Figure 43A:
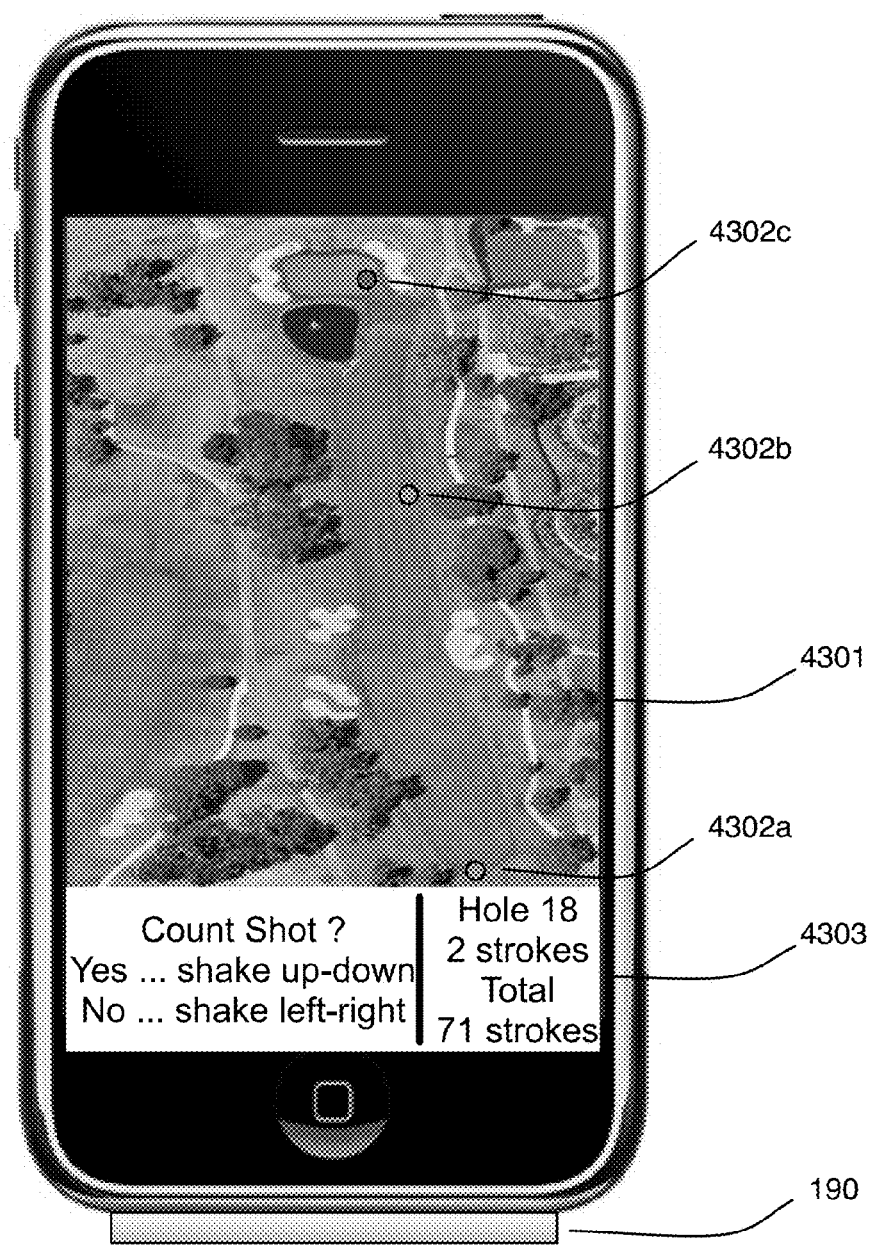
FIG. 43A shows a user interface that displays a query to the golfer to enable the golfer to count a shot or not.
Figure 44:
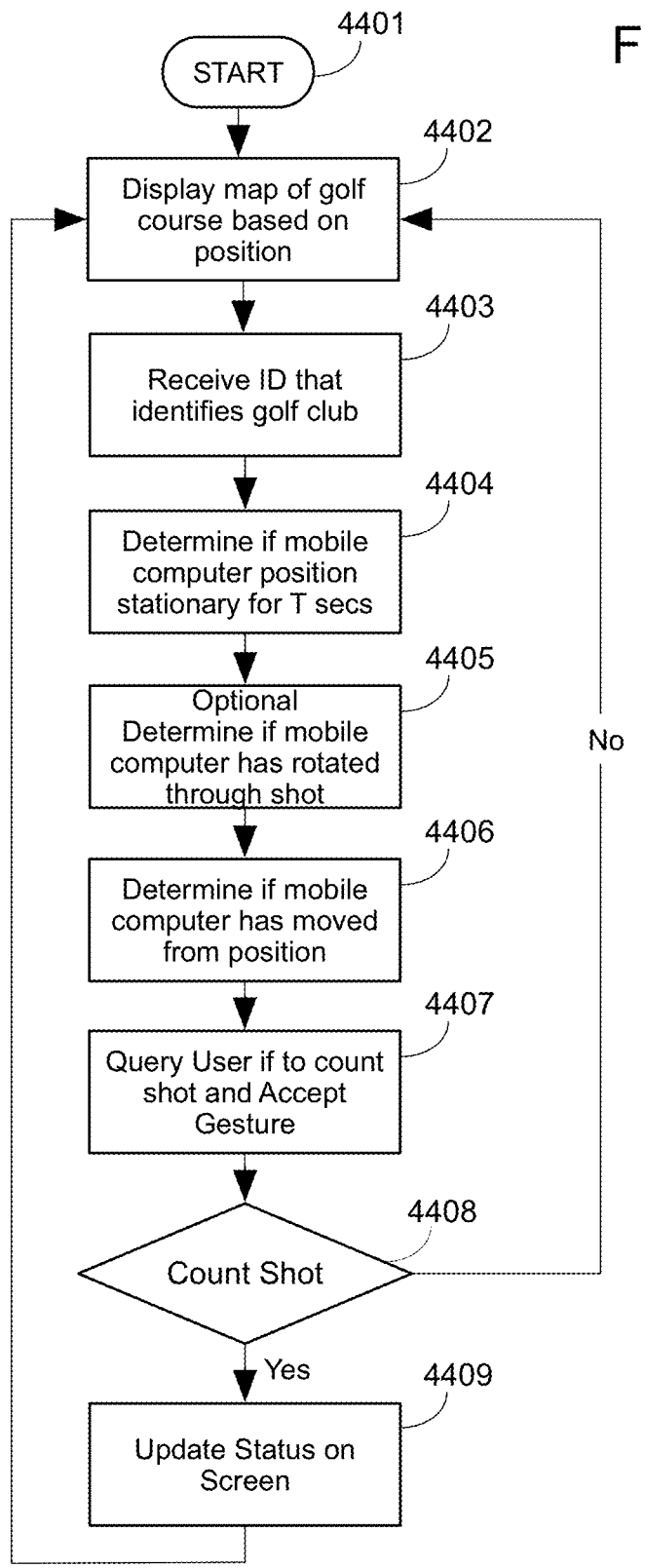
FIG. 44 shows a flow chart of an embodiment of the functionality specifically programmed into the mobile device in order to intelligently determine whether to query a golfer to count a shot and to record shots that are so designated.

FIG. 43A shows a user interface that displays a query to the golfer to enable the golfer to count a shot or not. As shown, map 4301 may show a satellite image of the location of the mobile computer as determined for example by a GPS chip in the mobile computer or via triangulation of a wireless or phone signal. Shots 4302a and 4302b may be shown in any manner to signify that these shots have been counted at the particular location. Lines may optionally be drawn between shots for example. Optionally, these shot displays may include the club number or any other desired information where a shot has taken place and been counted. Potential shot 4302c may be shown in any other manner which signifies that the shot is under consideration for a counted shot, as the mobile computer is currently querying the user as to whether or not to count the shot as is shown on the left side of status display 4303, i.e., "Count Shot ?". The mobile computer may accept any type of input for counting the shot including audio or tactile input based input, including motion sensing of the mobile computer to determine if the user has for example input a gesture such as a shake left/right meaning "no", do not count the shot, or a shake up/down meaning "yes" count the shot. This allows for operation of the mobile computer without removal of gloves as many mobile computers require direct skin contact to effect input. In addition, as shown if the shot is counted, the total number of shots on the course may be updated as per the right side of status display 4303. The logic for determining whether to query the user is shown in FIG. 44. If the shot is counted the shot display at 4302c for example may be shown in a different manner that signifies that indeed, the shot has been counted. For embodiments of the invention that utilize passive RFID sensors, the processing and logic of whether to count the shot requires no electronics at all on the golf club that require local power. For example, passive RFID chips can be powered remotely via RFID reader 190 that couples to the mobile computer for example. In this manner, all complexity of known systems for counting shots including utilization of switches, solar cells, buttons, battery operated electronics is completely eliminated. An RFID marker that is passive may be attached in any manner to a golf club, include adhering the RFID marker to the shaft or under the handle or in any other position on the club. In one or more embodiments a set of RFID tape strips may be purchased by the golfer and attached to the clubs wherein the mobile computer may query the user for which club number corresponds to which RFID tag for example. Alternatively the tape strips for example that attach RFID element 191 to the golf club (see FIG. 1), may already have a club number associated with each RFID element, for example a number written on the tag or packing of each tag. Alternatively, the mobile computer may also utilize motion capture data for embodiments that include motion capture elements on clubs in order to determine when a shot or potential shot has taken place.

Figure 43B:
FIG. 43B shows a user interface that displays a map of the golf course and locations of golf shots along with the particular club used at each shot location.

FIG. 43B shows a user interface that displays a map of the golf course and locations of golf shots along with the particular club used at each shot location on two different types of mobile computers. As shown, shot 4302b is annotated with "4 iron" and "210 yards" and a metric or score of the stroke in terms of efficiency or power (see FIG. 43C). Status area 4310 allows for displaying hole by hole shots for example. In this embodiment, it is not required that the mobile computers obtain an identifier from each club in a passive manner, but may obtain the identifier for each club via active wireless technologies if desired. Alternatively, the mobile computers shown in FIG. 43B may couple with an RFID or other passive reader (see element 190 in FIG. 43A for example).

Figure 43C:
FIG. 43C shows a user interface that displays a metrics associated with each shot at each of the locations shown in FIGS. 43A and 43B.

FIG. 43C shows a user interface that displays a metrics 4320 associated with each shot at each of the locations shown in FIGS. 43A and 43B. This display may be shown for example after the golfer counts a golf shot, for example by shaking the mobile computer or otherwise asserting that the golf shot should count. This display may be shown first or after the map shots as per FIGS. 43A and 43B, or may be shown after a delay of showing the map shots, or in any other manner. The display may be color coded to show a powerful or efficient shot as shown in the right picture, or to show a less powerful or less efficient shot, i.e., background of the display may be color coded or any portion of the display may be color coded for example.

FIG. 44 shows a flow chart of an embodiment of the functionality specifically programmed into the mobile device in order to intelligently determine whether to query a golfer to count a shot and to record shots that are so designated. Processing starts at 4401, for example when a golfer initializes the shot count application on the mobile computer (see FIG. 1 as well for different embodiments of the mobile computer). The mobile computer may display a map at 4402 as obtained for example over the Internet or stored locally based on a GPS position determined by the mobile computer (or by known triangulation techniques as previously described). The mobile computer may then read an identifier associated with a club at 4403. The mobile computer may utilize RFID reader 190, or for embodiments that do not utilize RFID, may use BLUETOOTH® for example to read an identifier for a club from the motion capture element if one exists. If multiple clubs are within range, then the system may query the user as to which club, or the club with the strongest signal may be automatically chosen for example. Any other method of arbitrating the identifier of the club is in keeping with the spirit of the invention. For example, RFID reader 190 may be purposefully limited in range so that only a club in near proximity to the mobile computer, as worn for example by the golfer, is readable. This embodiment requires no power, switches or batteries on each golf club and therefore is much simpler to maintain and use than known solutions for counting golf shots. If the mobile computer is stationary for a threshold T amount of time at 4404, then the mobile computer may either optionally determine if the mobile computer has rotated or moved in a manner that is indicative of a golf swing or putt at 4405, or simply wait until the mobile computer has moved from the current position at 4406 for example, which occurs once a golfer has finished a shot or putt. For example, current mobile computers may be equipped with motion detection elements internally, and which are therefore able to determine if a user has rotated (for a driver) or translated slightly (for a putter) for example, and determine that a shot (or practice swing/shot) has occurred. The mobile computer then queries the golfer at 4407 as to whether or not to count the shot and accepts any desired input gesture to indicate whether to count or not count the shot. For example, by allowing the user to input a shake or rotation of the mobile computer, that commonly have orientation and motion sensors built in, then the golfer is not required to take any gloves off, which is generally required to activate the touch screen features of some mobile computers. Querying the user may include use of a vibration component in the mobile computer, i.e., so that no sound is required to query the golfer, which may upset other golfer attempting to concentrate. If the golfer determines that the golf shot should be counted, then the status of the shot may be updated to indicate that the shot has counted, and for example the location on the course where the shot occurred. Embodiments that utilize motion capture elements can also optionally utilize this method to count shots and in addition may include other steps that detect the signature vibrations of a golf club to determine if a golf ball has been struck as well, etc., as explained below (see also FIGS. 45-49). Identifiers associated with the motion capture elements in these embodiments may be used in place of, or in combination with RFID associated identifiers to signify the type of club and/or club number of the golf club for example. In addition, processing continues at 4402 where the map is updated as the golfer moves until another club identifier is received at 4403 for example. If the shot is not to count as per 4408, then processing continues at 4402 without any update of the total shot count and the queried shot display, for example at 4302*c* may be removed from the display (see FIG. 43). Other embodiments may utilize a starting zone for each hole of a golf course or may allow other inputs for the golfer to signify which hole the shot is to count for. By saving all of the locations of the shots and the club number of each shot, statistics may be derived for later display by the golfer, either on the mobile computer or uploaded to a website for example. Any other method of displaying the shots as obtained by embodiments of the invention is in keeping with the spirit of the invention.

Figure 45:
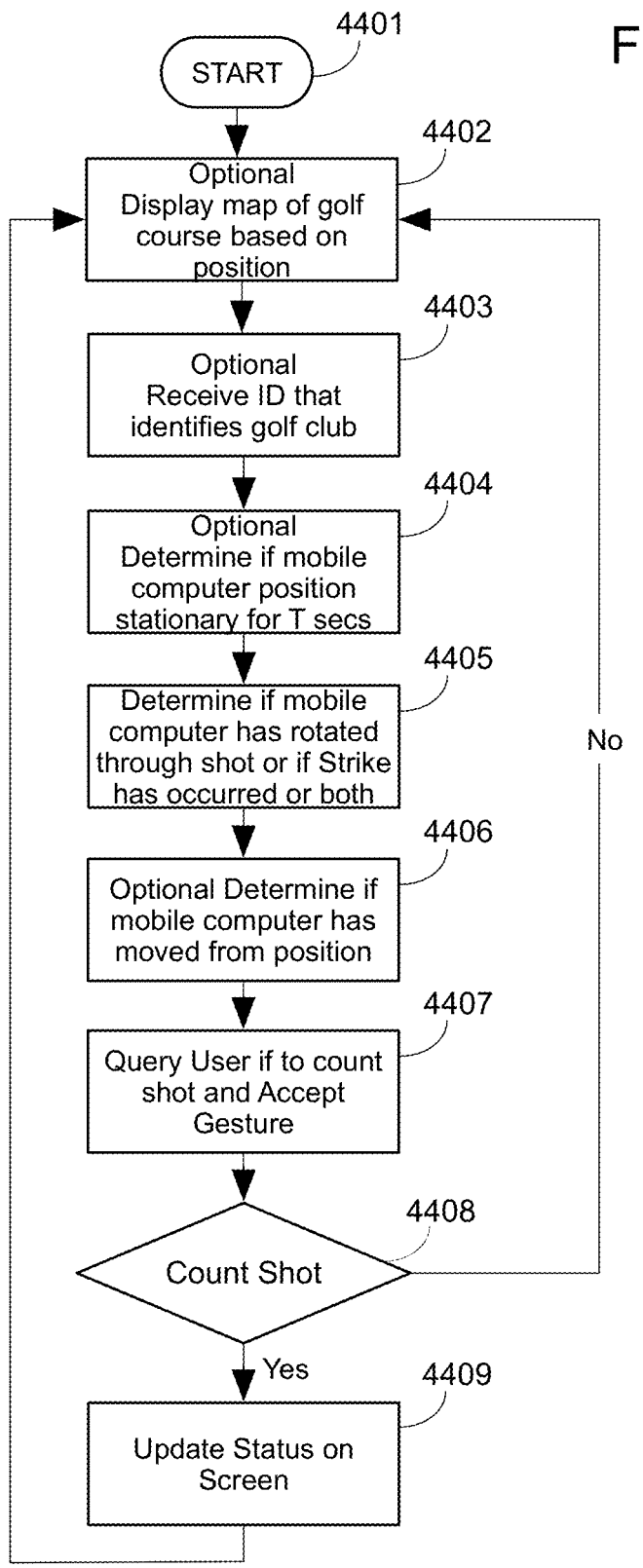
FIG. 45 shows a flow chart of an embodiment of the functionality specifically programmed into the mobile computer and/or motion capture element microcontroller in order to intelligently determine whether to query a golfer to count a shot and to record shots that are so designated.

FIG. 45 shows a flow chart of an embodiment of the functionality specifically programmed into the mobile computer and/or motion capture element microcontroller 3802 in order to intelligently determine whether to query a golfer to count a shot and to record shots that are so designated. Processing starts at 4401, for example when a golfer initializes the shot count application on the mobile computer (see FIG. 1 as well for different embodiments of the mobile computer), or for embodiments where the motion capture element stores data for an entire round without interfacing with a mobile computer, when the motion capture element moves. The mobile computer, if one is utilized at the time, may display a map at 4402 as obtained for example over the Internet or stored locally based on a GPS position determined by the mobile computer (or by known triangulation techniques as previously described). The mobile computer, again if one is being utilized at the time, may then read an identifier associated with a club at 4403. The mobile computer may utilize RFID reader 190, or for embodiments that do not utilize RFID, may use BLUETOOTH® for example to read an identifier for a club from the motion capture element if one exists. If multiple clubs are within range, then the system may query the user as to which club, or the club with the strongest signal may be automatically chosen for example. Any other method of arbitrating the identifier of the club is in keeping with the spirit of the invention. For example, RFID reader 190 may be purposefully limited in range so that only a club in near proximity to the mobile computer, as worn for example by the golfer, is readable. Optionally, if the mobile computer, if one is being used, is stationary for a threshold T amount of time at 4404, then the mobile computer may either optionally determine if the mobile computer has rotated or moved in a manner that is indicative of a golf swing or putt at 4405, or if a strike has occurred (see FIGS. 46-48) or simply optionally wait until the mobile computer has moved from the current position at 4406 for example, which occurs once a golfer has finished a shot or putt. For example, current mobile computers may be equipped with motion detection elements internally, and which are therefore able to determine if a user has rotated (for a driver) or translated slightly (for a putter) for example, and determine that a shot (or practice swing/shot) has occurred. Embodiments of the invention may also check for rotation or movement of the mobile computer and/or check for a strike alone or in combination. Embodiments of the invention may also check for both a rotation or movement indicative of a shot and a strike occurrence from a motion capture element to indicate that a shot has occurred for a robust embodiment. Alternatively, the motion capture element alone may be utilized to determine if a strike has occurred, which represents a potential shot to count. See FIGS. 46-48 for example. The mobile computer then queries the golfer at 4407 as to whether or not to count the shot and accepts any desired input gesture to indicate whether to count or not count the shot. For example, by allowing the user to input a shake or rotation of the mobile computer, that commonly have orientation and motion sensors built in, then the golfer is not required to take any gloves off, which is generally required to activate the touch screen features of some mobile computers. Querying the user may include use of a vibration component in the mobile computer, i.e., so that no sound is required to query the golfer, which may upset other golfer attempting to concentrate. If the golfer determines that the golf shot should be counted, then the status of the shot may be updated to indicate that the shot has counted, and for example the location on the course where the shot occurred. In addition, processing continues at 4402 where the map is updated as the golfer moves until another club identifier is received at 4403 for example. If the shot is not to count as per 4408, then processing continues at 4402 without any update of the total shot count and the queried shot display, for example at 4302*c* may be removed from the display (see FIG. 43). Other embodiments may utilize a starting zone for each hole of a golf course or may allow other inputs for the golfer to signify which hole the shot is to count for. By saving all of the locations of the shots and the club number of each shot, statistics may be derived for later display by the golfer, either on the mobile computer or uploaded to a website for example. Any other method of displaying the shots as obtained by embodiments of the invention is in keeping with the spirit of the invention.

One or more embodiments of the motion capture element collect, store, transmit and analyze data as follows. In one or more embodiment, one or more of the sensors in the motion capture element are placed in a data collection mode. While in the data collection mode, the motion capture element may continuously record sensor data in memory.

Figure 46:
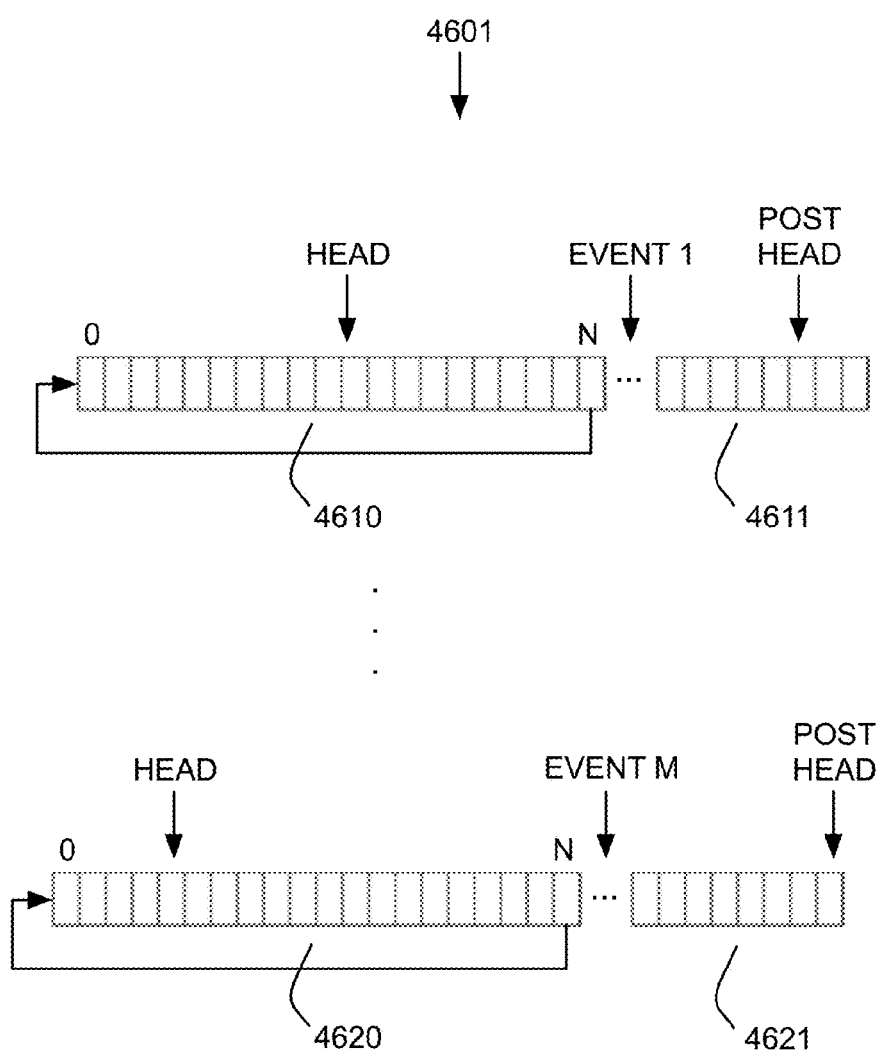
FIG. 46 illustrates an embodiment of the memory utilized to store data.

FIG. 46 illustrates an embodiment of the memory utilized to store data. Memory 4601 may for example be integral to microcontroller 3802 in FIG. 38 or may couple with the microcontroller, as for example a separate memory chip (not shown in FIG. 38 as one skilled in the art will recognize that microcontroller 3802 may attach to a separate memory chip or external memory over radio/antenna 3803 that may be located anywhere). Memory 4601 as shown collectively in FIG. 46 may be configured to include one or more memory buffer 4610, 4611 and 4620, 4621 respectively. One embodiment of the memory buffer that may be utilized is a ring buffer. The ring buffer may be implemented to be overwritten multiple times until an event occurs. The length of the ring buffer may be from 0 to N memory units. There may for example be M ring buffers, for M strike events for example. The number M may be any number greater than zero. In one or more embodiments, the number M may be equal to or greater than the number of shots for a round of golf, or any other number for example that allows all motion capture data to be stored on the motion capture element until downloaded to a mobile computer or the Internet after one or more shots. In one embodiment, a pointer, for example called HEAD keeps track of the head of the buffer. As data is recorded in the buffer, the HEAD is moved forward by the appropriate amount pointing to the next free memory unit. When the buffer becomes full, the pointer wraps around to the beginning of the buffer and overwrites previous values as it encounters them. Although the data is being overwritten, at any instance in time (t), there is recorded sensor data from time (t) back depending on the size of the buffer and the rate of recording. As the sensor records data in the buffer, an "Event" in one or more embodiments stops new data from overwriting the buffer. Upon the detection of an Event, the sensor can continue to record data in a second buffer 4611 to record post Event data, for example for a specific amount of time at a specific capture rate to complete the recording of a prospective shot. Memory buffer 4610 now contains a record of data for a desired amount of time from the Event backwards, depending on the size of the buffer and capture rate along with post Event data in the post event buffer 4611.

For example, in a golf swing, the event can be the impact of the club head with the ball. Alternatively, the event can be the impact of the club head with the ground, which could give rise to a false event. The Pre-Event buffer stores the sensor data up to the event of impact, the Post-Event buffer stores the sensor data after the impact event. One or more embodiments of microcontroller 3802 are configured to analyze the event and determine if the event is a strike or a false strike. If the event is considered a strike, and not a false strike, then another memory buffer 4620 is used for motion capture data up until the occurrence of a second event. After that strike occurs, the post event buffer 4621 is filled with captured data.

Specifically, sensor 3801 may be implemented as one or more MEMs sensors. The sensors may be commanded to collect data at specific time intervals. At each interval, data is read from the various MEMs devices, and stored in the ring buffer. A set of values read from the MEMs sensors is considered a FRAME of data. A FRAME of data can be 0, 1, or multiple memory units depending on the type of data that is being collected and stored in the buffer. A FRAME of data is also associated with a time interval. Therefore frames are also associated with a time element based on the capture rate from the sensors. For example, if each Frame was filled at 2 ms intervals, then 1000 FRAMES would contain 2000 ms of data (2 seconds). In general, a FRAME does not have to be associated with time.

Data can be constantly stored in the ring buffer and written out to non-volatile memory or sent over a wireless or wired link over radio/antenna 3803 to a remote memory or device for example at specified events, times, or when communication is available over radio/antenna 3803 to a mobile device or any other computer or memory, or when commanded for example by a mobile device, i.e., "polled", or at any other desired event.

Figure 47:
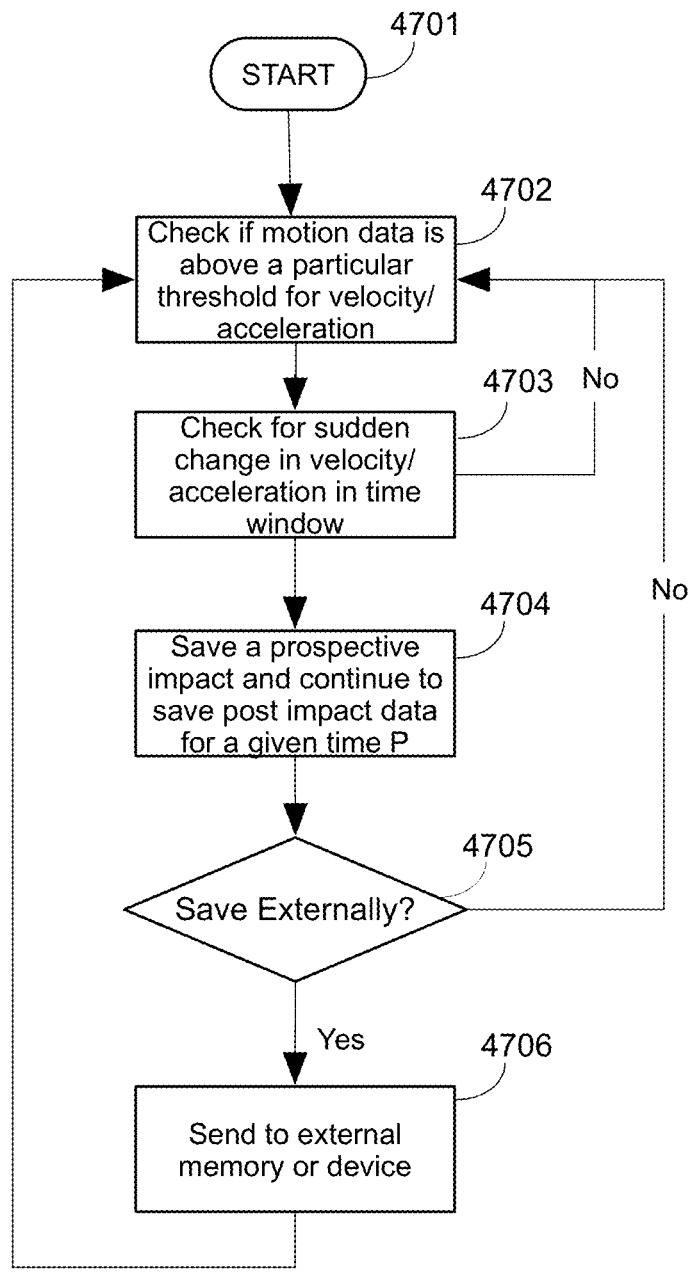
FIG. 47 shows a flow chart of an embodiment of the functionality specifically programmed into the microcontroller to determine whether a prospective strike has occurred.

FIG. 47 shows a flow chart of an embodiment of the functionality specifically programmed into the microcontroller to determine whether a prospective strike has occurred. The shockwave that occurs from an impact to the sporting equipment is transmitted to the sensor in the motion capture element, which records the motion capture data as is described in FIG. 46 above. Microcontroller 3802 is configured to then analyze the event and determine whether the event is a prospective strike with a ball for example or not.

One type of event that occurs is a strike of the clubface when it impacts a golf ball. In other sports that utilize a ball and a striking implement, the same analysis is applied, but tailored to the specific sport and sporting equipment. In tennis a prospective strike can be the racquet hitting the ball, for example as opposed to spinning the racquet before receiving a serve. In other applications, such as running shoes, the impact detection algorithm can detect the shoe hitting the ground when someone is running. In exercise it can be a particular motion being achieved, this allows for example the counting of repetitions while lifting weights or riding a stationary bike.

For golf related scenarios, microcontroller 3802 is configured to analyze the motion capture data to determine when the golf club for example has impacted an object, such as but not limited to a golf ball, tee, or the ground. The impact shock wave at the club head is transmitted to the sensor. In one or more embodiments of sensor 3801, position, orientation, velocity and/or accelerometer data is collected to sense these quantities with respect to one or more axes, for example accelerations on three accelerometer axes. Since all impacts are recorded, such as an impact of the club with a tee or the ground, the impacts are next analyzed to determine if the strike is valid or not valid with respect to a strike of a golf ball.

In one or more embodiments of the invention, processing starts at 4701. Microcontroller 3802 compares the motion capture data in memory 4610 with linear velocity over a certain threshold at 4702, within a particular impact time frame and searches for a discontinuity threshold where there is a sudden change in velocity or acceleration above a certain threshold at 4703. If no discontinuity in velocity or for example acceleration occurs in the defined time window, then processing continues at 4702. If a discontinuity does occur, then the prospective impact is saved in memory and post impact data is saved for a given time P at 4704. For example, if the impact threshold is set to 12G, discontinuity threshold is set to 6G, and the impact time frames is 10 frames, then microcontroller 3802 signals impact, after detection of a 12G acceleration in at least one axis or all axes within 10 frames followed by a discontinuity of 6G. In a typical golf swing, the accelerations build with smooth accelerations curves. Impact is signaled as a crash and quick change in acceleration/velocity. These changes are distinct from the smooth curves created by an incrementally increasing or decreasing curves of a golf swing. If data is to be saved externally as determined at 4705, i.e., there is a communication link to a mobile device and the mobile device is polling or has requested impact data when it occurs for example, then the impact is transmitted to an external memory, or the mobile device or saved externally in any other location at 4706 and processing continues again at 4702 where microcontroller 3802 analyzes collected motion capture data for subsequent impacts. If data is not to be saved externally, then processing continues at 4702 with the impact data saved locally in memory 4601.

The impact event is defined in one embodiment, as all accelerometer axes reaching an impact threshold G force within a specified time frame, called the impact time frame. This alone is not sufficient to detect impact since a fast swing could reach the impact threshold, i.e., without contacting the golf ball, for example a practice swing. The discontinuity threshold signals the rapid change of accelerometer values that signify sudden impact. The impact time frame may be implemented as a sliding window that defines a time frame in which impact is detected. If the impact threshold and discontinuity threshold are reached on all axes within the impact time frame, then impact is signaled and the event as shown in FIG. 46, for example Event 1, is saved and data is then collected in the next memory buffer. One or more embodiments of the invention may transmit the event to a mobile device and/or continue to save the events in memory, for example for a round of golf or until a mobile device communication link is achieved.

For example, if impact threshold for X is reached at time t, and impact threshold Y is reached at time t+n, and t+n is outside the impact time frame, then no impact is detected. For example, practice swings do not trigger impact events.

In one or more embodiments of the invention, further analysis of the impact event occurs to reduce false positives of impact events. As described, microcontroller 3802 searches for a linear velocity to reach a certain threshold, and a discontinuity in the linear velocity. Hence, microcontroller 3802 will not trigger an impact in a full motion swing where there is no "crash" or physical impact. However, a prospective impact event will trigger if the club is tapped on the ground or against any other object. However, since a typical golf swing has a very characteristic angular and linear velocity signature, the motion capture data may be utilized to determine whether the prospective impact was a result of a typical golf swing. For example, microcontroller 3802 may compare the motion capture data with this signature to predict the occurrence of a typical golf swing, in order to classify the impact as a valid golf club and golf ball impact.

Figure 48:
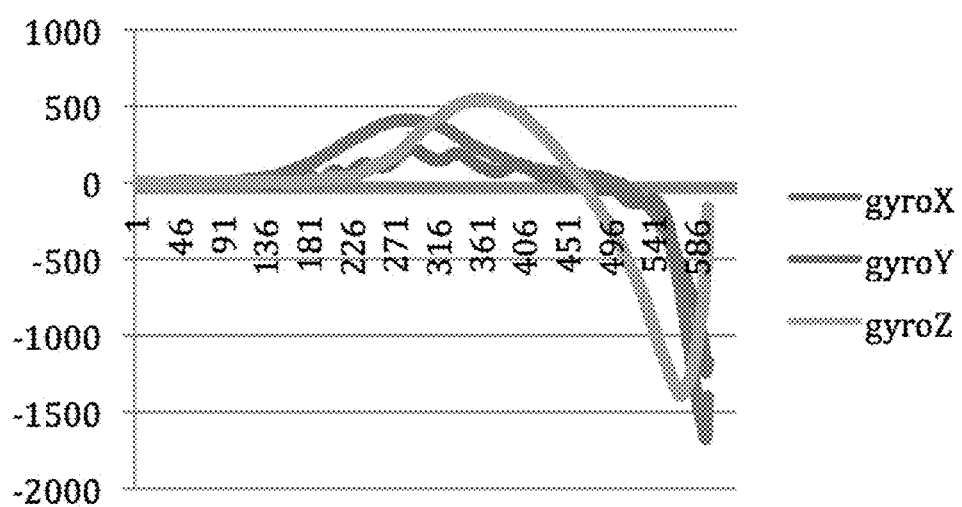
FIG. 48 illustrates a typical golf swing signature, which is compared to motion capture data to eliminate false positive impact events.

For example, with the sensor mounted in the handle, a typical golf swing signature is shown in FIG. 48. In one or more embodiments, microcontroller 3802 is configured to execute a pattern matching algorithm to follow the curves for each of the axis and use segments of 1 or more axis to determine if a characteristic swing has taken place. If the motion capture data in memory 4601 is within a range close enough to the values of a typical swing as shown in FIG. 48, then the motion of the club is consistent with a swing, whether a practice swing or swing that results in an impact with a golf ball. For example, axis-X shows a climb between frame 161 to 289, followed by a steep decline between 545 to 577. Microcontroller 3802 utilizes this information to recognize that there is a backswing, followed by a downswing. If this occurs and an impact occurs as described with respect to FIG. 47, then a valid golf club and golf ball impact is signaled. Microcontroller 3802 may also utilize the time between a backswing and downswing events to validate that a swing has taken place. Embodiments of the invention thus reduce the number of false positives in impact detection, after first characterizing the angular and/or linear velocity signature of the movement, and then utilizing elements of this signature to determine if similar signatures for future events have occurred.

The motion capture element collects data from various sensors. The data capture rate is high and there is significant amounts of data that is being captured. Embodiments of the invention may use both lossless and lossy compression algorithms to store the data on the sensor depending on the particular application. The compression algorithms enable the motion capture element to capture more data within the given resources. Compressed data is also what is transferred to the remote computer(s). Compressed data transfers faster. Compressed data is also stored in the Internet "in the cloud", or on the database using up less space locally.

Over the air programming is enabled in one or more embodiments of the invention to enable the update of the firmware stored in the motion capture element. An initial bootloader is stored in non-volatile memory on the motion capture element that provides the basic services to communicate with a remote system. There is also a dual image storage capability on the module. Once an application image is loaded, a CRC check may be performed against the newly downloaded image. If the downloaded firmware passes the various checks, then the microcontroller boots from the new image, and the old image is flagged old.

In order to calibrate large amounts of sensors for manufacturing, one or more embodiments of the motion capture elements may be mounting on a platform and tested in parallel. In this manner, the electrical functional as well as the calibration of the various sensors may be performed rapidly. A hexapod is one embodiment of a test bed that may be utilized to calibrate motion related parameters on multiple motion capture elements at once.

While the ideas herein disclosed has been described by means of specific embodiments and applications thereof, numerous modifications and variations could be made thereto by those skilled in the art without departing from the scope of the invention set forth in the claims.

What is claimed is:

1. A motion capture and analysis system comprising:
   at least one motion capture element configured to couple with a user or piece of equipment,
      wherein said at least one motion capture element comprises
      a memory;
      a sensor configured to capture one or more values associated with an orientation, a position, a velocity, and an acceleration of said at least one motion capture element;
      a first communication interface;
      a microcontroller coupled with said memory, said sensor and said radio, wherein
         said microcontroller is configured to
            collect data that comprises sensor values from said sensor;
            store said data in said memory;
            transmit said data via said first communication interface;
   said microcontroller configured to transmit said data to a computer that comprises
      a display;
      a second communication interface configured to communicate with said first communication interface to obtain said data;
      wherein said computer is coupled with said display and said second
         communication interface, and wherein said computer is configured to
            accept an input from a user that signifies a type of motion selected from a plurality of types of motion and recognize said at least one motion capture element associated with said user or said piece of equipment to associate said at least one motion capture element with an assigned location or assigned locations on said user or said piece of equipment based on said type of motion or
            receive said data associated with said at least one motion capture element via said second communication interface and analyze said data to form motion analysis data and that signifies a type of motion selected from a plurality of types of motion and recognize said at least one motion capture element associated with said user or said piece of equipment to associate said at least one motion capture element with an assigned location or assigned locations on said user or said piece of equipment based on said type of motion; display said motion analysis data on said display; and, store said data, or said motion analysis data, or both said data and said motion analysis data.

2. The system of claim 1 wherein said microcontroller is further configured to detect a first value from said sensor values having a first threshold value and detect a second value from said sensor values having a second threshold value with a time window;

signify a prospective event;

compare said prospective event to a characteristic signal associated with a typical event and eliminate any false positive events;

signify a valid event if said prospective event is not a false positive event; and, save said valid event in said memory as said data.

3. The system of claim 1 wherein said microcontroller is further configured to store said data in said memory at least until a communications link to said computer exists and said data has been transferred to said computer.

4. The system of claim 1 wherein said microcontroller is further configured to transmit said data in said memory after an event or periodically or when requested by said computer.

5. The system of claim 1 wherein said microcontroller is configured to power off if no motion is detected for a predefined time.

6. The system of claim 1 wherein said microcontroller is configured to power on when motion is detected via said sensor or via a passive motion detector that requires no power.

7. The system of claim 1 wherein said computer is further configured to tweet or transmit said data to a social network site.

8. The system of claim 1 further comprising a remote database coupled with said computer wherein said data in said remote database is stored, retrieved, viewed, analyzed or data mined.

9. The system of claim 8 claim 1 wherein said data in said remote database is utilized to play a game comprising one or more total players wherein said game utilizes actual data obtained from said at least one motion capture element.

10. The system of claim 8 wherein data associated with a second user is obtained from said remote database located remote to said computer and wherein said data associated with said second user is utilized to play a game with said user wherein said game utilizes actual data obtained from said at least one motion capture element associated with said second user.

11. The system of claim 8 wherein data associated with a second user is obtained from said remote database located remote to said computer and wherein said data associated with said second user is utilized to play a game with said user wherein said game utilizes actual data obtained from said at least one motion capture element associated with said second user and wherein said game comprises virtual reality or augmented virtual reality.

12. The system of claim 1 wherein said computer comprises at least one camera coupled with said computer and wherein said computer is further configured to command said at least one camera to capture one or more images associated with said at least one motion capture element.

13. The system of claim 1 wherein said computer comprises at least one camera coupled with said computer and wherein said computer is further configured to command said at least one camera to capture one or more images associated with a second user associated with said at least one motion capture element.

14. The system of claim 1 further comprising one or more cameras external to said computer that are utilized to obtain one or more images that are augmented with said data, or said motion analysis data, or both said data and said motion analysis data and wherein said one or more images are then broadcast to televisions or to the Internet.

15. The system of claim 1 wherein said display of said motion analysis comprises display of a rating or a calculated ball flight path or a time line showing points in time along a time axis where peak values occur or an impact location of a ball on said piece of equipment or any combination thereof associated with said motion analysis data.

16. The system of claim 1 wherein said display of said motion analysis comprises display of a suggest training regimen to aid said user in improving mechanics of said user.

17. The system of claim 1 wherein said computer is further configured to present an interface to enable said user to purchase said piece of equipment over said wireless communication interface.

18. The system of claim 1 wherein said computer is further configured to present an interface to enable said user to order a customer fitted piece of equipment over said wireless communication interface.

19. The system of claim 1 further comprising a battery coupled with said at least one motion capture element and further coupled with a mechanical charger.

20. The system of claim 1, wherein said sensor is further configured to power on or power off using one or more gestures, wherein said one or more gestures include one or more of motion, physical switches, contact with said sensor and wireless commands to said sensor.

21. The system of claim 1, wherein said computer receives data from a plurality of motion capture elements and compares said data from each of said motion capture sensors to determine said assigned locations on said user or said piece of equipment based on said.

22. The system of claim 1 wherein said computer is further configured to display a location where said at least one motion capture element is currently placed or is to be placed on said user or said piece of equipment;

prompt said user to move said at least one motion capture element that is currently placed or is to be placed on said location on said user or on said piece of equipment to associate said at least one motion capture element with assigned locations on the user's body or on said piece of equipment to acknowledge which motion capture element of said at least one motion capture element said computer is requesting identity for;

accept said data comprising an identity from said at least one motion capture element;

obtain said identity of a particular motion capture element based on said data;

assign said identity of said particular motion capture element to said location where said at least one motion capture element is currently placed or is to be placed on said user or on said piece of equipment based on said motion capture data from said at least one motion capture element obtained after said prompt.

23. The system of claim 1 wherein said computer is further configured to display at least one image or representation of said user in association with said motion analysis data that comprises a metric or three-dimensional graphic.

24. The system of claim 1 wherein said computer is further configured to display at least one image or representation of said user in association with said motion analysis data that comprises a metric or three-dimensional graphic from a plurality of viewpoints.

25. The system of claim 1 wherein said at least one motion capture element further comprises:

a visual marker on an external surface of said at least one motion capture element that comprises a plurality of positionally offset visual elements positioned on a background color, wherein said plurality of positionally offset visual elements are arranged in a non-linear pattern and are offset from each other and comprise positionally offset dots or non-parallel lines or both said positionally offset dots and said non-parallel lines, wherein the plurality of positionally offset visual elements enable visual determination of a rotational orientation of the visual marker, wherein each of said plurality of positionally offset visual elements comprise differing visual characteristics than said background color.

26. A motion capture and analysis system comprising:

at least one motion capture element configured to couple with a user or piece of equipment, wherein said at least one motion capture element comprises a memory;

a sensor configured to capture one or more values associated with an orientation, a position, a velocity, and an acceleration of said at least one motion capture element;

a first communication interface;

a microcontroller coupled with said memory, said sensor and said radio, wherein said microcontroller is configured to collect data that comprises sensor values from said sensor;

store said data in said memory;

transmit said data via said first communication interface;

said microcontroller configured to transmit said data to a computer that comprises a display;

a second communication interface configured to communicate with said first communication interface to obtain said data;

wherein said computer is coupled with said display and said second communication interface, and wherein said computer is configured to accept an input from a user that signifies a type of motion selected from a plurality of types of motion and recognize said at least one motion capture element associated with said user or said piece of equipment to associate said at least one motion capture element with an assigned location or assigned locations on said user or said piece of equipment based on said type of motion and receive said data associated with said at least one motion capture element via said second communication interface and analyze said data to form motion analysis data and that signifies a type of motion selected from a plurality of types of motion and recognize said at least one motion capture element associated with said user or said piece of equipment to associate said at least one motion capture element with an assigned location or assigned locations on said user or said piece of equipment based on said type of motion; display said motion analysis data on said display; and, store said data, or said motion analysis data, or both said data and said motion analysis data.

* * * * *